United States Patent
Fatheree et al.

(10) Patent No.: US 11,299,492 B2
(45) Date of Patent: Apr. 12, 2022

(54) JAK KINASE INHIBITOR COMPOUNDS FOR TREATMENT OF RESPIRATORY DISEASE

(71) Applicant: THERAVANCE BIOPHARMA R&D IP, LLC, South San Francisco, CA (US)

(72) Inventors: Paul R. Fatheree, San Francisco, CA (US); John R. Jacobsen, San Mateo, CA (US); Gary E. L. Brandt, Alameda, CA (US); Melissa Fleury, Brisbane, CA (US); Lan Jiang, Foster City, CA (US); Cameron Smith, San Bruno, CA (US); Steven D. E. Sullivan, San Francisco, CA (US); Lori Jean Van Orden, San Francisco, CA (US); Anne-Marie Beausoleil, Redwood City, CA (US)

(73) Assignee: Theravance Biopharma R&D IP, LLC, South San Francisco, CA (US)

( * ) Notice: Subject to any disclaimer, the term of this patent is extended or adjusted under 35 U.S.C. 154(b) by 0 days.

(21) Appl. No.: 17/248,015

(22) Filed: Jan. 5, 2021

(65) Prior Publication Data
US 2021/0130351 A1 May 6, 2021

Related U.S. Application Data

(62) Division of application No. 16/689,706, filed on Nov. 20, 2019, now Pat. No. 10,913,740, which is a division of application No. 16/215,194, filed on Dec. 10, 2018, now Pat. No. 10,526,330, which is a division of application No. 16/038,424, filed on Jul. 18, 2018, now Pat. No. 10,183,942, which is a division of application No. 15/341,226, filed on Nov. 2, 2016, now Pat. No. 10,100,049.

(60) Provisional application No. 62/250,113, filed on Nov. 3, 2015.

(51) Int. Cl.
| | |
|---|---|
| *C07D 471/04* | (2006.01) |
| *A61K 31/437* | (2006.01) |
| *A61K 31/416* | (2006.01) |
| *A61P 43/00* | (2006.01) |
| *A61P 11/06* | (2006.01) |
| *A61P 11/00* | (2006.01) |

(52) U.S. Cl.
CPC .......... *C07D 471/04* (2013.01); *A61K 31/416* (2013.01); *A61K 31/437* (2013.01); *A61P 11/00* (2018.01); *A61P 11/06* (2018.01); *A61P 43/00* (2018.01)

(58) Field of Classification Search
None
See application file for complete search history.

(56) References Cited

U.S. PATENT DOCUMENTS

| | | | |
|---|---|---|---|
| 6,534,524 | B1 | 3/2003 | Kania et al. |
| 6,884,890 | B2 | 4/2005 | Kania et al. |
| 7,884,109 | B2 | 2/2011 | Ohlmeyer et al. |
| 8,450,340 | B2 | 5/2013 | Hood et al. |
| 8,575,336 | B2 | 11/2013 | Coe et al. |
| 8,648,069 | B2 | 2/2014 | Akritopoulou-Zanze et al. |
| 8,895,544 | B2 | 11/2014 | Coe et al. |
| 10,100,049 | B2 | 10/2018 | Fatheree et al. |
| 10,183,942 | B2 | 1/2019 | Benjamin et al. |

(Continued)

FOREIGN PATENT DOCUMENTS

| | | |
|---|---|---|
| JP | 2010111624 A | 5/2010 |
| WO | 2005009389 A2 | 2/2005 |

(Continued)

OTHER PUBLICATIONS

Barnes et al., "Kinases as Novel Therapeutic Targets in Asthma and Chronic Obstructive Pulmonary Disease", Pharmacological Review, 68:788-815, Jul. 2016.

(Continued)

*Primary Examiner* — Joseph R Kosack
(74) *Attorney, Agent, or Firm* — Jeffrey A. Hagenah; Sheppard Mullin Richter & Hampton LLP

(57) ABSTRACT

The invention provides compounds of formula (I):

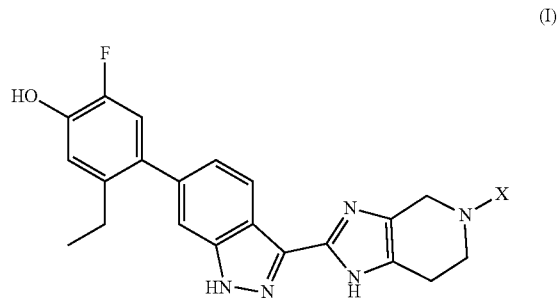

wherein X is

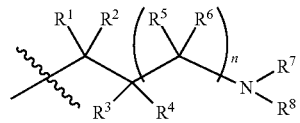

and the variables are defined in the specification, or a pharmaceutically-acceptable salt thereof, that are useful as JAK kinase inhibitors. The invention also provides pharmaceutical compositions comprising such compounds, methods of using such compounds to treat respiratory diseases, and processes and intermediates useful for preparing such compounds.

13 Claims, 2 Drawing Sheets

(56) References Cited

U.S. PATENT DOCUMENTS

| | | | |
|---|---|---|---|
| 10,196,393 | B2 | 2/2019 | Fatheree et al. |
| 10,208,040 | B2 | 2/2019 | Fatheree et al. |
| 10,251,874 | B2 | 4/2019 | Dabros et al. |
| 10,392,386 | B2 | 8/2019 | Fatheree et al. |
| 10,406,148 | B2 | 9/2019 | Thalladi et al. |
| 10,493,077 | B2 | 12/2019 | Fatheree et al. |
| 10,519,153 | B2 | 12/2019 | Fatheree et al. |
| 10,526,330 | B2 | 1/2020 | Fatheree et al. |
| 10,548,886 | B2 | 2/2020 | Kleinschek et al. |
| 10,550,118 | B2 | 2/2020 | Fatheree et al. |
| 10,836,763 | B2 | 11/2020 | Long et al. |
| 10,844,057 | B2 | 11/2020 | Colson et al. |
| 2005/0090529 | A1 | 4/2005 | McAlpine et al. |
| 2015/0158864 | A1 | 6/2015 | Thorarensen et al. |
| 2015/0329542 | A1 | 11/2015 | Coe et al. |
| 2016/0289196 | A1 | 10/2016 | Choi et al. |
| 2020/0046719 | A1 | 2/2020 | McKinnell et al. |
| 2020/0071323 | A1 | 3/2020 | Long et al. |
| 2020/0087303 | A1 | 3/2020 | Fatheree et al. |
| 2020/0121669 | A1 | 4/2020 | Thalladi et al. |
| 2020/0131178 | A1 | 4/2020 | Fatheree et al. |
| 2020/0181141 | A1 | 6/2020 | Fatheree et al. |
| 2020/0216447 | A1 | 7/2020 | Fatheree et al. |

FOREIGN PATENT DOCUMENTS

| | | | |
|---|---|---|---|
| WO | 2010039939 | A1 | 4/2010 |
| WO | 2010114971 | A1 | 10/2010 |
| WO | 2013014567 | A1 | 1/2013 |
| WO | 2014111380 | A1 | 7/2014 |
| WO | 2016026078 | A1 | 2/2016 |
| WO | 2017077283 | A1 | 5/2017 |
| WO | 2017077288 | A1 | 5/2017 |

OTHER PUBLICATIONS

Chander et al., "Lung lamellar bodies maintain an acidic internal pH", The Journal of Biological Chemistry, 261 (13):6126-6131 (1986).

International Search Report and the Written Opinion for PCT/US2016/059999 dated Feb. 20, 2017.

De Savi et al., "Efficacious inhaled PDE4 inhibitors with low emetic potential and long duration of action for the treatment of COPD", Journal of Medicinal Chemistry, 57:4661-4676 (2014).

Down et al., "Optimization of novel indazoles as highly potent and selective inhibitors of phosphoinositide 3-kinase delta for the treatment of respiratory disease" Journal of Medicinal Chemistry, 58:7381-7399 (2015).

Fenwick et al., "Effect of JAK inhibitors on release of CXCL9, CXCL10 and CXCL11 from human airway epithelial cells", PLOS One, 10(6):e0128757 (2015).

Foloppe et al., "Identification of a buried pocket for potent and selective inhibition of Chk1: Prediction and verification", Bioorganic & Medicinal Chemistry, 14:1792-1804 (2006).

Fowler et al., "Carbon-11 labeled aliphatic amines in lung uptake and metabolism studies: potential for dynamic measurements in vivo", The Journal of Pharmacology and Experimental Therapeutics, 198(1):133-145 (1976).

Hori et al., "Binding of basic drugs to rat lung mitochondria", Pharmaceutical Research, 4(2):142-146 (1987).

Horig et al., "From bench to clinic and back: Perspective on the 1st IQPC Translational Research conference", Journal of Translational Medicine, 2(44), (2004).

Jones et al., "Design and synthesis of a pan-janus kinase inhibitor clinical candidate (PF-0626276) suitable for inhaled and topical delivery for the treatment of inflammatory diseases of the lungs and skin", Journal of Medicinal Chemistry (2016).

Krejcie et al., "A recirculatory model of the pulmonary uptake and pharmacokinetics of lidocaine based on analysis of arterial and mixed venous data from dogs", Journal of Pharmacokinetics and Biopharmaceutics, 25(2):169-190 (1997).

McBride et al., "Design and structure-activity relationship of 3-benzimidazol-2-yl-1H-indazoles as inhibitors of receptor tyrosine kinases", Bioorganic & Medicinal Chemistry Letters, 16:3595-3599 (2006).

McBride et al., "3-Benzimidazol-2-yl-1H-indazoles as potent c-ABL inhibitors", Bioorganic & Medicinal Chemistry Letters, 16:3789-3792 (2006).

Minchin et al., "Effect of desmethylimipramine on the kinetics of chlorphentermine accumulation in isolated perfused rat lung", The Journal of Pharmacology and Experimental Therapeutics, 211(3):514-518 (1979).

Miniati et al., "Mitochondria act as a reservoir for the basic amine HIPDM in the lung", European Respiratory Journal, 9:2306-2312 (1996).

Orton et al., "Xenobiotic accumulation and metabolism by isolated perfused rabbit lungs", The Journal of Pharmacology and Experimental Therapeutics, 186(3):482-497 (1973).

Paci et al., "Lung tissue binding of iodobenzyl-propanediamine: involvement of beta-adrenergic receptors", 7 (12):1467-1472 (1989).

Roerig et al., "First-pass uptake of verapamil, diazepam, and thiopental in the human lung", Anesth Analg, 69:461-466 (1989).

Roerig et al., "Effect of plasma protein binding on the uptake of methadone and diazepam in the isolated perfused rat lung", Drug Metabolism and Disposition, 12(5):536-542 (1984).

Roth et al., "Action by the lungs on circulating xenobiotic agents, with a case study of physiologically based pharmacokinetic modeling of benzo(A)pyrene disposition", Pharmaceutical Therapy, 48:143-155 (1990).

Schafer et al., "Failure is an option: learning from unsuccessful proof-of-concept trials", Drug Discovery Today, 13 (21): 913-916 (Nov. 2008).

Shaw et al., "Optimization of platelet-derived growth factor receptor (PDGFR) inhibitors for duration of action, as an inhaled therapy for lung remodeling in pulmonary arterial hypertension", Journal of Medicinal Chemistry, 59:7901-7914 (2016).

Simov et al., "Structure-based design and development of (benz)imidazole pyridones as JAK1-selective kinase inhibitors", Bioorganic & Medicinal Chemistry Letters, 26:1803-1808 (2016).

Slosman et al., "Evaluation of [iodine-125]N,N,N'-trimethyl-N'-[2-hydroxy-3-methyl-5-iodobenzyl]-1,3-propanediamine lung uptake using an isolated-perfused lung model", Journal of Nuclear Medicine, 28(2):203-208 (1987).

Trujillo et al., "2-(6-Phenyl-1H-indazol-3-yl)-1H-benzo[d]imidazoles: Design and synthesis of a potent and isoform selective PKC-zeta inhibitor", Bioorganic & Medicinal Chemistry Letters, 19:908-911 (2009).

Vestal et al., "Active uptake of propranolol by isolated rabbit alveolar macrophages and its inhibition by other basic amines", The Journal of Pharmacology and Experimental Therapeutics, 214(1):106-111 (1980).

Waters et al., Facilitated uptake of fentanyl, but not alfentanyl, by human pulmonary endothelial cells, Anesthesiology, 93(3):825-831 (2000).

Waters et al., "Uptake of fentanyl in pulmonary endothelium", The Journal of Pharmacology and Experimental Therapeutics, 288(1):157-163 (1999).

Wilson et al., "Studies on the persistence of basic amines in the rabbit lung", Drug Metabolism and Disposition, 7(6):420-424 (1979).

Yan et al., "Discovery of 3-(5'-Substituted)-Benzimidazole-5-(1-(3,5-dichloropyridin-4-yl)ethoxy)-1H-indazoles as potent fibroblast growth factor inhibitors: Design, synthesis, and biological evaluation", Journal of Medicinal Chemistry, 59: 6690-6708 (2016).

Yoshida et al., "Contribution of monoamine oxidase (MAO) to the binding of tertiary basic drugs in lung mitochondria", Pharmaceutical Research, 6(10):877-882 (1989).

Zhou et al., "Tertiary amine mediated targeted therapy against metastatic lung cancer", Journal of Controlled Release, 241:81-93 (2016).

JAK KINASE INHIBITOR COMPOUNDS FOR TREATMENT OF RESPIRATORY DISEASE

CROSS-REFERENCE TO RELATED APPLICATIONS

This application is a divisional application of U.S. Ser. No. 16/689,706, filed on Nov. 20, 2019, now allowed, which is a divisional application of U.S. Ser. No. 16/215,194, filed on Dec. 10, 2018, now U.S. Pat. No. 10,526,330, which is a divisional application of U.S. Ser. No. 16/038,424, filed on Jul. 18, 2018, now U.S. Pat. No. 10,183,942, which is a divisional application of U.S. Ser. No. 15/341,226, filed on Nov. 2, 2016, now U.S. Pat. No. 10,100,049, which application claims the benefit of U.S. Provisional Application No. 62/250,113, filed on Nov. 3, 2015; the entire disclosures of which are incorporated herein by reference in their entirety.

BACKGROUND OF THE INVENTION

Field of the Invention

The invention is directed to diamino compounds useful as JAK kinase inhibitors. The invention is also directed to pharmaceutical compositions comprising such compounds, methods of using such compounds to treat respiratory diseases, and processes and intermediates useful for preparing such compounds.

State of the Art

Asthma is a chronic disease of the airways for which there are no preventions or cures. The disease is characterized by inflammation, fibrosis, hyperresponsiveness, and remodeling of the airways, all of which contribute to airflow limitation. An estimated 300 million people worldwide suffer from asthma and it is estimated that the number of people with asthma will grow by more than 100 million by 2025. In the United States, asthma afflicts about 6% to 8% of the population, making it one of the most common chronic diseases in the country. Although most patients can achieve control of asthma symptoms with the use of inhaled corticosteroids that may be combined with a leukotriene modifier and/or a long acting beta agonist, there remains a subset of patients with severe asthma whose disease is not controlled by conventional therapies. Severe persistent asthma is defined as disease that remains uncontrolled on high doses of inhaled corticosteroids. While severe asthmatics are estimated to account for approximately 5% of all asthma sufferers, they have a high risk of morbidity and mortality and are responsible for a disproportionate share of health care resource utilization among asthmatics. There remains a need for novel therapies to treat these patients.

Cytokines are intercellular signaling molecules which include chemokines, interferons, interleukins, lymphokines, and tumour necrosis factor. Cytokines are critical for normal cell growth and immunoregulation but also drive immune-mediated diseases and contribute to the growth of malignant cells. Elevated levels of many cytokines have been implicated in the pathology of asthma inflammation. For example, antibody-based therapies targeted at interleukins (IL)-5, and 13 have been shown to provide clinical benefit in subsets of severe asthma patients. Among the cytokines implicated in asthma inflammation, many act through signaling pathways dependent upon the Janus family of tyrosine kinases (JAKs), which signal through the Signal Transducer and Activator of Transcription (STAT) family of transcription factors. Cytokines implicated in asthma inflammation which signal through the JAK-STAT pathway include IL-2, IL-3, IL-4, IL-5, IL-6, IL-9, IL-11, IL-13, IL-23, IL-31, IL-27, thymic stromal lymphopoietin (TSLP), interferon-γ (IFNγ) and granulocyte-macrophage colony-stimulating factor (GM-CSF).

The JAK family comprises four members, JAK1, JAK2, JAK3, and tyrosine kinase 2 (TYK2). Binding of cytokine to a JAK-dependent cytokine receptor induces receptor dimerization which results in phosphorylation of tyrosine residues on the JAK kinase, effecting JAK activation. Phosphorylated JAKs, in turn, bind and phosphorylate various STAT proteins which dimerize, internalize in the cell nucleus and directly modulate gene transcription, leading, among other effects, to the downstream effects associated with inflammatory disease. The JAKs usually associate with cytokine receptors in pairs as homodimers or heterodimers. Specific cytokines are associated with specific JAK pairings. Each of the four members of the JAK family is implicated in the signaling of at least one of the cytokines associated with asthma inflammation. Consequently, a chemical inhibitor with pan-activity against all members of the JAK family could modulate a broad range of pro-inflammatory pathways that contribute to severe asthma.

However, the broad anti-inflammatory effect of such inhibitors could suppress normal immune cell function, potentially leading to increased risk of infection. Evidence of increased infection risk has been observed with the JAK inhibitor tofacitinib, which is dosed orally for the treatment of rheumatoid arthritis. In asthma, inflammation is localized to the respiratory tract. Inflammation of the airways is characteristic of other respiratory diseases in addition to asthma. Chronic obstructive pulmonary disease (COPD), cystic fibrosis (CF), pneumonitis, interstitial lung diseases (including idiopathic pulmonary fibrosis), acute lung injury, acute respiratory distress syndrome, bronchitis, emphysema, and bronchiolitis obliterans are also respiratory tract diseases in which the pathophysiology is believed to be related to JAK-signaling cytokines. Local administration of a JAK inhibitor to the lungs by inhalation offers the potential to be therapeutically efficacious by delivering a potent anti-cytokine agent directly to the site of action, limiting systemic exposure and therefore limiting the potential for adverse systemic immunosuppression. The need remains for a potent JAK inhibitor suitable for local administration to the lungs for treatment of respiratory disease.

SUMMARY OF THE INVENTION

In one aspect, the invention provides novel compounds having activity as JAK kinase inhibitors.

Accordingly, the invention provides a compound of formula (I):

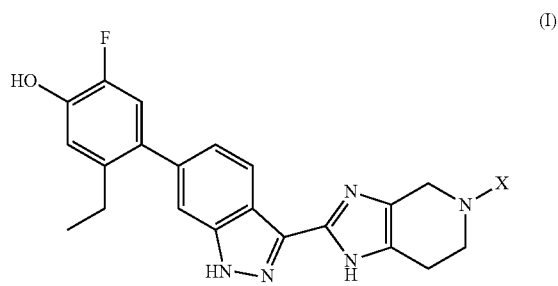

wherein:

X is a group of formula (II):

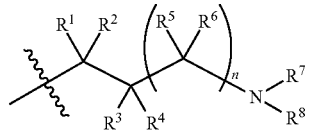

n is 0 or 1;
R¹ is hydrogen or $C_{1-3}$alkyl;
R² is hydrogen or $C_{1-3}$alkyl;
R³ is hydrogen or $C_{1-3}$alkyl;
or R² and R³ taken together form $C_{2-4}$alkylene;
or, when n is 1, R³ is selected from hydrogen, —OH, —OC$_{1-3}$alkyl, halo, —C(O)OC$_{1-3}$alkyl, and $C_{1-3}$alkyl, wherein $C_{1-3}$alkyl is optionally substituted with —OH;
R⁴ is hydrogen or $C_{1-3}$alkyl;
R⁵ is selected from hydrogen, $C_{1-3}$alkyl, —C(O)OC$_{1-3}$alkyl, and phenyl;
or when n is 1, R² and R⁵ taken together form $C_{1-3}$alkylene;
R⁶ is hydrogen or $C_{1-3}$alkyl;
R⁷ is hydrogen or $C_{1-3}$alkyl,
or when n is 0, R² and R⁷ taken together form $C_{1-3}$alkylene, or R⁴ and R⁷ taken together form $C_{2-4}$alkylene or $C_1$alkylene-O—$C_2$alkylene;
or when n is 1, R² and R⁷ taken together form $C_2$alkylene, optionally substituted with $C_{1-3}$alkyl or R$^x$,
or R⁴ and R⁷ taken together form $C_{1-3}$alkylene or —O—$C_2$alkylene;
R⁸ is selected from
(a) hydrogen,
(b) methyl, optionally substituted with —CN, phenyl or $C_{3-6}$cycloalkyl;
(c) $C_{2-6}$alkyl, wherein $C_{2-6}$alkyl is optionally substituted with one or two substituents selected from —OH, —OC$_{1-3}$alkyl, —CN, —SC$_{1-3}$alkyl, phenyl, $C_{3-6}$cycloalkyl, halo, and optionally, in addition with two substituents on a single carbon atom taken together to form $C_{2-3}$alkylene;
(d) $C_{3-6}$cycloalkyl, wherein $C_{3-6}$cycloalkyl is optionally substituted with —OH, —CN, —OC$_{1-3}$alkyl, or $C_{1-3}$alkyl, wherein $C_{1-3}$alkyl is optionally substituted with —OC$_{1-3}$alkyl or with one or two halo,
(e) oxetanyl,
(f) tetrahydropyranyl,
(g) tetrahydrothiophenyl 1,1-dioxide, and
(h) phenyl,
or R⁷ and R⁸ taken together form $C_3$-alkylene or $C_2$alkylene-O—$C_2$alkylene; wherein $C_{3-5}$alkylene is optionally substituted with one or two R$^x$;
R$^x$ is selected from —OH, —CN, —OC$_{1-3}$alkyl, halo, phenyl, and $C_{1-3}$alkyl wherein $C_{1-3}$alkyl is optionally substituted with —OC$_{1-3}$alkyl or —OH, or
two substituents R$^x$ taken together form $C_{1-5}$alkylene or —CH₂OCH₂—,
or when n is 1 and R² and R⁷ taken together form $C_2$alkylene, R⁴ and a substituent R$^x$ on $C_2$alkylene taken together form $C_2$alkylene;
provided that two substituents R$^x$ on the same carbon atom are not both fluoro, and
provided that when R$^x$ is attached to a carbon atom adjacent to a nitrogen atom, R$^x$ is not —OH, —OC$_{1-3}$alkyl, or halo;
or a pharmaceutically-acceptable salt thereof.

As used hereinafter, the phrase "compound of formula (I)" means a compound of formula (I) or a pharmaceutically acceptable salt thereof; i.e., this phrase means a compound of formula (I) in free base form or in a pharmaceutically acceptable salt form unless otherwise indicated.

The invention also provides a pharmaceutical composition comprising a compound of the invention and a pharmaceutically-acceptable carrier.

In another aspect, the invention provides a particular compound of formula (I) as a crystalline free base hydrate. The crystalline hydrate of 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol has been found to have a melting temperature in the range of about 206° C. to about 216° C., typically between about 209° C. and about 214° C., a decomposition onset at about 245° C., and to exhibit weight changes of less than about 0.12% when exposed to a range of relative humidity between about 5% and about 90% at room temperature.

The invention also provides a method of treating respiratory disease, in particular, asthma, in a mammal, the method comprising administering to the mammal a therapeutically effective amount of a compound or of a pharmaceutical composition of the invention. In separate and distinct aspects, the invention also provides synthetic processes and intermediates described herein, which are useful for preparing compounds of the invention.

The invention also provides a compound of the invention as described herein for use in medical therapy, as well as the use of a compound of the invention in the manufacture of a formulation or medicament for treating respiratory disease in a mammal.

BRIEF DESCRIPTION OF THE DRAWINGS

Various aspects of the present invention are illustrated by reference to the accompanying drawings.

DETAILED DESCRIPTION OF THE INVENTION

Figure 1:
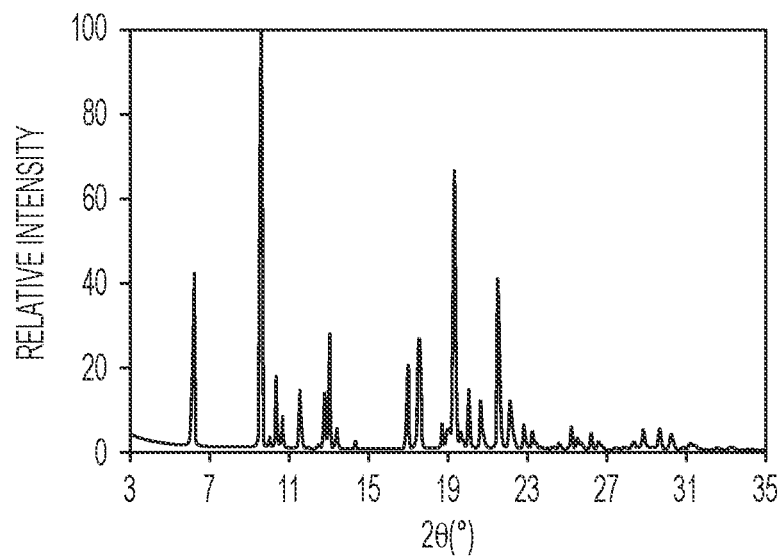
FIG. 1 shows a powder x-ray diffraction (PXRD) pattern of the crystalline hydrate of 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol.

Among other aspects, the invention provides JAK kinase inhibitors of formula (I), pharmaceutically-acceptable salts thereof, and intermediates for the preparation thereof. The following substituents and values are intended to provide representative examples of various aspects of this invention. These representative values are intended to further define such aspects and are not intended to exclude other values or limit the scope of the invention.

In a specific aspect X is a group of formula (II):

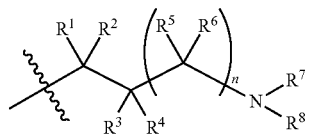

In another specific aspect, X is selected from

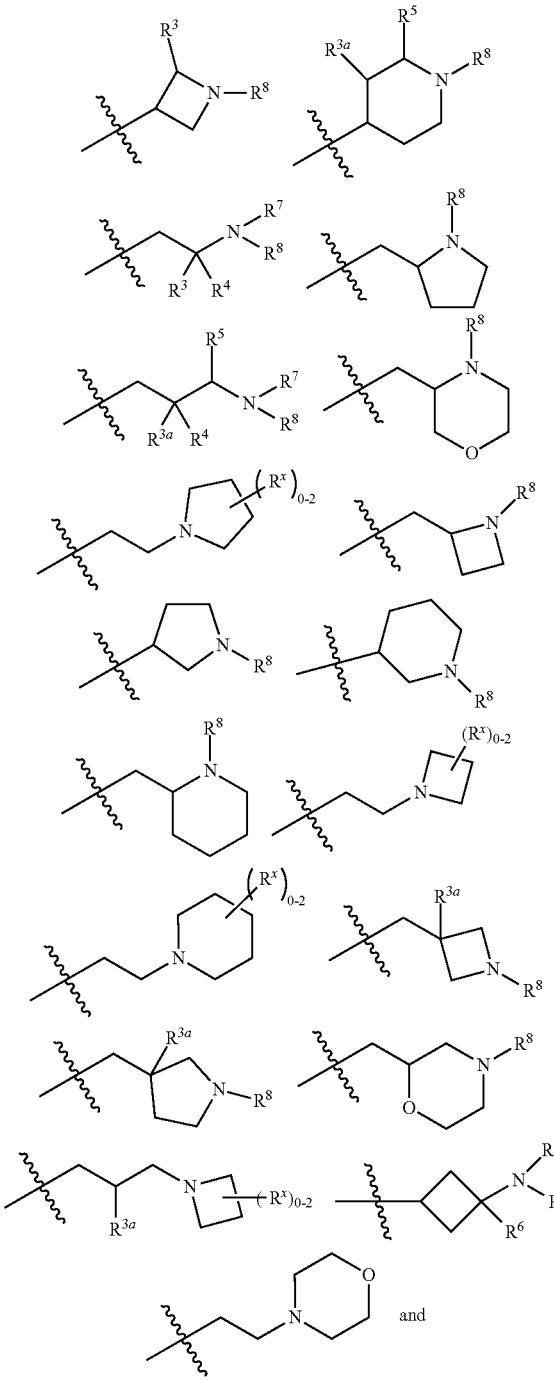

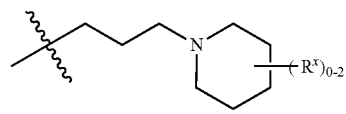

where the variables $R^4$, $R^5$, $R^7$, $R^8$, and $R^x$ are defined as in formula (I) or are defined as hereinbelow, $R^3$ is hydrogen or $C_{1-3}$alkyl, and $R^{3a}$ is selected from hydrogen, —OH, —$OC_{1-3}$alkyl, halo, —$C(O)OC_{1-3}$alkyl, and $C_{1-3}$alkyl, wherein $C_{1-3}$alkyl is optionally substituted with —OH. In another aspect, $R^{3a}$ is selected from hydrogen, —OH, —$OC_{1-3}$alkyl, halo, —$C(O)OC_{1-3}$alkyl, and $C_{1-3}$alkyl, In yet another aspect, X is selected from:

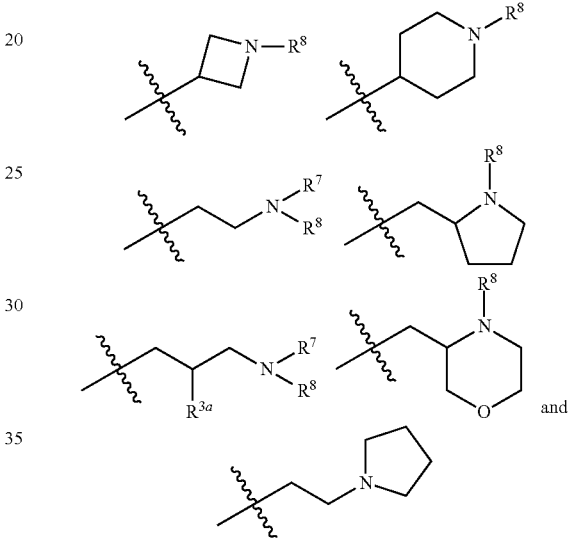

where the variables $R^{3a}$, $R^7$, and $R^8$ are defined as described immediately above or where, in particular, $R^{3a}$ is halo and the pyrrolidine ring of is optionally substituted with $C_{1-3}$alkyl.

In yet another aspect, X is selected from:

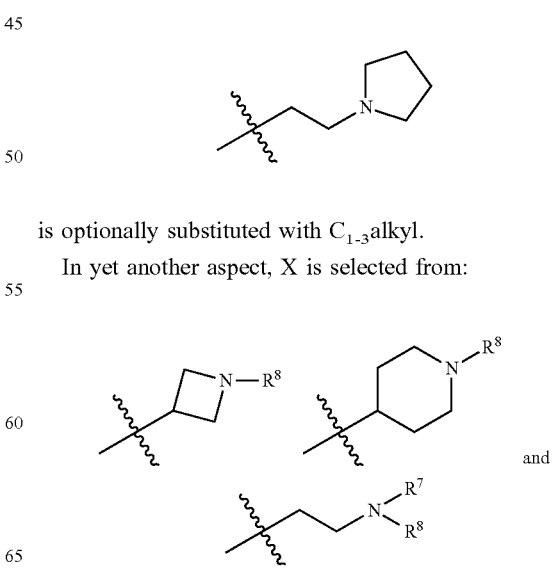

wherein:
R$^7$ is C$_{1-3}$alkyl; and
R$^8$ is selected from hydrogen, methyl, C$_{2-4}$alkyl, C$_{3-4}$cycloalkyl, and

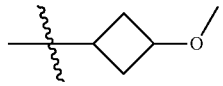

In a specific aspect n is 0 or 1. In another specific aspect, n is 0. In yet another specific aspect, n is 1.

In a specific aspect, R$^1$ is hydrogen or C$_{1-3}$alkyl. In another specific aspect, R$^1$ is hydrogen.

In a specific aspect, R$^2$ is hydrogen or C$_{1-3}$alkyl. In another specific aspect, R$^2$ is hydrogen.

In a specific aspect, R$^3$ is hydrogen or C$_{1-3}$alkyl; or R$^2$ and R$^3$ taken together form C$_{2-4}$alkylene; or, when n is 1, R$^3$ is selected from hydrogen, —OH, —OC$_{1-3}$alkyl, halo, —C(O)OC$_{1-3}$alkyl, and C$_{1-3}$alkyl, wherein C$_{1-3}$alkyl is optionally substituted with —OH;

In another specific aspect, R$^3$ is hydrogen or C$_{1-3}$alkyl; or, when n is 1, R$^3$ is selected from hydrogen, —OH, —OC$_{1-3}$alkyl, halo, —C(O)OC$_{1-3}$alkyl, and C$_{1-3}$alkyl;

In a specific aspect, R$^2$ and R$^3$ taken together form C$_3$alkylene;

Specific values of R$^3$ include hydrogen, —CH$_3$, —OH, —CH$_2$OH, and fluoro.

In a specific aspect, R$^4$ is hydrogen or C$_{1-3}$alkyl. In another specific aspect, R$^4$ is hydrogen.

In a specific aspect, R$^5$ is selected from hydrogen, C$_{1-3}$alkyl, —C(O)OC$_{1-3}$alkyl, and phenyl, or when n is 1, R$^2$ and R$^5$ taken together form C$_{1-3}$alkylene.

In another specific aspect, R$^2$ and R$^5$ taken together form C$_1$alkylene

In another specific aspect, R$^5$ is hydrogen or C$_{1-3}$alkyl. In yet another specific aspect, R$^5$ is hydrogen In a specific aspect, R$^6$ is hydrogen or C$_{1-3}$alkyl. In another specific aspect, R$^6$ is hydrogen.

In a specific aspect, R$^7$ is hydrogen or C$_{1-3}$alkyl or when n is 0, R$^2$ and R$^7$ taken together form C$_{1-3}$alkylene, or R$^4$ and R$^7$ taken together form C$_{2-4}$alkylene or C$_1$alkylene-O—C$_2$alkylene; or when n is 1, R$^2$ and R$^7$ taken together form C$_2$alkylene, optionally substituted with C$_{1-3}$alkyl, or R$^4$ and R$^7$ taken together form C$_{1-3}$alkylene or —O—C$_2$alkylene. In another specific aspect, when n is 1, R$^4$ and R$^7$ taken together form —O—C$_2$alkylene.

In another specific aspect, R$^7$ is hydrogen or C$_{1-3}$alkyl.

In a specific aspect, R$^8$ is selected from (a) hydrogen, (b) methyl, optionally substituted with —CN, phenyl or C$_{3-6}$cycloalkyl; (c) C$_{2-6}$alkyl, wherein C$_{2-6}$alkyl is optionally substituted with one or two substituents selected from —OH, —OC$_{1-3}$alkyl, —CN, —SC$_{1-3}$alkyl, phenyl, C$_{3-6}$cycloalkyl, halo, and optionally, in addition with two substituents on a single carbon atom taken together to form C$_{2-3}$alkylene; (d) C$_{3-6}$cycloalkyl, wherein C$_{3-6}$cycloalkyl is optionally substituted with —OH, —CN, —OC$_{1-3}$alkyl, or C$_{1-3}$alkyl, wherein C$_{1-3}$alkyl is optionally substituted with —OC$_{1-3}$alkyl or with one or two halo, (e) oxetanyl, (f) tetrahydropyranyl, (g) tetrahydrothiophenyl 1,1-dioxide, and (h) phenyl; or R$^7$ and R$^8$ taken together form C$_{3-5}$alkylene or C$_2$alkylene-O—C$_2$alkylene.

In another specific aspect, R$^8$ is selected from (a) hydrogen, (b) methyl, optionally substituted with C$_{3-6}$cycloalkyl; (c) C$_{2-4}$alkyl, wherein C$_{2-4}$alkyl is optionally substituted with one substituent selected from —OH, —OC$_{1-3}$alkyl, —CN, —SC$_{1-3}$alkyl, C$_{3-4}$cycloalkyl, and halo and optionally, in addition, with two substituents on a single carbon atom taken together to form C$_2$alkylene; (d) C$_{3-4}$cycloalkyl, wherein C$_{3-4}$cycloalkyl is optionally substituted with —OH, —CN, —OC$_{1-3}$alkyl, or C$_{1-3}$alkyl, wherein C$_{1-3}$alkyl is optionally substituted with —OC$_{1-3}$alkyl or with one or two halo; (e) oxetanyl; (f) tetrahydropyranyl; and (g) tetrahydrothiophenyl 1,1-dioxide.

Specific values of R$^8$ include hydrogen, —CH$_3$, —C$_2$H$_5$, isopropyl, cyclopropyl, cyclobutyl, —CH(CH$_3$)C$_2$H$_5$, —(CH$_2$)$_2$CN, —CH$_2$CH$_2$F, —CH$_2$isopropyl —CH$_2$cyclopropyl, —(CH$_2$)$_2$OH, (CH$_2$)$_{2-3}$OCH$_3$, —(CH$_2$)$_{2-3}$SCH$_3$, —(CH$_2$)$_2$CH(CH$_3$)SCH$_3$, tetrahydropyran-4-yl, pyridin-4-yl,

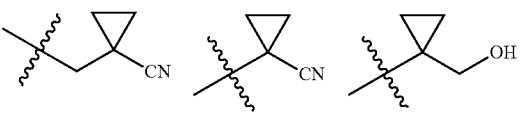

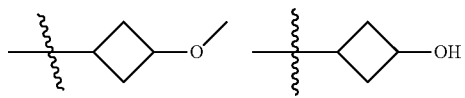

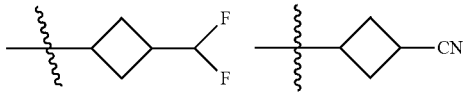

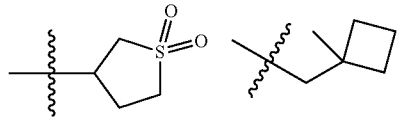

In other specific aspects, R$^8$ is selected from hydrogen, methyl, C$_{2-4}$alkyl, C$_{3-4}$cycloalkyl, and

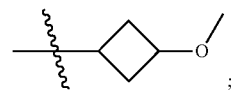 [SMILES: *C1CC(OC)C1]

;

and hydrogen, methyl, C$_{2-4}$alkyl and

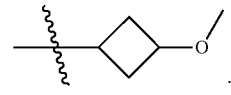 [SMILES: *C1CC(OC)C1]

.

In yet another specific aspect, R$^8$ is selected from hydrogen, methyl, C$_{2-4}$alkyl, and C$_{3-4}$cycloalkyl, or hydrogen, methyl, C$_{2-4}$alkyl and C$_3$cycloalkyl.

In a certain aspect, the invention provides compounds of formula (III):

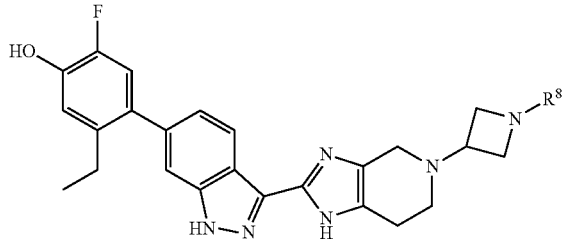

wherein the variable R⁸ is as defined herein.

In another aspect, the invention provides compounds of formula (IV):

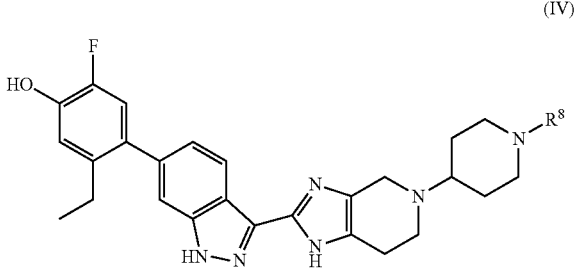

wherein the variable R⁸ is as defined herein.

In yet another aspect, the invention provides compounds of formula (V):

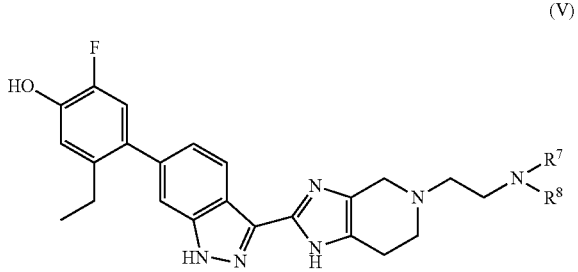

wherein the variables R⁷ and R⁸ are as defined herein.

In another aspect, the invention provides a compound selected from the following compounds 5-ethyl-2-fluoro-4-(3-(5-(1-methylazetidin-3-yl)-4,5,6,7-tetrahydro-1H-imidazo[4,5-c]pyridin-2-yl)-1H-indazol-6-yl)phenol,
4-(3-(5-(azetidin-3-yl)-4,5,6,7-tetrahydro-1H-imidazo[4,5-c]pyridin-2-yl)-1H-indazol-6-yl)-5-ethyl-2-fluorophenol,
5-ethyl-2-fluoro-4-(3-(5-(1-isopropylazetidin-3-yl)-4,5,6,7-tetrahydro-1H-imidazo[4,5-c]pyridin-2-yl)-1H-indazol-6-yl)phenol,
4-(3-(5-(1-(sec-butyl)azetidin-3-yl)-4,5,6,7-tetrahydro-1H-imidazo[4,5-c]pyridin-2-yl)-1H-indazol-6-yl)-5-ethyl-2-fluorophenol,
4-(3-(5-(1-cyclopropylazetidin-3-yl)-4,5,6,7-tetrahydro-1H-imidazo[4,5-c]pyridin-2-yl)-1H-indazol-6-yl)-5-ethyl-2-fluorophenol,
5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol,
4-(3-(5-(2-(dimethylamino)ethyl)-4,5,6,7-tetrahydro-1H-imidazo[4,5-c]pyridin-2-yl)-1H-indazol-6-yl)-5-ethyl-2-fluorophenol,
5-ethyl-2-fluoro-4-(3-(5-(2-((3-methoxycyclobutyl)amino)ethyl)-4,5,6,7-tetrahydro-1H-imidazo[4,5-c]pyridin-2-yl)-1H-indazol-6-yl)phenol,
5-ethyl-4-(3-(5-(2-(ethyl(methyl)amino)ethyl)-4,5,6,7-tetrahydro-1H-imidazo[4,5-c]pyridin-2-yl)-1H-indazol-6-yl)-2-fluorophenol,
4-(3-(5-(2-(sec-butyl(methyl)amino)ethyl)-4,5,6,7-tetrahydro-1H-imidazo[4,5-c]pyridin-2-yl)-1H-indazol-6-yl)-5-ethyl-2-fluorophenol,
(S)-5-ethyl-2-fluoro-4-(3-(5-((1-methylpyrrolidin-2-yl)methyl)-4,5,6,7-tetrahydro-1H-imidazo[4,5-c]pyridin-2-yl)-1H-indazol-6-yl)phenol,
4-(3-(5-(3-(dimethylamino)-2-fluoropropyl)-4,5,6,7-tetrahydro-1H-imidazo[4,5-c]pyridin-2-yl)-1H-indazol-6-yl)-5-ethyl-2-fluorophenol,
(S)-5-ethyl-2-fluoro-4-(3-(5-(morpholin-3-ylmethyl)-4,5,6,7-tetrahydro-1H-imidazo[4,5-c]pyridin-2-yl)-1H-indazol-6-yl)phenol,
(R)-5-ethyl-2-fluoro-4-(3-(5-(morpholin-3-ylmethyl)-4,5,6,7-tetrahydro-1H-imidazo[4,5-c]pyridin-2-yl)-1H-indazol-6-yl)phenol,
(S)-5-ethyl-2-fluoro-4-(3-(5-(2-(2-methylpyrrolidin-1-yl)ethyl)-4,5,6,7-tetrahydro-1H-imidazo[4,5-c]pyridin-2-yl)-1H-indazol-6-yl)phenol,
and pharmaceutically-acceptable salts thereof.

In one aspect, the invention provides the compounds of Examples 1-18 and Tables 1-19 below.

In a specific aspect, the invention provides the compounds 3-19, 3-28, and 3-29, disclosed in Table 3 that are not included in formula (I).

Chemical structures are named herein according to IUPAC conventions as implemented in ChemDraw software (PerkinElmer, Inc., Cambridge, Mass.). For example, the compound of Example 1:

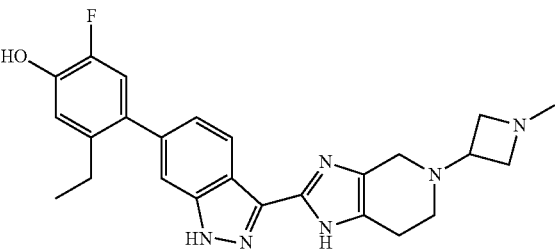 [SMILES: CCc1cc(O)c(F)cc1-c1ccc2c(-c3nc4c([nH]3)CCN(C3CN(C)C3)C4)n[nH]c2c1]

is designated as 5-ethyl-2-fluoro-4-(3-(5-(1-methylazetidin-3-yl)-4,5,6,7-tetrahydro-H-imidazo[4,5-c]pyridin-2-yl)-1H-indazol-6-yl)phenol.

Furthermore, the imidazo portion of the tetrahydroimidazopyridine moiety in the structure of formula (I) exists in tautomeric forms, illustrated below for a fragment of the compound of Example 1

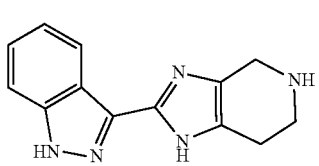

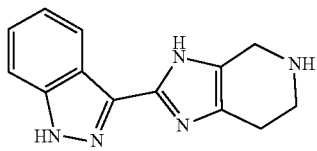

B

According to the IUPAC convention, these representations give rise to different numbering of the atoms of the imidazole portion: 2-(1H-indazol-3-yl)-4,5,6,7-tetrahydro-1H-imidazo[4,5-c]pyridine (structure A) vs. 2-(1H-indazol-3-yl)-4,5,6,7-tetrahydro-3H-imidazo[4,5-c]pyridine (structure B). It will be understood that although structures are shown, or named, in a particular form, the invention also includes the tautomer thereof.

The compounds of the invention may contain one or more chiral centers and therefore, such compounds (and intermediates thereof) can exist as racemic mixtures; pure stereoisomers (i.e., enantiomers or diastereomers); stereoisomer-enriched mixtures and the like. Chiral compounds shown or named herein without a defined stereochemistry at a chiral center are intended to include any or all possible stereoisomer variations at the undefined stereocenter unless otherwise indicated. The depiction or naming of a particular stereoisomer means the indicated stereocenter has the designated stereochemistry with the understanding that minor amounts of other stereoisomers may also be present unless otherwise indicated, provided that the utility of the depicted or named compound is not eliminated by the presence of another stereoisomer.

Compounds of formula (I) also contain several basic groups (e.g., amino groups) and therefore, such compounds can exist as the free base or in various salt forms, such a mono-protonated salt form, a di-protonated salt form, a tri-protonated salt form, or mixtures thereof. All such forms are included within the scope of this invention, unless otherwise indicated.

This invention also includes isotopically-labeled compounds of formula (I), i.e., compounds of formula (I) where an atom has been replaced or enriched with an atom having the same atomic number but an atomic mass different from the atomic mass that predominates in nature. Examples of isotopes that may be incorporated into a compound of formula (I) include, but are not limited to, $^2$H, $^3$H, $^{11}$C, $^{13}$C, $^{14}$C, $^{13}$N, $^{15}$N, $^{15}$O, $^{17}$O, $^{18}$O, $^{35}$S $^{36}$Cl, and $^{18}$F. Of particular interest are compounds of formula (I) enriched in tritium or carbon-14, which compounds can be used, for example, in tissue distribution studies. Also of particular interest are compounds of formula (I) enriched in deuterium especially at a site of metabolism, which compounds are expected to have greater metabolic stability. Additionally of particular interest are compounds of formula (I) enriched in a positron emitting isotope, such as $^{11}$C, $^{18}$F, $^{15}$O and $^{13}$N, which compounds can be used, for example, in Positron Emission Tomography (PET) studies.

Definitions

When describing this invention including its various aspects and embodiments, the following terms have the following meanings, unless otherwise indicated.

The term "alkyl" means a monovalent saturated hydrocarbon group which may be linear or branched or combinations thereof. Unless otherwise defined, such alkyl groups typically contain from 1 to 10 carbon atoms. Representative alkyl groups include, by way of example, methyl (Me), ethyl (Et), n-propyl (n-Pr) or (nPr), isopropyl (i-Pr) or (iPr), n-butyl (n-Bu) or (nBu), sec-butyl, isobutyl, tert-butyl (t-Bu) or (tBu), n-pentyl, n-hexyl, 2,2-dimethylpropyl, 2-methylbutyl, 3-methylbutyl, 2-ethylbutyl, 2,2-dimethylpentyl, 2-propylpentyl, and the like.

The term "alkylene" means a divalent saturated hydrocarbon group which may be linear or branched or combinations thereof. Unless otherwise defined, such alkyl groups typically contain from 1 to 10 carbon atoms. Representative alkylene groups include, by way of example —CH$_2$—, —CH$_2$CH$_2$—, —CH$_2$CH$_2$CH$_2$—, and the like.

When a specific number of carbon atoms are intended for a particular term, the number of carbon atoms is shown preceding the term. For example, the term "C$_{1-3}$ alkyl" means an alkyl group having from 1 to 3 carbon atoms wherein the carbon atoms are in any chemically-acceptable configuration, including linear or branched configurations.

The term "cycloalkyl" means a monovalent saturated carbocyclic group which may be monocyclic or multicyclic. Unless otherwise defined, such cycloalkyl groups typically contain from 3 to 10 carbon atoms. Representative cycloalkyl groups include, by way of example, cyclopropyl (cPr), cyclobutyl (cBu), cyclopentyl, cyclohexyl, cycloheptyl, cyclooctyl, adamantyl, and the like.

The term "heterocycle", "heterocyclic", or "heterocyclic ring" means a monovalent saturated or partially unsaturated cyclic non-aromatic group, having from 3 to 10 total ring atoms, wherein the ring contains from 2 to 9 carbon ring atoms and from 1 to 4 ring heteroatoms selected from nitrogen, oxygen, and sulfur. Heterocyclic groups may be monocyclic or multicyclic (i.e., fused or bridged). Representative heterocyclic groups include, by way of example, pyrrolidinyl, piperidinyl, piperazinyl, imidazolidinyl, morpholinyl, thiomorpholyl, indolin-3-yl, 2-imidazolinyl, tetrahydropyranyl, 1,2,3,4-tetrahydroisoquinolin-2-yl, quinuclidinyl, 7-azanorbornanyl, nortropanyl, and the like, where the point of attachment is at any available carbon or nitrogen ring atom. Where the context makes the point of attachment of the heterocyclic group evident, such groups may alternatively be referred to as a non-valent species, i.e. pyrrolidine, piperidine, piperazine, imidazole, tetrahydropyran etc.

The term "halo" means fluoro, chloro, bromo or iodo.

The term "solvate" means a complex or aggregate formed by one or more molecules of a solute, i.e. a compound of the invention or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is specifically termed a hydrate.

The term "therapeutically effective amount" means an amount sufficient to effect treatment when administered to a patient in need of treatment.

The term "treatment" as used herein means the treatment of a disease, disorder, or medical condition (such as a respiratory disease), in a patient, such as a mammal (particularly a human) which includes one or more of the following:

(a) preventing the disease, disorder, or medical condition from occurring, i.e., preventing the reoccurrence of the disease or medical condition or prophylactic treatment of a patient that is pre-disposed to the disease or medical condition;

(b) ameliorating the disease, disorder, or medical condition, i.e., eliminating or causing regression of the disease, disorder, or medical condition in a patient, including counteracting the effects of other therapeutic agents;

(c) suppressing the disease, disorder, or medical condition, i.e., slowing or arresting the development of the disease, disorder, or medical condition in a patient; or (d) alleviating the symptoms of the disease, disorder, or medical condition in a patient.

The term "pharmaceutically acceptable salt" means a salt that is acceptable for administration to a patient or a mammal, such as a human (e.g., salts having acceptable mammalian safety for a given dosage regime). Representative pharmaceutically acceptable salts include salts of acetic, ascorbic, benzenesulfonic, benzoic, camphorsulfonic, citric, ethanesulfonic, edisylic, fumaric, gentisic, gluconic, glucoronic, glutamic, hippuric, hydrobromic, hydrochloric, isethionic, lactic, lactobionic, maleic, malic, mandelic, methanesulfonic, mucic, naphthalenesulfonic, naphthalene-1,5-disulfonic, naphthalene-2,6-disulfonic, nicotinic, nitric, orotic, pamoic, pantothenic, phosphoric, succinic, sulfuric, tartaric, p-toluenesulfonic and xinafoic acid, and the like.

The term "salt thereof" means a compound formed when the hydrogen of an acid is replaced by a cation, such as a metal cation or an organic cation and the like. For example, the cation can be a protonated form of a compound of formula (I), i.e. a form where one or more amino groups have been protonated by an acid. Typically, the salt is a pharmaceutically acceptable salt, although this is not required for salts of intermediate compounds that are not intended for administration to a patient.

The term "amino-protecting group" means a protecting group suitable for preventing undesired reactions at an amino nitrogen. Representative amino-protecting groups include, but are not limited to, formyl; acyl groups, for example alkanoyl groups, such as acetyl and tri-fluoroacetyl; alkoxycarbonyl groups, such as tert butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS), tert-butyldimethylsilyl (TBDMS), [2-(trimethylsilyl)ethoxy]methyl (SEM); and the like. Numerous protecting groups, and their introduction and removal, are described in T. W. Greene and P. G. M. Wuts, *Protecting Groups in Organic Synthesis*, Third Edition, Wiley, New York General Synthetic Procedures Compounds of this invention, and intermediates thereof, can be prepared according to the following general methods and procedures using commercially-available or routinely-prepared starting materials and reagents. The substituents and variables (e.g., $R^1$, $R^2$, $R^3$, $R^4$, etc.) used in the following schemes have the same meanings as those defined elsewhere herein unless otherwise indicated. Additionally, compounds having an acidic or basic atom or functional group may be used or may be produced as a salt unless otherwise indicated (in some cases, the use of a salt in a particular reaction will require conversion of the salt to a non-salt form, e.g., a free base, using routine procedures before conducting the reaction).

Although a particular embodiment of the present invention may be shown or described in the following procedures, those skilled in the art will recognize that other embodiments or aspects of the present invention can also be prepared using such procedures or by using other methods, reagents, and starting materials know to those skilled in the art. In particular, it will be appreciated that compounds of the invention may be prepared by a variety of process routes in which reactants are combined in different orders to provide different intermediates en route to producing final products.

A general method of preparing final compounds of the invention utilizes a key intermediate 1 as illustrated in Scheme 1. The variables $R^2$, $R^3$, $R^4$, and $R^7$ are defined as in formula (I), $R^1$ is hydrogen, Pg represents an amino protecting group, typically Boc, and $R^{8a}$ and $R^{8b}$ are defined so that the group $R^8$ is formed upon completion of the reaction, i.e. $R^{8a}$—C(H)—$R^{8b}$ is $R^8$. For example, when $R^8$ is methyl, the variables $R^{8a}$ and $R^{8b}$ are each hydrogen such that $R^{8a}$—C(=O)—$R^{8b}$ is formaldehyde. For $R^8$ defined as isopropyl, $R^{8a}$ and $R^{8b}$ are each methyl such that $R^{8a}$—C(=O)—$R^{8b}$ is acetone.

Scheme 1

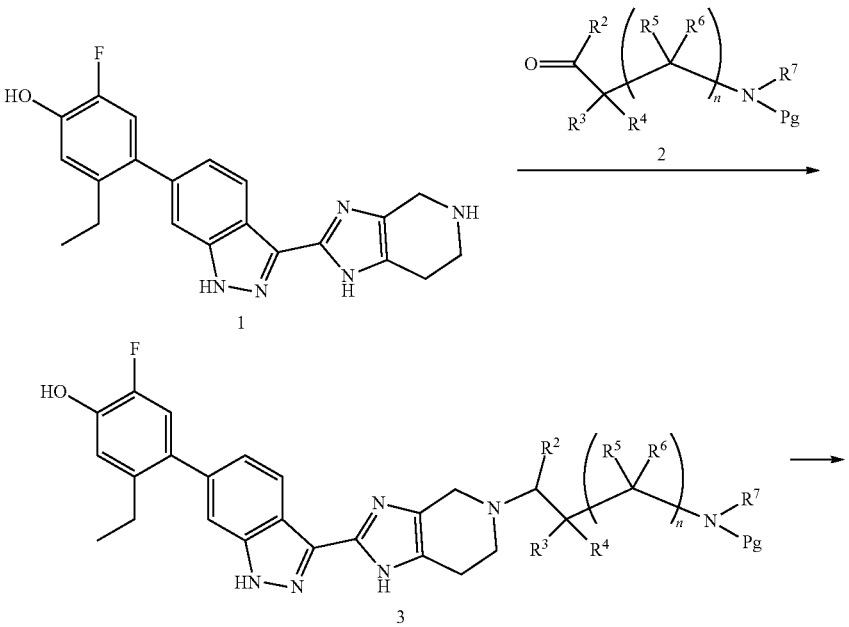

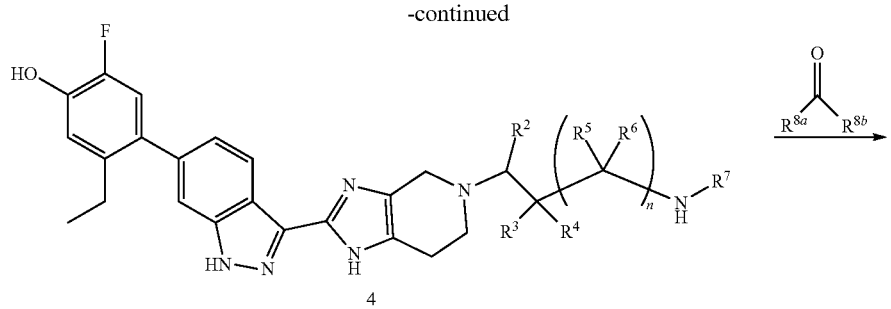

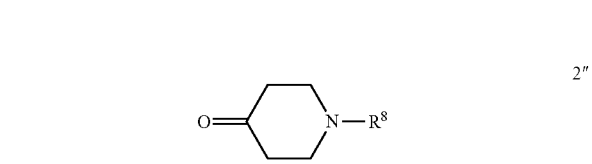

In Scheme 1, intermediate 1 is reductively N-alkylated by reaction with the aldehyde or ketone 2 to provide the protected intermediate 3. The reaction is typically conducted by contacting intermediate 1 with between about 1 and about 2 equivalents of compound 2 in a suitable inert diluent, such as dichloromethane, methanol, tetrahydrofuran, or dimethylformamide in the presence of between about 2 and about 4 equivalents of a reducing agent. Between about 2 and about 3 equivalents of acetic acid may optionally be included in the reaction. The reaction is typically conducted at a temperature in the range of about 20° C. to about 40° C. for about 2 to about 48 hours or until the reaction is substantially complete. Typical reducing agents include sodium triacetoxyborohydride and sodium cyanoborohydride.

The protecting group is removed from intermediate 3 under typical conditions. For example, a Boc group may be removed by standard treatment with an acid, typically trifluoroacetic acid or hydrochloric acid in dioxane to provide intermediate 4 which is reacted with a compound of the formula $R^{8a}$—C(=O)—$R^{8b}$ under similar reductive alkylation conditions as in the first step to provide a final compound (I)'.

For compounds in which the group of formula (II) includes a tertiary nitrogen, for example, where $R^7$ and $R^8$ taken together form $C_{3-5}$alkylene or $C_2$alkylene-O—$C_2$alkylene, final compounds may be directly prepared by a reaction of intermediate 1 with an intermediate 2'

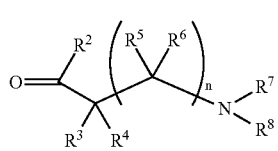

in which the amino protecting group Pg of the compound of formula 2 is replaced by $R^8$. For example, as illustrated in Examples 6 and 17 below, final compounds of formula (IV) may be prepared by reaction of intermediate 1 with a compound of formula 2":

A useful process for the preparation of intermediate 1 is illustrated in Scheme 2.

Scheme 2

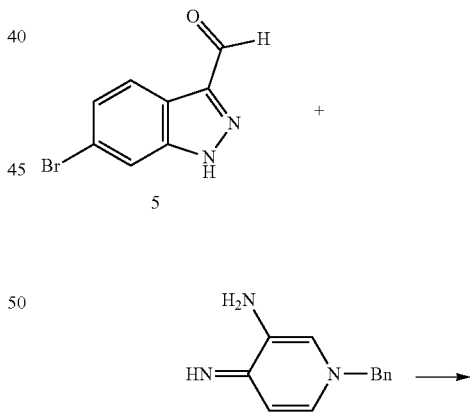

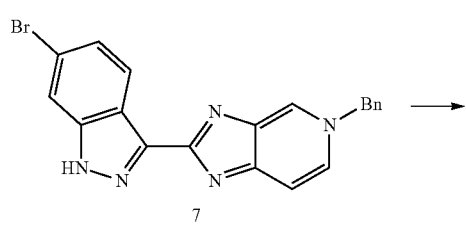

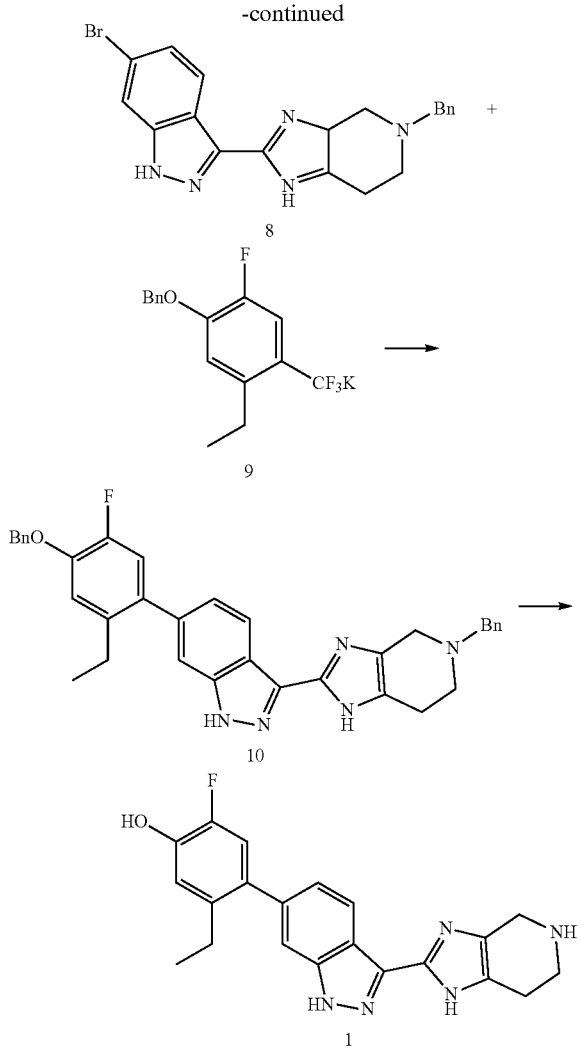

As described in detail in Preparations 9 and 10, and also 13 and 14, below, the bromoindazole aldehyde 5 is reacted with the benzyl protected imine compound 6 to provide intermediate 7. The reaction is typically conducted in the presence of sodium bisulfite, at a temperature of between about 130° C. and about 140° C. for between about 1 and about 6 hours or until the reaction is substantially complete. The product may be isolated by precipitation from the reaction mixture followed by freebasing and recrystallization. Compound 7 is reduced using a reducing agent such as sodium borohydride to provide compound 8. The reaction is beneficially performed in a diluent composed of methyltetrahydrofuran, methanol, and water.

Isolation of the product 8 as a freebase or as a hydrochloride salt provides a product of excellent purity. Intermediate 8 is combined with protected phenyltrifluoroborate 9 under typical Suzuki-Miyaura coupling conditions to provide intermediate 10. The reaction is typically conducted at elevated temperature in the presence of a palladium catalyst. Optionally, the Suzuki coupling reaction is promoted by the inclusion of an additional agent prepared by the reaction of bis(pinacolato)boron with potassium hydrogen difluoride, as described in Preparation 16. Finally, the benzyl groups of intermediate 10 are removed under typical conditions, for example in a hydrogen atmosphere in the presence of a palladium catalyst, to provide intermediate 1.

The imine compound 6 used in the first step of Scheme 2 is conveniently prepared by reacting a pyridine diamine with benzyl bromide and is supplied as the hydrobromide salt. As described in Preparation 8, the Suzuki partner 9, shown in Scheme 2 as the trifluoroborate potassium salt can be prepared by benzyl protecting 4-bromo-5-ethyl-2-fluorophenol by reaction with benzyl bromide and reacting the benzyl protected phenol with bis(pinacolato)diboron to prepare the boronate which is subsequently reacted with potassium hydrogen difluoride to provide intermediate 9. Alternatively, a boronate intermediate can be used in place of the trifluoroborate 9.

Accordingly, in a method aspect, the invention provides a process of preparing a compound of formula (I') or a pharmaceutically acceptable salt thereof, the process comprising (a) reacting a compound of formula 1 with a compound of formula 2 to provide an intermediate of formula 3, (b) deprotecting intermediate 3 to provide intermediate 4, and (c) reacting intermediate 4 with $R^{8a}$—C(=O)—$R^{8b}$ to provide a compound of formula (I') or a pharmaceutically acceptable salt thereof. The invention further provides a process of preparing a compound of formula (IV) or a pharmaceutically-acceptable salt thereof, the process comprising reacting a compound of formula 1 with a compound of formula 2" to provide a compound of formula (IV) or a pharmaceutically acceptable salt thereof.

In a further method aspect, the invention provides a process of preparing a compound of formula 1, the process comprising (a) reacting a compound of formula 8 with a compound of formula 9 to provide a compound of formula 10, and (b) deprotecting the compound of formula 10 to provide a compound of formula 1.

In yet another aspect, the invention provides a compound of formula 8 and a hydrochloride salt thereof useful in the preparation of intermediate 1.

Crystalline Form

In another aspect, the invention provides the crystalline hydrate of 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol The crystalline hydrate of the invention is a crystalline freebase of the compound of Example 6. In one aspect, the crystalline hydrate is characterized by a powder X-ray diffraction (PXRD) pattern having significant diffraction peaks, among other peaks, at 2θ values of 6.20±0.20, 9.58±0.20, 17.53±0.20, 19.28±0.20, and 21.51±0.20. The crystalline hydrate may be further characterized by a PXRD pattern having two or more additional diffraction peaks, including three or more and four or more additional diffraction peaks at 2θ values selected from 10.34±0.20, 11.54±0.20, 12.77±0.20, 13.01±0.20, 16.94±0.20, 20.61±0.20, and 22.10±0.20. In another aspect, the crystalline hydrate is characterized by a PXRD pattern having diffraction peaks at 2θ values of 6.20±0.20, 9.58±0.20, 10.34±0.20, 11.54±0.20, 12.77±0.20, 13.01±0.20, 16.94±0.20, 17.53±0.20, 19.28±0.20, 20.61±0.20, 21.51±0.20, and 22.10±0.20.

As is well known in the field of powder X-ray diffraction, peak positions of PXRD spectra are relatively less sensitive to experimental details, such as details of sample preparation and instrument geometry, than are the relative peak heights. Thus, in one aspect, the crystalline hydrate is characterized by a powder x-ray diffraction pattern in which the peak positions are substantially in accordance with those shown in FIG. 1.

Figure 2:
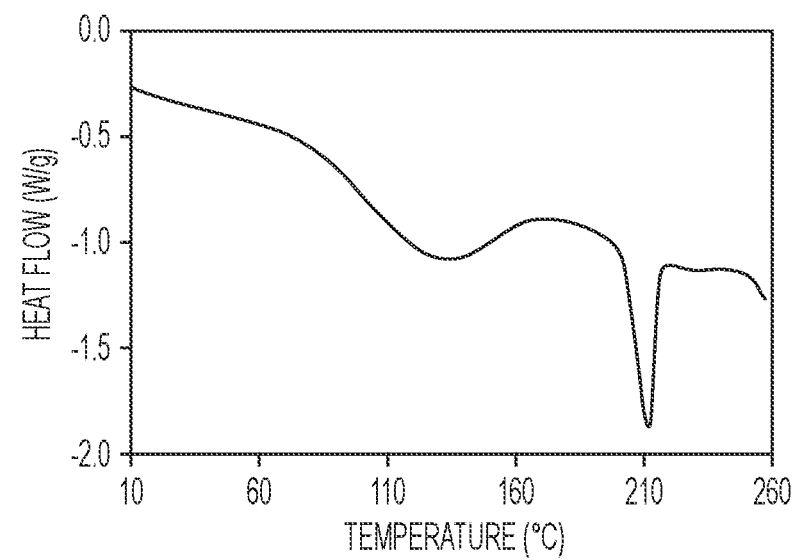
FIG. 2 shows a differential scanning calorimetry (DSC) thermogram of the crystalline hydrate of 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol.
Figure 3:
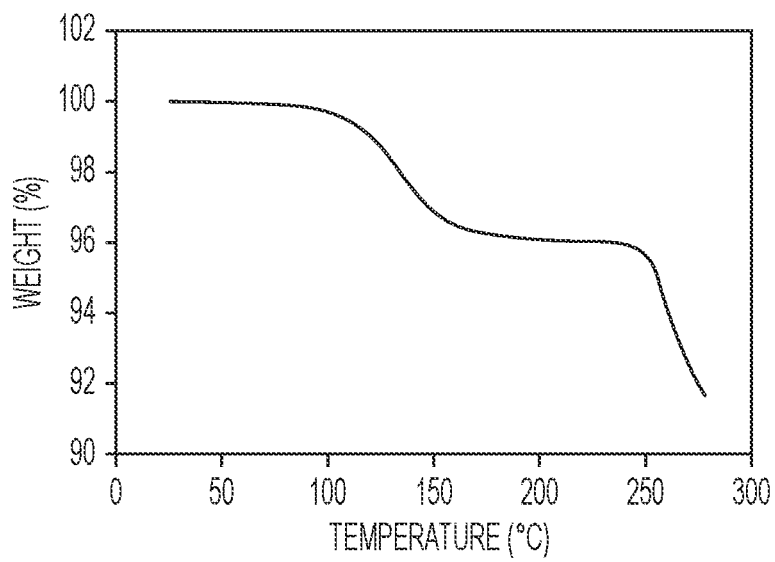
FIG. 3 shows a thermal gravimetric analysis (TGA) plot of the crystalline hydrate of 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol.

In another aspect, the crystalline hydrate is characterized by its behavior when exposed to high temperature. As demonstrated in FIG. 2, the differential scanning calorimetry (DSC) trace recorded at a heating rate of 10° C. per minute exhibits a desolvation endotherm with an onset at about 83° C. and a peak at about 128° C. and a peak in endothermic heat flow, identified as a melt transition, in the range of about 206° C. to about 216° C., including between about 209° C. and about 214° C. The thermal gravimetric analysis (TGA) trace of FIG. 3 shows a desolvation onset at a temperature of about 112° C. and a decomposition onset at a temperature of about 250° C. The TGA profile shows a weight loss of about 3.86% at 190° C. which may be interpreted as the loss of water and compared with the theoretical weight percentage of water for a monohydrate of 3.65%. Accordingly it is believed the present crystalline hydrate is a monohydrate.

Figure 4:
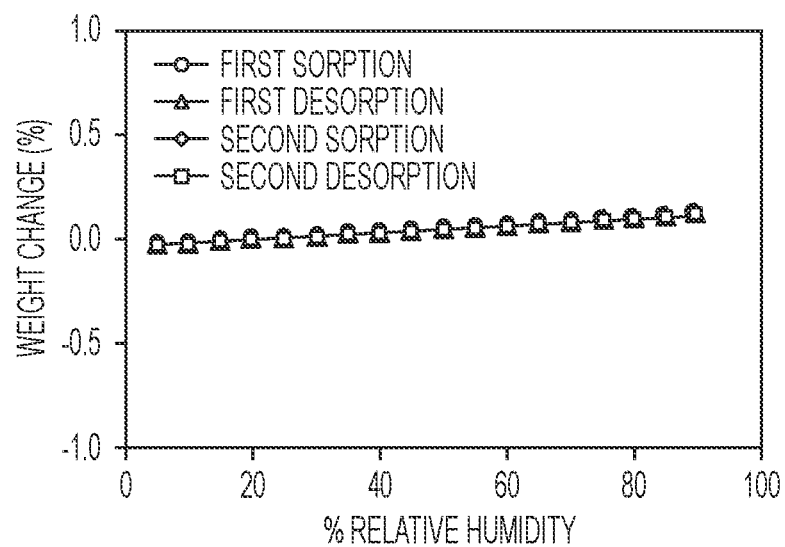
FIG. 4 shows a dynamic moisture sorption (DMS) isotherm of the crystalline hydrate of 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol observed at a temperature of about 25° C.

The present crystalline hydrate has been demonstrated to have a reversible sorption/desorption profile with an exceptionally small propensity for hygroscopicity. Form I demonstrated less than about 0.12% weight gain in the humidity range of 5% to 90% relative humidity as shown in FIG. 4. No hysteresis was observed in two cycles of sorption and desorption. The crystalline hydrate is considered to be non-hygroscopic.

The crystalline hydrate of 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol is conveniently prepared by a slurry form conversion of a slurry of the reaction product of the reductive N-alkylation reaction of the intermediate of formula 1 with 1-methylpiperidin-4-one. After an initial quench of the reductive N-alkylation reaction with ammonia in water, the resulting slurry is diluted in a protic solvent, for example methanol, ethanol, isopropyl alcohol, or n-propyl alcohol, and heated at a temperature of from about 40° C. to about 60° C. for between about 1 and about 24 hours or until conversion to a solvate form is complete. While hot, water is added as an antisolvent to precipitate a solvate of the reaction product, which is cooled, for example, to about 10° C. The precipitate is washed with a 1:1 mixture of water with the protic solvent. Typically, the solvate includes the diluent in which the reductive alkylation reaction was performed, the protic solvent, and water.

The slurry form conversion to the crystalline hydrate of the invention is performed by forming a slurry of either the solvate formed as described above or of amorphous 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol in a diluent including from about 1 to about 30% v/v water along with an organic solvent. Useful organic solvents for the form conversion include, but are not limited to methanol, tetrahydrofuran, tert-butyl alcohol, acetonitrile, isopropylacetate and acetone. The form conversion optionally includes heating, for example heating at from about 40° C. to about 60° C. for between about 1 hour and about 2 days or until the form conversion is complete. As described in Example 17, methanol is useful as the protic solvent in the initial step while acetone is particularly useful for the slurry form conversion.

Accordingly in a method aspect, the invention provides a method of preparing the crystalline hydrate of 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol, the method comprising (a) forming a slurry of 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol in solvate or amorphous form in a diluent including from about 1 to about 30% v/v water along with an organic solvent selected from methanol, tetrahydrofuran, tert-butyl alcohol, acetonitrile, isopropylacetate and acetone, (b) heating the slurry at a temperature between about 40° C. and about 60° C. for between about 1 hour and about 2 days, and (c) isolating the crystalline hydrate from the slurry.

Pharmaceutical Compositions

The compounds of the invention and pharmaceutically-acceptable salts thereof are typically used in the form of a pharmaceutical composition or formulation. Such pharmaceutical compositions may advantageously be administered to a patient by inhalation. In addition, pharmaceutical compositions may be administered by any acceptable route of administration including, but not limited to, oral, rectal, nasal, topical (including transdermal) and parenteral modes of administration.

Accordingly, in one of its compositions aspects, the invention is directed to a pharmaceutical composition comprising a pharmaceutically-acceptable carrier or excipient and a compound of formula (I), where, as defined above, "compound of formula (I)" means a compound of formula (I) or a pharmaceutically-acceptable salt thereof. Optionally, such pharmaceutical compositions may contain other therapeutic and/or formulating agents if desired. When discussing compositions and uses thereof, the "compound of the invention" may also be referred to herein as the "active agent". As used herein, the term "compound of the invention" is intended to include all compounds encompassed by formula (I) as well as the species embodied in formulas (III), (IV), and (V) and pharmaceutically-acceptable salts thereof.

The pharmaceutical compositions of the invention typically contain a therapeutically effective amount of a compound of the present invention. Those skilled in the art will recognize, however, that a pharmaceutical composition may contain more than a therapeutically effective amount, i.e., bulk compositions, or less than a therapeutically effective amount, i.e., individual unit doses designed for multiple administration to achieve a therapeutically effective amount.

Typically, such pharmaceutical compositions will contain from about 0.01 to about 95% by weight of the active agent; including, for example, from about 0.05 to about 30% by weight; and from about 0.1% to about 10% by weight of the active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the carriers or excipients used in the pharmaceutical compositions of this invention are commercially-available. By way of further illustration, conventional formulation techniques are described in Remington: The Science and Practice of Pharmacy, 20th Edition, Lippincott Williams & White, Baltimore, Md. (2000); and H. C. Ansel et al., Pharmaceutical Dosage Forms and Drug Delivery Systems, 7th Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical compositions.

Pharmaceutical compositions are typically prepared by thoroughly and intimately mixing or blending the active agent with a pharmaceutically-acceptable carrier and one or more optional ingredients. The resulting uniformly blended mixture can then be shaped or loaded into tablets, capsules, pills and the like using conventional procedures and equipment.

In one aspect, the pharmaceutical composition is suitable for inhaled administration. Pharmaceutical compositions for inhaled administration are typically in the form of an aerosol or a powder. Such compositions are generally administered using inhaler delivery devices, such as a dry powder inhaler (DPI), a metered-dose inhaler (MDI), a nebulizer inhaler, or a similar delivery device.

In a particular embodiment, the pharmaceutical composition is administered by inhalation using a dry powder inhaler. Such dry powder inhalers typically administer the pharmaceutical composition as a free-flowing powder that is dispersed in a patient's air-stream during inspiration. In order to achieve a free-flowing powder composition, the therapeutic agent is typically formulated with a suitable excipient such as lactose, starch, mannitol, dextrose, poly-lactic acid (PLA), polylactide-co-glycolide (PLGA) or combinations thereof. Typically, the therapeutic agent is micronized and combined with a suitable carrier to form a composition suitable for inhalation.

A representative pharmaceutical composition for use in a dry powder inhaler comprises lactose and a compound of the invention in micronized form. Such a dry powder composition can be made, for example, by combining dry milled lactose with the therapeutic agent and then dry blending the components. The composition is then typically loaded into a dry powder dispenser, or into inhalation cartridges or capsules for use with a dry powder delivery device.

Dry powder inhaler delivery devices suitable for administering therapeutic agents by inhalation are described in the art and examples of such devices are commercially available. For example, representative dry powder inhaler delivery devices or products include Aeolizer (Novartis); Airmax (IVAX); ClickHaler (Innovata Biomed); Diskhaler (GlaxoSmithKline); Diskus/Accuhaler (GlaxoSmithKline); Ellipta (GaxoSmithKline); Easyhaler (Orion Pharma); Eclipse (Aventis); FlowCaps (Hovione); Handihaler (Boehringer Ingelheim); Pulvinal (Chiesi); Rotahaler (GaxoSmithKline); SkyeHaler/Certihaler (SkyePharma); Twisthaler (Schering-Plough); Turbuhaler (AstraZeneca); Ultrahaler (Aventis); and the like.

In another particular embodiment, the pharmaceutical composition is administered by inhalation using a metered-dose inhaler. Such metered-dose inhalers typically discharge a measured amount of a therapeutic agent using a compressed propellant gas. Accordingly, pharmaceutical compositions administered using a metered-dose inhaler typically comprise a solution or suspension of the therapeutic agent in a liquefied propellant. Any suitable liquefied propellant may be employed including hydrofluoroalkanes (HFAs), such as 1,1,1,2-tetrafluoroethane (HFA 134a) and 1,1,1,2,3,3,3-heptafluoro-n-propane, (HFA 227); and chlorofluorocarbons, such as $CCl_3F$. In a particular embodiment, the propellant is hydrofluoroalkanes. In some embodiments, the hydrofluoroalkane formulation contains a co-solvent, such as ethanol or pentane, and/or a surfactant, such as sorbitan trioleate, oleic acid, lecithin, and glycerin.

A representative pharmaceutical composition for use in a metered-dose inhaler comprises from about 0.01% to about 5% by weight of a compound of the invention; from about 0% to about 20% by weight ethanol; and from about 0% to about 5% by weight surfactant; with the remainder being an HFA propellant. Such compositions are typically prepared by adding chilled or pressurized hydrofluoroalkane to a suitable container containing the therapeutic agent, ethanol (if present) and the surfactant (if present). To prepare a suspension, the therapeutic agent is micronized and then combined with the propellant. The composition is then loaded into an aerosol canister, which typically forms a portion of a metered-dose inhaler device.

Metered-dose inhaler devices suitable for administering therapeutic agents by inhalation are described in the art and examples of such devices are commercially available. For example, representative metered-dose inhaler devices or products include AeroBid Inhaler System (Forest Pharmaceuticals); Atrovent Inhalation Aerosol (Boehringer Ingelheim); Flovent (GlaxoSmithKline); Maxair Inhaler (3M); Proventil Inhaler (Schering); Serevent Inhalation Aerosol (GlaxoSmithKline); and the like.

In another particular aspect, the pharmaceutical composition is administered by inhalation using a nebulizer inhaler. Such nebulizer devices typically produce a stream of high velocity air that causes the pharmaceutical composition to spray as a mist that is carried into the patient's respiratory tract. Accordingly, when formulated for use in a nebulizer inhaler, the therapeutic agent can be dissolved in a suitable carrier to form a solution. Alternatively, the therapeutic agent can be micronized or nanomilled and combined with a suitable carrier to form a suspension.

A representative pharmaceutical composition for use in a nebulizer inhaler comprises a solution or suspension comprising from about 0.05 μg/mL to about 20 mg/mL of a compound of the invention and excipients compatible with nebulized formulations. In one embodiment, the solution has a pH of about 3 to about 8.

Nebulizer devices suitable for administering therapeutic agents by inhalation are described in the art and examples of such devices are commercially available. For example, representative nebulizer devices or products include the Respimat Softmist Inhalaler (Boehringer Ingelheim); the AERx Pulmonary Delivery System (Aradigm Corp.); the PARI LC Plus Reusable Nebulizer (Pari GmbH); and the like.

In yet another aspect, the pharmaceutical compositions of the invention may alternatively be prepared in a dosage form intended for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present invention as an active ingredient.

When intended for oral administration in a solid dosage form, the pharmaceutical compositions of the invention will typically comprise the active agent and one or more pharmaceutically-acceptable carriers, such as sodium citrate or dicalcium phosphate. Optionally or alternatively, such solid dosage forms may also comprise: fillers or extenders, binders, humectants, solution retarding agents, absorption accelerators, wetting agents, absorbents, lubricants, coloring agents, and buffering agents. Release agents, wetting agents, coating agents, sweetening, flavoring and perfuming agents, preservatives and antioxidants can also be present in the pharmaceutical compositions of the invention.

Alternative formulations may also include controlled release formulations, liquid dosage forms for oral administration, transdermal patches, and parenteral formulations. Conventional excipients and methods of preparation of such alternative formulations are described, for example, in the reference by Remington, supra.

The following non-limiting examples illustrate representative pharmaceutical compositions of the present invention.

Dry Powder Composition

A micronized compound of formula (I) (1 g) is blended with milled lactose (25 g). This blended mixture is then loaded into individual blisters of a peelable blister pack in an amount sufficient to provide between about 0.1 mg to about 4 mg of the compound of formula I per dose. The contents of the blisters are administered using a dry powder inhaler.

Dry Powder Composition

A micronized compound of formula (I) (1 g) is blended with milled lactose (20 g) to form a bulk composition having a weight ratio of compound to milled lactose of 1:20. The blended composition is packed into a dry powder inhalation device capable of delivering between about 0.1 mg to about 4 mg of the compound of formula I per dose.

Metered-Dose Inhaler Composition

A micronized compound of formula (I) (10 g) is dispersed in a solution prepared by dissolving lecithin (0.2 g) in demineralized water (200 mL). The resulting suspension is spray dried and then micronized to form a micronized composition comprising particles having a mean diameter less than about 1.5 µm. The micronized composition is then loaded into metered-dose inhaler cartridges containing pressurized 1,1,1,2-tetrafluoroethane in an amount sufficient to provide about 0.1 mg to about 4 mg of the compound of formula I per dose when administered by the metered dose inhaler.

Nebulizer Composition

A compound of formula (I) (25 mg) is dissolved in a solution containing 1.5-2.5 equivalents of hydrochloric acid, followed by addition of sodium hydroxide to adjust the pH to 3.5 to 5.5 and 3% by weight of glycerol. The solution is stirred well until all the components are dissolved. The solution is administered using a nebulizer device that provides about 0.1 mg to about 4 mg of the compound of formula I per dose.

Utility

The JAK inhibitors of the invention have been designed for the treatment of inflammatory and fibrotic disease of the respiratory tract. In particular, the compounds have been designed to enable delivery of a potent anti-cytokine agent directly to the site of action of respiratory disease in the lung while limiting systemic exposure.

The compounds of the invention have been shown to be potent inhibitors of the JAK family of enzymes: JAK1, JAK2, JAK3, and TYK2. In addition, the compounds have demonstrated potent inhibition of pro-inflammatory and pro-fibrotic cytokines without exhibiting cytotoxicity in cellular assays. It has been recognized that the broad anti-inflammatory effect of JAK inhibitors could suppress normal immune cell function, potentially leading to increased risk of infection. The present compounds have therefore been optimized to limit absorption from the lung into the plasma, thus minimizing the risk of immunosuppression.

As described in the experimental section below, the absorption and distribution of typical compounds has been profiled in preclinical assays. Selected compounds tested in mice showed, at the same time, high concentration in lung tissue and low absorption into plasma. Compounds tested in mouse exhibited exposure in lung from one to two orders of magnitude greater than exposure in plasma. The compounds also exhibited significant retention in the mouse lung as evidenced by a lung half-life greater than about 5 hours. Importantly, the concentration of test compound in the mouse lung has been shown to correlate with a predicted pharmacodynamic effect of JAK enzyme inhibition. Compounds of the invention have been shown to inhibit an effect of the pro-inflammatory cytokine IL-13 in mouse lung tissue. Specifically, the compounds have demonstrated dose and concentration dependent inhibition of IL-13-induced phosphorylation of STAT6 in lung tissue which provides evidence of local lung JAK target engagement in vivo. This effect has been observed when the pro-inflammatory cytokine IL-13 is administered 4 hours after administration of the test compound, providing further evidence of significant retention in the lung.

Tested compounds have been demonstrated to exhibit both potent inhibitory activity at the cellular level and significant retention in lung tissue. Extensive investigation by the present inventors has determined that while it is possible to identify compounds that are potent at the cellular level or compounds that show significant retention in the lung, it is far more difficult to discover compounds that exhibit both desirable characteristics at the same time.

The diamino structure of the compounds of the present invention, including two amino nitrogen atoms, has been shown to be critical in satisfying both criteria of cellular potency and lung retention. As described in the assay section below, a compound in which the nitrogen atom in the group of formula (II) is replaced by a carbon atom does not satisfy both criteria. Not only is such a monoamino compound noticeably less potent at the cellular level than the corresponding diamino compound, but it does not exhibit significant inhibition in the pharmacodynamic assay nor exhibit high concentration in lung tissue under the same assay conditions in which the present compounds show significant retention in the lung.

Further, compounds of the invention have been demonstrated to show sufficient solubility at pH values compatible with formulations for administration by nebulization. Solubility may also be relevant to toxicity testing of compounds intended to be administered by inhalation. It has been observed that administration of undissolved particulate matter by inhalation can be associated with adverse lung effects during toxicity testing (Jones et al, *Xenobiotica*, 2011, 1-8). Solubility of the present compounds may also facilitate assessment of toxicity by inhalation.

The anti-inflammatory activity of JAK inhibitors has been robustly demonstrated in preclinical models of asthma (Malaviya et al., *Int Immunopharmacol*, 2010, 10, 829,-836; Matsunaga et al., *Biochem and Biophys Res Commun*, 2011, 404, 261-267; Kudlacz et al., *Eur J Pharmacol*, 2008, 582, 154-161.) Accordingly, the compounds of the invention are expected to be useful for the treatment of inflammatory respiratory disorders, in particular, asthma. Inflammation and fibrosis of the lung is characteristic of other respiratory diseases in addition to asthma such as chronic obstructive pulmonary disease (COPD), cystic fibrosis (CF), pneumonitis, interstitial lung diseases (including idiopathic pulmonary fibrosis), acute lung injury, acute respiratory distress syndrome, bronchitis, emphysema, and bronchiolitis obliterans. The present compounds, therefore, are also expected to be useful for the treatment of chronic obstructive pulmonary disease, cystic fibrosis, pneumonitis, interstitial lung diseases (including idiopathic pulmonary fibrosis), acute lung injury, acute respiratory distress syndrome, bronchitis, emphysema and bronchiolitis obliterans.

In one aspect, therefore, the invention provides a method of treating a respiratory disease in a mammal (e.g., a human), the method comprising administering to the mammal a therapeutically-effective amount of a compound of the invention or of a pharmaceutical composition comprising a pharmaceutically-acceptable carrier and a compound of the invention.

In one aspect, the respiratory disease is asthma, chronic obstructive pulmonary disease, cystic fibrosis, pneumonitis, chronic obstructive pulmonary disease (COPD), cystic fibrosis (CF), pneumonitis, interstitial lung diseases (including idiopathic pulmonary fibrosis), acute lung injury, acute respiratory distress syndrome, bronchitis, emphysema or bronchiolitis obliterans. In another aspect, the respiratory disease is asthma or chronic obstructive pulmonary disease.

The invention further provides a method of treating asthma in a mammal, the method comprising administering to the mammal a therapeutically-effective amount of a compound of the invention or of a pharmaceutical composition comprising a pharmaceutically-acceptable carrier and a compound of the invention.

When used to treat asthma, the compounds of the invention will typically be administered in a single daily dose or in multiple doses per day, although other forms of administration may be used. The amount of active agent administered per dose or the total amount administered per day will typically be determined by a physician, in the light of the relevant circumstances, including the condition to be treated, the chosen route of administration, the actual compound administered and its relative activity, the age, weight, and response of the individual patient, the severity of the patient's symptoms, and the like.

Compounds of the invention have been demonstrated to be potent inhibitors of the JAK1, JAK2, JAK3, and TYK2 enzymes in enzyme binding assays, to have potent functional activity without cytotoxicity in cellular assays, and to exert the pharmacodynamic effects of JAK inhibition in preclinical models, as described in the following examples.

EXAMPLES

The following synthetic and biological examples are offered to illustrate the invention, and are not to be construed in any way as limiting the scope of the invention. In the examples below, the following abbreviations have the following meanings unless otherwise indicated. Abbreviations not defined below have their generally accepted meanings.

ACN=acetonitrile
CPME=cyclopentyl methyl ether
DCM=dichloromethane
DIPEA=N,N-diisopropylethylamine
DMAc=dimethylacetamide
DMF=N,N-dimethylformamide
EtOAc=ethyl acetate
h=hour(s)
IPAc=isopropylacetate
KOAc=potassium acetate
MeOH=methanol
MeTHF=2-methyltetrahydrofuran
min=minute(s)
MTBE=methyl tert-butyl ether
NMP=N-methyl-2-pyrrolidone
Pd(amphos)$_2$Cl$_2$=bis(di-tert-butyl(4-dimethylaminophenyl)-phosphine)dichloropalladium(II)
Pd(dppf)Cl$_2$=dichloro(1,1'-bis(diphenylphosphino)-ferrocene)dipalladium(II)
Pd(PPh$_3$)$_4$=tetrakis(triphenylphosphine)palladium(0)
Pd(t-Bu$_3$P)$_2$=bis(tri-tert-butylphosphine) palladium(0)
RT=room temperature
TEA=triethylamine
TFA=trifluoroacetic acid
THF=tetrahydrofuran
bis(pinacolato)diboron=4,4,5,5,4',4',5',5'-octamethyl-[2,2']bi[[1,3,2]dioxaborolanyl]

Reagents and solvents were purchased from commercial suppliers (Aldrich, Fluka, Sigma, etc.), and used without further purification. Progress of reaction mixtures was monitored by thin layer chromatography (TLC), analytical high performance liquid chromatography (anal. HPLC), and mass spectrometry. Reaction mixtures were worked up as described specifically in each reaction; commonly they were purified by extraction and other purification methods such as temperature-, and solvent-dependent crystallization, and precipitation. In addition, reaction mixtures were routinely purified by column chromatography or by preparative HPLC, typically using C18 or BDS column packings and conventional eluents. Typical preparative HPLC conditions are described below.

Characterization of reaction products was routinely carried out by mass and $^1$H-NMR spectrometry. For NMR analysis, samples were dissolved in deuterated solvent (such as CD$_3$OD, CDCl$_3$, or d$_6$-DMSO), and $^1$H-NMR spectra were acquired with a Varian Gemini 2000 instrument (400 MHz) under standard observation conditions. Mass spectrometric identification of compounds was performed by an electrospray ionization method (ESMS) with an Applied Biosystems (Foster City, Calif.) model API 150 EX instrument or a Waters (Milford, Mass.) 3100 instrument, coupled to autopurification systems.

Preparative HPLC Conditions
Column: C18, 5 µm. 21.2×150 mm or C18, 5 µm 21×250 or C14, 5 µm 21×150 mm
Column temperature: Room Temperature
Flow rate: 20.0 mL/min
Mobile Phases: A=Water+0.05% TFA
B=ACN+0.05% TFA,
Injection volume: (100-1500 µL)
Detector wavelength: 214 nm Crude compounds were dissolved in 1:1 water:acetic acid at about 50 mg/mL. A 4 minute analytical scale test run was carried out using a 2.1×50 mm C18 column followed by a 15 or 20 minute preparative scale run using 100 µL injection with the gradient based on the % B retention of the analytical scale test run. Exact gradients were sample dependent. Samples with close running impurities were checked with a 21×250 mm C18 column and/or a 21×150 mm C14 column for best separation. Fractions containing desired product were identified by mass spectrometric analysis.

Analytic HPLC Conditions
Method A
Column: Advanced Material Technology HALO® C18 (2), 150×4.60 nm,
2.7 micron
Column temperature: 30° C.
Flow rate: 1.0 m/min
Injection volume: 5 µL
Sample preparation: Dissolve in 1:1 ACN:water
Mobile Phases: A=Water:ACN:TFA (98:2:0.1)
B=Water:ACN: TFA (30:70:0.1)

Detector wavelength: 254 nm
Gradient: 22 min total (time (min)/% B): 0/30, 15/100, 18/100, 20/30, 22/30
Method B
Column: Agilent Zorbax Bonus-RP C18, 150×4.60 nm, 3.5 micron
Column temperature: 40° C.
Flow rate: 1.5 m/min
Injection volume: 5 μL
Sample preparation: Dissolve in 1:1 ACN:1 M HCl
Mobile Phases: A=Water: TFA (99.95:0.05)
  B=ACN:TFA (99.95:0.05)
Detector wavelength: 254 nm and 214 nm
Gradient: 26 min total (time (min)/% B): 0/5, 18/90, 22/90, 22.5/90, 26/5
Method C
Column: Agilent Poroshell 120 Bonus-RP, 4.6×150 mm, 2.7 μm
Column temperature: 30° C.
Flow rate: 1.5 m/min
Injection volume: 10 μL
Mobile Phases: A=ACN:Water:TFA (2:98:0.1)
  B=ACN:Water:TFA (90:10:0.1)
Sample preparation: Dissolve in Mobile phase B
Detector wavelength: 254 nm and 214 nm
Gradient: 60 min total (time (min)/% B): 0/0, 50/100, 55/100, 55.1/0, 60/0

Preparation 1:
1-(Benzyloxy)-4-bromo-5-ethyl-2-fluorobenzene

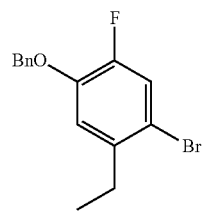

(a) 5-Ethyl-2-fluorophenol

A mixture of compound 5-bromo-2-fluorophenol (80 g, 419 mmol) in dry tetrahydrofuran (800 mL) was degassed and purged with nitrogen 3 times, and Pd(t-Bu₃P)₂ (4.28 g, 8.38 mmol) was added. Diethylzine (114 g, 921 mmol) was added to the mixture dropwise at 25° C., and the reaction mixture was stirred at 50° C. for 12 h under nitrogen and slowly poured into ice-water (1 L). EtOAc (350 mL) was added and the reaction mixture was stirred for 20 min and filtered. The filter cake was washed with EtOAc (3×500 mL). The combined organic layers were washed with brine (600 mL), dried over sodium sulfate, concentrated, and purified by silica gel chromatography to give the title intermediate (85 g, crude) as a yellow oil.

(b) 2-(Benzyloxy)-4-ethyl-1-fluorobenzene

To a solution of the product of the previous step (85 g, 606 mmol) in ACN (850 mL) was added benzyl bromide (124 g, 728 mmol) and K₂CO₃ (126 g, 909 mmol). The reaction mixture was stirred at 25° C. for 12 h, poured into water (1 L) and extracted with EtOAc (4×500 mL). The combined organic layers were washed with brine (600 mL), dried over sodium sulfate, concentrated, and purified by silica gel chromatography to give the title intermediate (100 g) as a yellow oil.

(c) 1-(Benzyloxy)-4-bromo-5-ethyl-2-fluorobenzene

To a solution of the product of the previous step (100 g, 434 mmol) in ACN (1.0 L) was added N-bromosuccinimide (85 g, 477 mmol) portion wise. The reaction mixture was stirred at 25° C. for 5 h, poured into water (1.3 L) and extracted with EtOAc (3×500 mL). The combined organic layers were washed with brine (800 mL), dried over sodium sulfate, concentrated, and purified by silica gel chromatography to give the title compound (83 g) as yellow oil. ¹H NMR (CDCl₃, 400 MHz) δ (ppm) 7.27-7.43 (m, 6H), 6.86 (d, J=8.4 Hz, 1H), 5.10 (s, 2H), 2.64 (q, J=7.6 Hz, 2H), 1.15 (t, J=7.2 Hz, 1H).

Preparation 2: 2-(4-(Benzyloxy)-2-ethyl-5-fluorophenyl)-4,4,5,5-tetramethyl-1,3,2-dioxaborolane

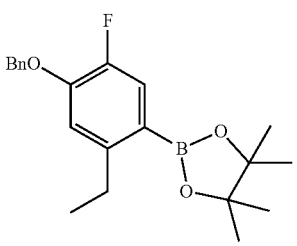 [SMILES: CCc1cc(OCc2ccccc2)c(F)cc1B1OC(C)(C)C(C)(C)O1]

A mixture of the compound of Preparation 1 (83 g, 268 mmol), bis(pinacolato)diboron (102 g, 402 mmol), and KOAc (79.0 g, 805 mmol) in dioxane (830 mL) was degassed and purged with nitrogen 3 times, and Pd(dppf)Cl₂ (3.93 g, 5.37 mmol) was added. The reaction mixture was stirred at 120° C. for 4 h under nitrogen. The mixture was cooled to 25° C., poured into water (1 L), and extracted with EtOAc (3×500 mL). The combined organic layers were washed with brine (800 mL), dried over sodium sulfate, and purified by silica gel chromatography. The product was washed with methanol (200 mL), filtered, and the filter cake was dried to give the title compound (65 g) as white solid. ¹H NMR (CDCl₃, 400 MHz) δ (ppm) 7.26-7.42 (m, 5H), 6.74 (d, J=7.6 Hz, 1H), 5.08 (s, 2H), 2.76 (q, J=7.2 Hz, 2H), 1.25 (s, 12H), 1.06 (t, J=7.6 Hz, 3H).

Preparation 3:
1-Benzyl-4-imino-1,4-dihydropyridin-3-amine

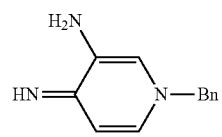

To a solution of pyridine-3,4-diamine (200 g, 1.8 mol) in ACN (17.0 L) was added benzyl bromide (306 g, 1.79 mol) and the reaction mixture was stirred at 15° C. for 12 h, filtered and the filter cake was dried under vacuum to give the title compound (250 g) as a white solid. ¹H NMR (d$_6$-DMSO, 400 MHz) δ (ppm) 8.02 (dd, J=7.2, 1.6 Hz, 1H), 7.66 (s, 1H), 7.34-7.41 (m, 5H), 6.79 (d, J=6.8 Hz, 1H), 5.62 (s, 2H), 5.36 (s, 2H).

Preparation 4: 5-Benzyl-2-(6-bromo-1H-indazol-3-yl)-5H-imidazo[4,5-c]pyridine

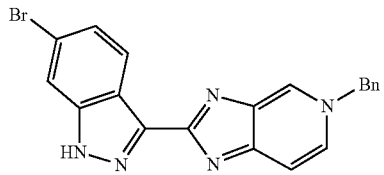 [SMILES: Brc1ccc2c(-c3nc4ccn(Cc5ccccc5)cc-4n3)n[nH]c2c1]

(a) 6-Bromo-1H-indazol-3-yl-carbaldehyde

A solution of NaNO$_2$ (704 g, 10.2 mol) in water (1 L) was added dropwise to a solution of 6-bromo-1H-indole (400 g, 2.0 mol) in acetone (7 L) at 10° C. The reaction mixture was stirred at 10° C. for 30 min, aqueous 3M HCl (437 mL) was added slowly with vigorous stirring, keeping the internal temperature between 10 and 25° C. The solution was stirred at 20° C. for 3 h, and concentrated while keeping the temperature below 35° C. The solid was collected by filtration. The filter cake was washed with 1:2 petroleum ether: MTBE (800 mL). The solids were collected by filtration and dried under vacuum to afford the title intermediate (450 g) as a black brown solid. $^1$H NMR (CH$_3$OD, 400 MHz) δ (ppm) 7.77 (d, J=8.8 Hz, 1H), 7.69 (s, 1H), 7.22 (dd, J=8.4, 2.4 Hz, 1H), 5.70 (s, 1H).

b) 5-Benzyl-2-(6-bromo-1H-indazol-3-yl)-5H-imidazo[4,5-c]pyridine

To a stirred solution of 6-bromo-1H-indazol-3-yl-carbaldehyde (150.0 g, 666 mmol) and 1-benzyl-4-imino-1,4-dihydropyridin-3-amine (127.5 g, 639.9 mmol) in DMF (750 mL) was charged NaHSO$_3$ (83.2 g, 799.9 mmol) and the reaction mixture was stirred for 6 h at 140° C. and poured into water (3.5 L). The precipitate was filtered and washed with water (1 L) to give the title compound (180 g) as a black brown solid. $^1$H NMR (d$_6$-DMSO, 400 MHz) δ (ppm) 8.69 (s, 1H) 8.71 (d, J=7.2 Hz, 1H) 8.37 (d, J=8.4 Hz, 1H) 8.07 (d, J=6.4 Hz, 1H) 7.97 (s, 1H) 7.38-7.43 (m, 3H) 7.50-7.54 (m, 4H) 5.87 (s, 2H).

Preparation 5: 5-Benzyl-2-(6-bromo-1H-indazol-3-yl)-4,5,6,7-tetrahydro-1H-imidazo[4,5-c]pyridine

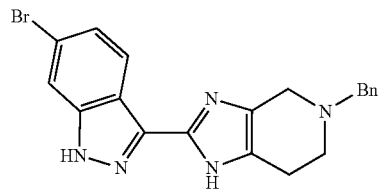 [SMILES: Brc1ccc2c(-c3nc4c([nH]3)CCN(Cc3ccccc3)C4)n[nH]c2c1]

To a solution of 5-benzyl-2-(6-bromo-1H-indazol-3-yl)-5H-imidazo[4,5-c]pyridine (23.0 g, 56.9 mmol) in MeOH (200 mL) and THF (1 L) was added NaBH$_4$ (12.9 g, 341.3 mmol) portion-wise and the reaction mixture was stirred at 50° C. for 2 h. Acetic acid (10 eq) was added, the solution was concentrated to dryness and purified by silica gel chromatography (30 g silica, 0-10% MeOH/DCM with 0.1% TEA) to give the title compound (6.0 g). $^1$H NMR (d$_6$-DMSO, 400 MHz) δ (ppm) 8.24 (d, J=8.0 Hz, 1H), 7.77 (s, 1H), 7.28-7.37 (m, 7H), 3.74 (s, 2H), 3.48 (br.s, 2H), 2.80 (s, 2H), 2.66 (s, 2H).

Preparation 6: 5-Benzyl-2-(6-(4-(benzyloxy)-2-ethyl-5-fluorophenyl)-1H-indazol-3-yl)-4,5,6,7-tetrahydro-1H-imidazo[4,5-c]pyridine

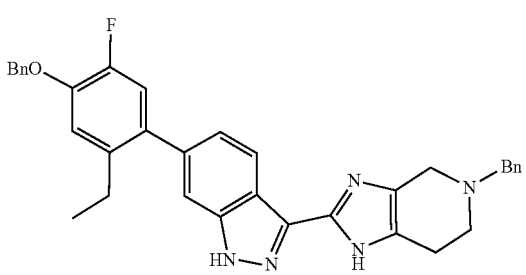 [SMILES: CCc1cc(OCc2ccccc2)c(F)cc1-c1ccc2c(-c3nc4c([nH]3)CCN(Cc3ccccc3)C4)n[nH]c2c1]

(a) tert-Butyl 5-benzyl-2-(6-bromo-1-(tert-butoxycarbonyl)-1H-indazol-3-yl)-4,5,6,7-tetrahydro-1H-imidazo[4,5-c]pyridine-1-carboxylate Two reactions were carried out in parallel. A suspension of 5-benzyl-2-(6-bromo-1H-indazol-3-yl)-4,5,6,7-tetrahydro-1H-imidazo[4,5-c]pyridine (80 g, 196 mmol), di-tert-butyl dicarbonate (128 g, 587.8 mmol, 135 mL) and TEA (79.3 g, 784 mmol, 109 mL) in DCM (1 L) was stirred at 20° C. for 12 h. The two reaction suspensions were combined, concentrated to dryness, and purified by silica gel chromatography (petroleum ether:EtOAc 10:1-0:1) to give the title intermediate (170.0 g).

(b) 5-Benzyl-2-(6-bromo-1H-indazol-3-yl)-4,5,6,7-tetrahydro-1H-imidazo[4,5-c]pyridine Two reactions were carried out in parallel. A solution of the product of the previous step (85 g, 140 mmol) and 4M HCl in MeOH (400 mL) in DCM (400 mL) was stirred at 25° C. for 12 h. The reaction mixtures were combined and concentrated to dryness, DCM (250 mL) was added with stirring, and the reaction mixture was stirred for 30 min and filtered. The filter cake was washed with DCM (2×20 mL) and dried to give the title compound (85 g) as an off-white solid.

(c) 5-Benzyl-2-(6-(4-(benzyloxy)-2-ethyl-5-fluorophenyl)-1H-indazol-3-yl)-4,5,6,7-tetrahydro-1H-imidazo[4,5-c]pyridine Eighty-five reactions were carried out in parallel. The product of the previous step (1.0 g, 2.5 mmol), 2-(4-(benzyloxy)-2-ethyl-5-fluorophenyl)-4,4,5,5-tetramethyl-1,3,2-dioxaborolane (873 mg, 2.5 mmol), and Pd(PPh$_3$)$_4$ (227 mg, 196. μmol) were dissolved in a mixture of water (4 mL) and dioxane (10 mL). The reaction vial was bubbled with nitrogen for 2 min and Na$_2$CO$_3$ (779 mg, 7.4 mmol) was added quickly under nitrogen. The reaction mixture was heated at 130° C. for 1.5 h. The 85 reaction mixtures were combined and concentrated under reduced pressure. The residue was dissolved in DCM (500 mL) and purified by silica gel chromatography (150 g silica, eluted with DCM:THF (6:1 to 3:1)) to give compound the title compound (50 g) as an off-white solid.

Preparation 7: 5-Ethyl-2-fluoro-4-(3-(4,5,6,7-tetrahydro-1H-imidazo[4,5-c]pyridin-2-yl)-1H-indazol-6-yl)phenol

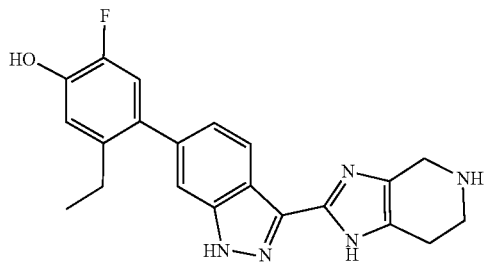 [SMILES: CCc1cc(O)c(F)cc1-c1ccc2c(-c3nc4c([nH]3)CCNC4)n[nH]c2c1]

A mixture of 5-benzyl-2-(6-(4-(benzyloxy)-2-ethyl-5-fluorophenyl)-1H-indazol-3-yl)-4,5,6,7-tetrahydro-1H-imidazo[4,5-c]pyridine (44.5 g, 79.8 mmol), Pd(OH)$_2$/C (25 g, 2.7 mmol, 50% purity) and TFA (44.5 g, 390 mmol, 28.9 mL) in MeOH (500 mL) was stirred under hydrogen (50 Psi) for 4 h and filtered. Pd(OH)$_2$/C (25 g, 2.7 mmol, 50% purity) was added to the filtrate and the resulting suspension was stirred under hydrogen (50 Psi) at 25° C. for 12 h. The suspension was combined with the suspension from a prior reaction at the 5.5 g scale and filtered. The filter cake was washed with 20:1 MeOH:TFA (2×200 mL). The combined filtrate was concentrated and 4 M HCl in MeOH (200 mL) was added to the residue with stirring. The resulting suspension was concentrated, slurried with MeOH (80 mL) and stirred for 30 min. A white solid precipitated. The solid was filtered, the filter cake was washed with MeOH (2×10 mL) and dried under vacuum to give the HCl salt of the title compound (24.8 g) as an off-white solid. (m/z): [M+H]$^+$ calcd for $C_{21}H_{20}FN_5O$ 378.17 found 378.1. $^1$H NMR (d$_6$-DMSO, 400 MHz) δ (ppm) 8.23 (d, J=8.4 Hz, 1H), 7.59 (s, 1H), 7.35 (d, J=11.2 Hz, 1H), 6.90-6.97 (m, 2H), 4.57 (s, 2H), 3.72 (t, J=6.0 Hz, 2H), 3.22 (t, J=6.0 Hz, 2H), 2.51 (q, J=7.6 Hz, 2H), 1.04 (t, J=7.6 Hz, 3H).

Preparation 8: (4-(Benzyloxy)-2-ethyl-5-fluorophenyl)trifluoroborate, potassium

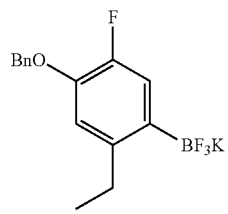

(a) 1-(Benzyloxy)-4-bromo-5-ethyl-2-fluorobenzene

To a mixture of 4-bromo-5-ethyl-2-fluorophenol (50 g, 228 mmol) and DMF (200 mL) was added potassium carbonate (34.7 g, 251 mmol) at RT. The reaction mixture was stirred for 15 min; benzyl bromide (25.8 mL, 217 mmol) was added dropwise; the reaction mixture was stirred at RT overnight and poured into water (1 L). Ethyl acetate (1 L) was added; the phases were separated; the organic layer was washed with brine (1 L), and dried with sodium sulfate followed by solvent removal to provide the crude title intermediate (71 g) thick oil. HPLC Method A Retention time 17.37 min.

(b) 2-(4-(Benzyloxy)-2-ethyl-5-fluorophenyl)-4,4,5,5-tetramethyl-1,3,2-dioxaborolane A mixture of the product of the previous step (70 g, 226 mmol) and dioxane (800 mL) was purged with nitrogen and then bis(pinacolato)diboron (86 g, 340 mmol) was added followed by potassium acetate (66.7 g, 679 mmol). The reaction mixture was purged with nitrogen; Pd(dppf)Cl$_2$ (3.31 g, 4.53 mmol) was added; the reaction mixture was heated at 120° C. under nitrogen for 4 h; cooled to RT and stirred overnight. The reaction mixture was concentrated by rotary evaporation and partitioned between water (800 mL) and ethyl acetate (800 mL). The organic layer was washed with brine (800 mL) and dried with sodium sulfate followed by solvent removal. The crude product was dissolved in DCM (400 mL) and purified by silica gel chromatography (1 kg silica, eluted with 20% ethyl acetate in hexanes (2 L)). Solvent was removed by rotary evaporation to provide the title intermediate (81 g) as a light yellow oil.

(c) (4-(benzyloxy)-2-ethyl-5-fluorophenyl)trifluoroborate, potassium

The product of the previous step (81 g, 227 mmol) was mixed with acetone (400 mL) until complete dissolution and methanol (400 mL) was added followed by 3 M potassium hydrogen difluoride in water (379 mL, 1137 mmol) and the reaction mixture was stirred at RT. Most of the solvent was removed by rotary evaporation. Water (500 mL) was added and the resulting thick slurry was stirred for 30 min and filtered. The flask and cake were washed with water (2×100 mL) and the solid was dried overnight. Toluene (400 mL) was added, of which 200 mL was removed by rotary evaporation at 50° C. The reaction mixture was cooled to RT, stirred for 30 min and filtered. The solid was dried to provide the title compound (69.7 g, 205 mmol, 90% yield) as a white solid. HPLC Method A Retention time 10.90 min.

Preparation 9: 5-Benzyl-2-(6-bromo-1H-indazol-3-yl)-5H-imidazo[4,5-c]pyridine

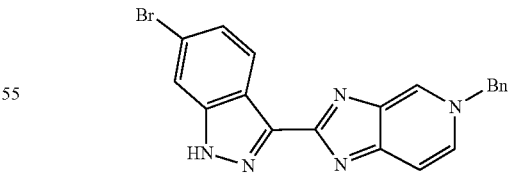

(a) 1-Benzyl-4-imino-1,4-dihydropyridin-3-amine

A mixture of pyridine-3,4-diamine (700 g, 6.414 mol) and ACN (15.5 L) was stirred for 80 min from 25° C. to 15° C. A solution of benzyl bromide (763 mL, 6.414 mol) in ACN (1 L) was added in 10 min and the reaction mixture was stirred for 1 h at 25° C. and at 20° C. overnight. The reaction mixture was filtered. The reactor and cake were washed with ACN (8 L) and warmed to 25° C., and again washed with ACN (8 L) and warmed to 25° C. The solid was dried on the filter for 3 h under nitrogen, at 50° C. under vacuum for 2 h and then at RT overnight to provide the HBR salt of the title intermediate (1659 g, 5.922 mol, 92% yield). HPLC Method B Retention time 3.74 min.

(b) 5-Benzyl-2-(6-bromo-1H-indazol-3-yl)-5H-imidazo[4,5-c]pyridine

A solution of 6-bromo-1H-indazole-3-carbaldehyde (558 g, 2.480 mol), the product of the previous step (746 g, 2.529 mol) and DMF (4.75 L) was stirred for 80 min and sodium bisulfite (261 g, 2.504 mol) was added with mixing. The reaction mixture was heated to 135° C. and held for 2 h and allowed to cool to RT in about 3 h, cooled to 2° C. and held for 1 h at 0-5° C. The slurry was filtered on a pressure filter by slow filtration. To the reactor was added DMF (1 L) and the reaction mixture was cooled to 5° C. The cake was washed and the procedure repeated with another portion of DMF (4 L). The cake was washed with ACN (1 L) and dried under nitrogen and under vacuum overnight to provide the title compound (1080 g, 2.591 mol, 105% yield, 97% purity) as a light yellow solid. HPLC Method B Retention time 7.83 min.

A mixture of the title compound (1000 g, 2.474 mol) and MeTHF (6 L) was heated to 55° C. and 1 M sodium hydroxide (3.216 L) was added in 5 min. The temperature dropped to 45° C. and the mixture was diluted with cold sodium hydroxide solution. The layers were allowed to separate and the aqueous later was drained. The mixture was cooled to RT and then to 5° C. and held overnight. The mixture was filtered and the reactor and cake washed with MeTHF (1 L). The resulting beige to yellow solid was dried on the filter for 3 days to provide the title compound (700 g, 1.680 mol, 67.9% yield, 97% purity) as a pale yellow solid. HPLC Method B Retention time 7.84 min.

Preparation 10: 5-benzyl-2-(6-bromo-H-indazol-3-yl)-4,5,6,7-tetrahydro-1H-imidazo[4,5-c]pyridine

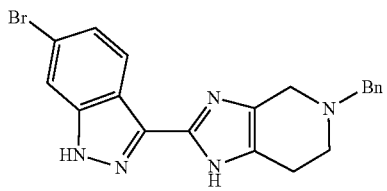 [SMILES: Brc1ccc2c(-c3nc4c([nH]3)CCN(Cc3ccccc3)C4)n[nH]c2c1]

To a 15 L flask was added 5-benzyl-2-(6-bromo-1H-indazol-3-yl)-5H-imidazo[4,5-c]pyridine (350 g, 866 mmol) followed by MeTHF (4 L), methanol (2 L) and water (1 L). The slurry was stirred at 25° C. for 45 min and NaBH$_4$ (197 g, 5195 mmol) was added in two portions. The reaction mixture was stirred at 25° C. for 18 h. Water (1 L) was added followed by 20 wt %. sodium chloride solution (2 L) and the reaction mixture was stirred for 30 min and the layers allowed to separate. The aqueous layer was drained; NaOH (1.732 L) was added and the reaction mixture was stirred for 30 minutes; the layers were allowed to separate and the aqueous layer was drained.

The organic layer was combined with the product of a second batch at the same scale and concentrated to about half the volume by rotary evaporation at 55° C. The layers were allowed to settle and the aqueous layer was drained. To the organic layer was added 3M HCl in CPME (1.732 L) at 35° C. followed by MeTHF (4 L) and MeOH (4 L) and the mixture heated to 60° C. to form a thick slurry, cooled to 25° C. in 5 h and held at that temperature overnight. The slurry was transferred to a pressure filter and the wet cake transferred to two tray-driers at 55° C. and dried under vacuum and under nitrogen for 6 h and then at 35° C. for 2 days to afford the 3 HCl salt of the title compound (609 g, 1153 mmol, 66.6% yield, 98% purity) as a bristle yellow/beige solid. HPLC Method B Retention time 5.93 min.

Preparation 11: 5-Benzyl-2-(6-(4-(benzyloxy)-2-ethyl-5-fluorophenyl)-1H-indazol-3-yl)-4,5,6,7-tetrahydro-1H-imidazo[4,5-c]pyridine

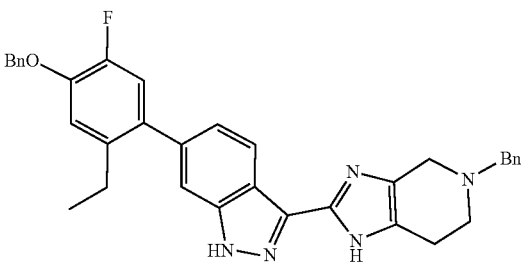 [SMILES: CCc1cc(OCc2ccccc2)c(F)cc1-c1ccc2c(-c3nc4c([nH]3)CCN(Cc3ccccc3)C4)n[nH]c2c1]

To a 5 L flask was added cesium carbonate (123 g, 377 mmol) and water (455 mL) with stirring at 22° C., followed by 5-benzyl-2-(6-bromo-H-indazol-3-yl)-4,5,6,7-tetrahydro-1H-imidazo[4,5-c]pyridine, 3HCl (65 g, 126 mmol) and MeOH (1365 mL). The slurry was heated to reflux for 0.5 h and cesium carbonate (127 g, 389 mmol) was added followed by (4-(benzyloxy)-2-ethyl-5-fluorophenyl)trifluoroborate, potassium (52.8 g, 157 mmol). The slurry was purged with nitrogen three times, bis(di-tert-butyl(4-dimethylaminophenyl) phosphine) dichloropalladium(II) (8.89 g, 12.56 mmol) was added and the reaction mixture was heated at reflux for 42 h. Additional (4-(benzyloxy)-2-ethyl-5-fluorophenyl)trifluoroborate, potassium (5.28 g, 15.7 mmol) and cesium carbonate (16.4 g, 50.3 mmol) were added and the reaction mixture was stirred at reflux for an additional 18 h and cooled to 25° C.

To the reaction mixture was added 1M HCl in water (502 mL, 502 mmol) followed by water (3 L). The resulting slurry was stirred at 22° C. for 1 h, and filtered. The filter cake was rinsed with water (1 L) and dried under vacuum and under nitrogen to provide the 3HCl salt of the title compound (88 g, 132 mmol, 105% yield) which was used directly in the following step. HPLC Method B Retention time 10.07 min.

Preparation 12: 5-ethyl-2-fluoro-4-(3-(4,5,6,7-tetra-hydro-1H-imidazo[4,5-c]pyridin-2-yl)-1H-indazol-6-yl)phenol

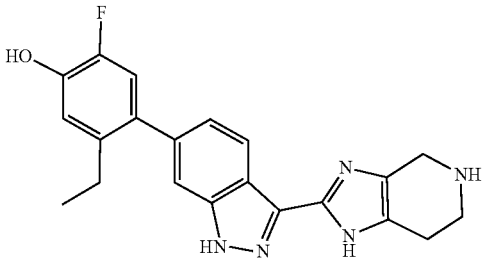 [SMILES: CCc1cc(O)c(F)cc1-c1ccc2c(-c3nc4c([nH]3)CCNC4)n[nH]c2c1]

A solution of 5-benzyl-2-(6-(4-(benzyloxy)-2-ethyl-5-fluorophenyl)-1H-indazol-3-yl)-4,5,6,7-tetrahydro-1H-imidazo[4,5-c]pyridine (70.6 g, 127 mmol) in EtOH (845 mL) and 1.25 M HCl in MeOH (203 mL, 253 mmol) was stirred under nitrogen for 10 min with heating to 50° C. and then 10 wt % Pd/C (8.45 g) was added immediately followed by hydrogen gas. The reaction mixture was sealed under hydrogen (50 Psi) at 50° C. for 3 h, filtered through Celite®, and concentrated to 169 mL. Ethyl acetate (845 mL) was added, the reaction mixture was concentrated to 169 mL, EtOAc (1521 mL) was added and the reaction mixture was stirred at 22° C. for 1 h, cooled to 0° C., then held for 1 h and filtered. The cake was rinsed with EtOAc (100 mL) and dried under vacuum and under nitrogen to afford the 3 HCl salt of the title product (52 g, 107 mmol, 70.5% yield). HPLC Method B Retention time 6.06 min.

Preparation 13: 5-Benzyl-2-(6-bromo-1H-indazol-3-yl)-5H-imidazo[4,5-c]pyridine

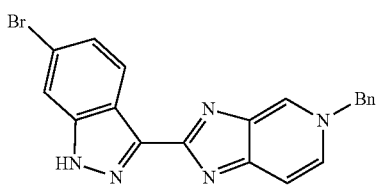 [SMILES: Brc1ccc2c(-c3nc4ccn(Cc5ccccc5)cc-4n3)n[nH]c2c1]

(a) 5-Benzyl-2-(6-bromo-1H-indazol-3-yl)-5H-imidazo[4,5-c]pyridine

A solution of 6-bromo-1H-indazole-3-carbaldehyde (550 g, 2.444 mol), 1-benzyl-4-imino-1,4-dihydropyridin-3-amine HBr (721 g, 2.333 mol) and DMAc (2.65 L) was stirred for 60 min and sodium bisulfite (257 g, 2.468 mol) was added. The reaction mixture was heated to 135° C. and held for 3 h, and allowed to cool to 20° C. and held at 20° C. overnight. Acetonitrile (8 L) was added and the reaction mixture was stirred for 4 h at 15° C. The slurry was filtered on a pressure filter at medium filtration rate. To the reactor was added ACN (1 L) The cake was washed with the ACN reactor wash and dried under nitrogen overnight and then under vacuum at 50° C. for 24 h to provide the HBr salt of the title compound (1264 g, 2.444 mol, 100% yield, 94% purity) as a dense wet beige/brown solid. HPLC Method B Retention time 8.77 min.

A mixture of the product of the previous step (1264 g, 2.444 mol), MeTHF (6 L) and water (2.75 L) was heated to 65° C. and sodium hydroxide 50 wt % (254 g, 3.177 mol) was added over 5 min and the reaction mixture was stirred at 65° C. for 1 h, cooled to RT, then to 5° C. and held for 2 h. The slurry was filtered and the reactor and cake were washed with MeTHF (1 L). The resulting beige to yellow solid was dried on the filter under nitrogen for 3 d to provide the title compound (475 g, 1.175 mmol, 48% yield) as a beige/yellow solid. The mother liquor (about 8 L) was concentrated to about 2 L, whereupon solids began to crash out, The slurry was heated to 50° C., held for 2 h, cooled to 5° C. over 2 h, stirred overnight, and filtered. The cake was washed with MeTHF (100 mL) and dried overnight under vacuum at 40° C. to provide additional title compound (140 g, 0.346 mol, 14% yield).

A mixture of the total product of the previous step, combined with the product of a second batch at the same scale (1500 g, 3.710 mol) and MeTHF (4 L) was stirred at 20° C. for 2 h and filtered. The reactor and cake were washed with MeTHF (1.5 L). The resulting beige to yellow solid was dried under nitrogen for 3 d to provide the title compound as a beige yellow solid (1325 g, 3.184 mol, 86% yield (overall 68% yield), 97% purity). HPLC Method B Retention time 8.77 min Preparation 14: 5-benzyl-2-(6-bromo-1H-indazol-3-yl)-4,5,6,7-tetrahydro-1H-imidazo[4,5-c]pyridine

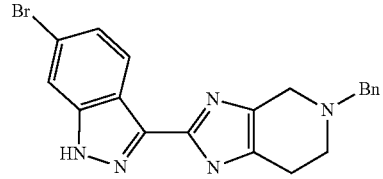 [SMILES: Brc1ccc2c(-c3nc4c([nH]3)CCN(Cc3ccccc3)C4)n[nH]c2c1]

To a 15 L flask was added 5-benzyl-2-(6-bromo-1H-indazol-3-yl)-5H-imidazo[4,5-c]pyridine (440 g, 1.088 mol) followed by MeTHF (4.5 L), methanol (2.25 L) and water (1.125 L). The slurry was cooled to 20° C., stirred for 1 h, and NaBH$_4$ (247 g, 6.530 mol) was added. The reaction mixture was stirred at 25° C. for 18 h. Water (1.125 L) was added followed by 20 wt %. sodium chloride solution (1.125 L) and the mixture was stirred for 30 min and the layers allowed to separate. The aqueous layer was drained. A premixed solution of NaOH (522 g) and water (5 L) was added and the reaction mixture was stirred for 60 min; the layers were allowed to separate and the aqueous layer was drained. Two additional batches at the same scale were prepared.

The organic layer from one batch was concentrated under reduced pressure in a 15 L jacketed reactor with the jacket set at 50° C., internal temperature 20° C. The additional batches were added to the reactor and concentrated one at a time resulting in a slurry about 6 L in volume. The slurry was heated to 50° C., IPAc (6 L) was added and the mixture was held at 60° C. for 1.5 h, cooled to 20° C. for 10 h, heated to 60° C. for 50 h, cooled to 20° C. in 5 h, then cooled to 5° C. and held for 3 h. The mixture was filtered and the reactor and cake was washed with a premixed solution of IPAc (1 L) and MeTHF (1 L), precooled to 5° C. The solids were dried under nitrogen on the filter at 40° C. for 3 d to provide the title compound (1059 g, 2.589 mol, 79% yield) as an off-white solid. The material was further dried in a vacuum oven at 50-60° C. for 8 h and at 27° C. for 2 d to provide the title compound (1043 g, 2.526 mol, 77% yield, 99% purity). HPLC Method B Retention time 6.73 min.

Preparation 15: (4-(Benzyloxy)-2-ethyl-5-fluorophenyl)trifluoroborate, potassium

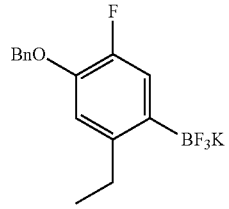

(a) 2-(4-(Benzyloxy)-2-ethyl-5-fluorophenyl)-4,4,5,5-tetramethyl-1,3,2-dioxaborolane A mixture of 1-(benzyloxy)-4-bromo-5-ethyl-2-fluorobenzene (520 g, 1682 mmol) and dioxane (5193 mL) was purged with nitrogen and then bis(pinacolato)diboron (641 g, 2523 mmol) was added followed by potassium acetate (495 g, 5046 mmol). The reaction mixture was purged with nitrogen; Pd(dppf)Cl$_2$ (41.2 g, 50.5 mmol) was added; the reaction mixture was purged with nitrogen, heated at 103° C. under nitrogen for 5 h; and cooled to RT. The reaction mixture was concentrated by vacuum distillation and partitioned between ethyl acetate (5204 mL) and water (5212 mL). The reaction mixture was filtered through Celite; the organic layer was washed with brine (2606 mL) followed by solvent removal by vacuum distillation to provide crude product as a thick black oil (~800 g).

The crude product was dissolved in DCM (1289 mL) and purified by silica gel chromatography (2627 g silica preslurried in hexane, eluted with 20% ethyl acetate in hexanes (10.35 L)). Solvent was removed by vacuum distillation to yield a light yellow oil (600 g). HPLC Method C Retention time 33.74 min.

(b) (4-(benzyloxy)-2-ethyl-5-fluorophenyl)trifluoroborate, potassium

The product of the previous step (200 g, 561 mmol) was mixed with acetone (1011 mL) until complete dissolution and methanol (999 mL) was added followed by 3 M potassium hydrogen difluoride (307 g, 3930 mmol) dissolved in water (1310 mL). The reaction mixture was stirred for 3.5 h. Most of the organic solvent was removed by vacuum distillation. Water (759 mL) was added and the resulting thick slurry was stirred for 30 min and filtered. The cake was washed with water (506 mL) and the solids were dried on the filter for 30 min. The solids were slurried in acetone (1237 mL) and stirred for 1 h. The resulting slurry was filtered and the solids washed with acetone (247 mL). The acetone solution was concentrated by vacuum distillation, and a constant volume (2 L) was maintained by slow addition of toluene (2983 mL) until all acetone and water had been distilled. The toluene solution was distilled to a thick yellow slurry by rotary evaporation, during which time the products precipitated as white solids. An additional portion of toluene (477 mL) was added to the mixture and stirred for 1 h. The mixture was then filtered and rinsed with toluene (179 mL) and dried under vacuum at 50° C. for 24 h to provide the title compound (104 g, 310 mmol, 55% yield) as a free-flowing, fluffy, slightly off-white solid. HPLC Method C Retention time 27.71 min.

Preparation 16: 5-Benzyl-2-(6-(4-(benzyloxy)-2-ethyl-5-fluorophenyl)-1H-indazol-3-yl)-4,5,6,7-tetrahydro-1H-imidazo[4,5-c]pyridine

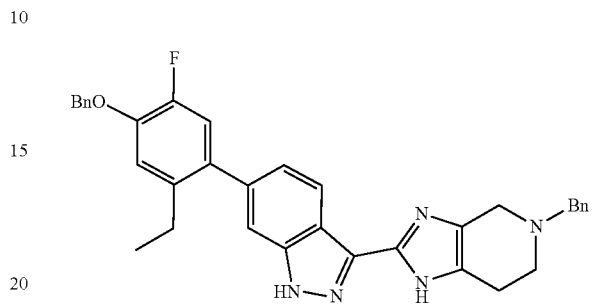

(a) 5-Benzyl-2-(6-(4-(benzyloxy)-2-ethyl-5-fluorophenyl)-1H-indazol-3-yl)-4,5,6,7-tetrahydro-1H-imidazo[4,5-c]pyridine A mixture of bis(pinacolato)diboron (250 g, 984 mmol) and IPA (1.88 L) was stirred to dissolution and then a solution of potassium hydrogen difluoride (538 g, 6.891 mol) in water (2.31 L) was added portion-wise over 10 min. The reaction mixture was stirred for 1 h and filtered. The gel-like solids were slurried with water (1.33 L) until the mixture formed a clear hydrogel and then for another 45 min. The resulting solids/gel were filtered, then reslurried in acetone (1.08 L), filtered, air dried on the filter for 30 min and dried overnight to provide a fluffy white solid (196.7 g).

To a 5 L flask was added 5-benzyl-2-(6-bromo-1H-indazol-3-yl)-4,5,6,7-tetrahydro-1H-imidazo[4,5-c]pyridine (135 g, 331 mmol), (4-(benzyloxy)-2-ethyl-5-fluorophenyl)-trifluoroborate, potassium (133 g, 397 mmol), and the white solid product of the previous step (40.5 g) followed by MeTHF (1.23 L) and MeOH (1.75 L). The resulting slurry was degassed three times with nitrogen. To the slurry was added a degassed solution of cesium carbonate (431 g, 1.323 mol) in water (1.35 L). The slurry was degassed twice, Pd (amphos)$_2$Cl$_2$ (11.71 g, 16.53 mmol) was added, the slurry was again degassed twice and the reaction mixture was stirred at 67° C. overnight and cooled to 20° C. The layers were separated and back extracted with MeTHF (550 mL). The organic layers were combined and concentrated by rotary evaporation until solids precipitated. MeTHF (700 mL) was added and the reaction mixture was stirred at 65° C. The layers were separated and the aqueous phase back extracted with MeTHF (135 mL). The organic phases were combined and concentrated to about 300 mL resulting in a thick orange slurry. To the slurry was added MeOH (270 mL) followed by 1M HCl (1.325 L) at 20° C. with rapid stirring. The reaction mixture was stirred for 5 min and water (1 L) was added and the resulting slurry was stirred for 1 h. The solids were filtered, washed with water (150 mL), dried on the filter for 10 min and at 45° C. under nitrogen for 16 h to provide the 2 HCl salt of the title compound (221.1 g, 351 mmol, 92.2% purity) as a light yellow solid. HPLC Method C retention time 23.41 min.

Preparation 17: 5-ethyl-2-fluoro-4-(3-(4,5,6,7-tetra-hydro-1H-imidazo[4,5-c]pyridin-2-yl)-1H-indazol-6-yl)phenol

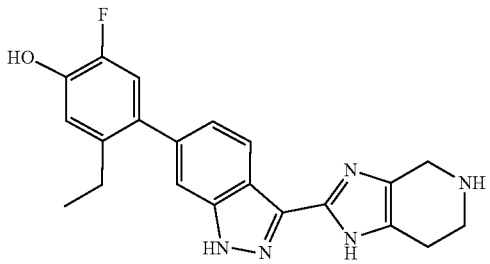 [SMILES: CCc1cc(O)c(F)cc1-c1ccc2c(-c3nc4c([nH]3)CCNC4)n[nH]c2c1]

To a 1 L flask was added 5-benzyl-2-(6-(4-(benzyloxy)-2-ethyl-5-fluorophenyl)-1H-indazol-3-yl)-4,5,6,7-tetra-hydro-1H-imidazo[4,5-c]pyridine, 2 HCl (40 g, 63.4 mmol) as a slurry in ethanol (348 mL) and 1.25 M HCl in MeOH (101 mL) and water (17.14 mL). The reaction mixture was degassed with nitrogen for 5 min and 10 wt % Pd/C, 50 wt % H$_2$O (4.05 g, 1.903 mmol) was added. The reactor was sealed, purged with HZ pressurized to 1-2 psi. warmed to 50° C., and the reaction mixture was stirred overnight and filtered through Celite. The reactor and filter were washed with methanol (100 mL).

The filtered solution was combined with the product of a second batch at the 98 mmol scale and concentrated to 390 g. EtOAc (2.04 L) was added slowly with stirring and then the solution was cooled to 5° C. with stirring. Solids were filtered, washed with EtOAc (510 mL), and dried overnight at 45° C. under nitrogen to provide the 2 HCl salt of the title compound (58 g, 80% yield) as an off-white solid. HPLC Method C retention time 12.83 min.

Example 1: 5-Ethyl-2-fluoro-4-(3-(5-(1-methylazeti-din-3-yl)-4,5,6,7-tetrahydro-1H-imidazo[4,5-c]pyri-din-2-yl)-1H-indazol-6-yl)phenol

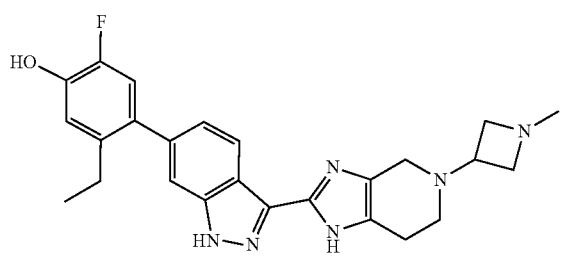 [SMILES: CCc1cc(O)c(F)cc1-c1ccc2c(-c3nc4c([nH]3)CCN(C3CN(C)C3)C4)n[nH]c2c1]

(a) 4-(3-(5-(azetidin-3-yl)-4,5,6,7-tetrahydro-1H-imidazo[4,5-c]pyridin-2-yl)-1H-indazol-6-yl)-5-ethyl-2-fluorophenol A mixture of 5-ethyl-2-fluoro-4-(3-(4,5,6,7-tetrahydro-1H-imidazo[4,5-c]pyridin-2-yl)-1H-indazol-6-yl)phenol HCl (300 mg, 0.795 mmol), tert-butyl 3-oxoazetidine-1-carboxylate (272 mg, 1.590 mmol) and acetic acid (0.137 ml, 2.385 mmol) in a mixture of THF (6 mL) and DMF (2 mL) was heated at 40° C. for 30 min. The reaction mixture was cooled to RT, treated with sodium triacetoxyborohy-dride (505 mg, 2.385 mmol), and heated at 40° C. for 2 h. The reaction mixture was combined with a parallel reaction at the 0.132 mmol scale and concentrated. The resulting residue was partitioned between EtOAc (200 mL) and saturated ammonium chloride (30 mL). The organic layer was washed with water (2×20 mL), dried over sodium sulfate, filtered, concentrated, and purified by silica gel chromatography (24 g silica gel, 0-15% MeOH/DCM). Desired fractions were combined and concentrated to give a white soft solid.

The solid was treated with 4 N HCl in 1,4-dioxane (3.97 mL) and water (1 mL) at RT for 2 h, concentrated, and freeze dried to give the HCl salt of the title intermediate (388 mg, 0.768 mmol, 83% yield) as a white solid. (m/z): [M+H]$^+$ calcd for C$_{24}$H$_{25}$FN$_6$O, 433.21 found 433.

(b) 5-Ethyl-2-fluoro-4-(3-(5-(1-methylazetidin-3-yl)-4,5,6,7-tetrahydro-1H-imidazo[4,5-c]pyridin-2-yl)-1H-indazol-6-yl)phenol To a solution of the product of the previous step (259.4 mg, 0.513 mmol) in MeOH (7 ml) at RT was added formaldehyde solution, 37% in water (0.076 mL, 1.026 mmol). The reaction mixture was stirred for 5 min and then sodium cyanoborohydride (129 mg, 2.053 mmol) was added and the mixture left overnight. The next day sodium boro-hydride (194 mg, 5.13 mmol) was added at RT. After 1 h, the reaction was quenched by the slow addition of acetic acid (5 mL) and water (2 mL). The reaction mixture was stirred for 30 min, concentrated, and additional water (3 mL) was added. The reaction mixture was filtered, purified by pre-parative HPLC, and freeze dried to provide the TFA salt of the title compound (132 mg) as a yellowish solid. (m/z): [M+H]+ calcd for C$_{25}$H$_{27}$FN$_6$O 447.22 found 447. $^1$H NMR (400 MHz, Methanol-d$_4$) δ 8.17 (dd, J=8.5, 0.9 Hz, 1H), 7.56 (dd, J=1.4, 0.8 Hz, 1H), 7.33 (dd, J=8.5, 1.4 Hz, 1H), 6.94 (d, J=11.6 Hz, 1H), 6.90 (d, J=8.9 Hz, 1H), 4.58-4.43 (m, 1H), 4.41-4.28 (m, 1H), 4.23-3.97 (m, 2H), 3.81-3.67 (m, 3H), 3.00 (s, 3H), 2.97-2.88 (m, 4H), 2.53 (q, J=7.5 Hz, 2H), 1.05 (t, J=7.5 Hz, 3H).

Example 2: 4-(3-(5-(azetidin-3-yl)-4,5,6,7-tetra-hydro-1H-imidazo[4,5-c]pyridin-2-yl)-1H-indazol-6-yl)-5-ethyl-2-fluorophenol

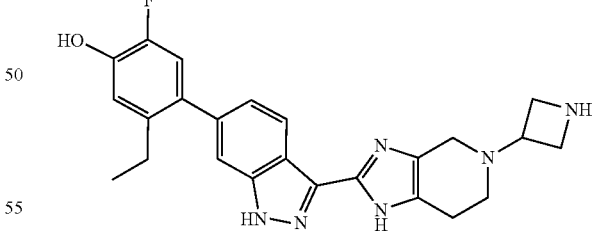

To a solution of 5-ethyl-2-fluoro-4-(3-(4,5,6,7-tetrahydro-1H-imidazo[4,5-c]pyridin-2-yl)-1H-indazol-6-yl)phenol (50 mg, 0.132 mmol) and tert-butyl 3-oxoazetidine-1-carboxy-late (68.0 mg, 0.397 mmol) in methanol (2 mL) was added sodium cyanoborohydride (50.0 mg, 0.795 mmol) and the reaction mixture was stirred at RT, dissolved in 5 mL of 2:1 acetic acid:water (5 mL) and purified by preparative HPLC. The product fractions were combined and the solvent was evaporated. To the pure dry product was added ACN (1 mL) and 4 N HCl in dioxane (1 mL). The reaction mixture was stirred at RT for 30 min concentrated and purified by preparative HPLC to provide the TFA salt of the title compound (20 mg). (m/z): [M+H]+ calcd for $C_{24}H_{25}FN_6O$, 433.21 found 433.

Example 3: 5-ethyl-2-fluoro-4-(3-(5-(1-isopropylazetidin-3-yl)-4,5,6,7-tetrahydro-1H-imidazo[4,5-c]pyridin-2-yl)-1H-indazol-6-yl)phenol

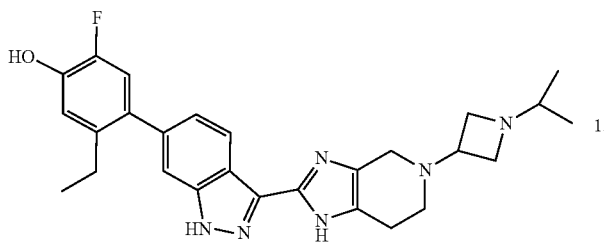

To a solution of 4-(3-(5-(azetidin-3-yl)-4,5,6,7-tetrahydro-1H-imidazo[4,5-c]pyridin-2-yl)-1H-indazol-6-yl)-5-ethyl-2-fluorophenol (15 mg, 0.035 mmol) and acetone (10.07 mg, 0.173 mmol) in MeOH (2.0 ml) was added sodium cyanoborohydride (17.44 mg, 0.277 mmol) and the reaction mixture was stirred at RT overnight, concentrated under vacuum and purified by preparative HPLC to provide the TFA salt of the title compound (10.4 mg). (m/z): [M+H]+ calcd for $C_{27}H_{31}FN_6O$, 475.25 found 475.1.

Example 4: 4-(3-(5-(1-(sec-butyl)azetidin-3-yl)-4,5,6,7-tetrahydro-1H-imidazo[4,5-c]pyridin-2-yl)-1H-indazol-6-yl)-5-ethyl-2-fluorophenol

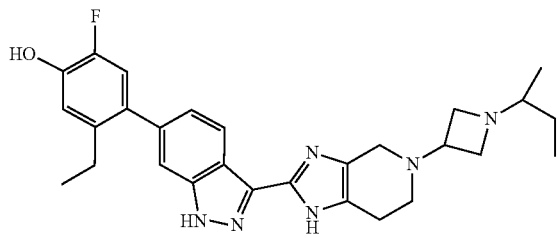 [SMILES: CCc1cc(O)c(F)cc1-c1ccc2c(-c3nc4c([nH]3)CCN(C3CN(C(C)CC)C3)C4)n[nH]c2c1]

Using a process similar to that of Example 3 at the 0.045 mmol scale with reagent 2-butanone in place of acetone, the TFA salt of the title compound (10 mg) was prepared. (m/z): [M+H]+ calcd for $C_{28}H_{33}FN_6O$, 489.27 found 489.2.

Example 5: 4-(3-(5-(1-cyclopropylazetidin-3-yl)-4,5,6,7-tetrahydro-1H-imidazo[4,5-c]pyridin-2-yl)-1H-indazol-6-yl)-5-ethyl-2-fluorophenol

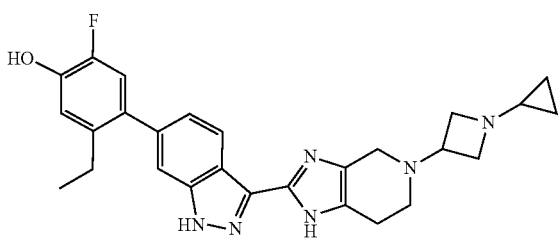 [SMILES: CCc1cc(O)c(F)cc1-c1ccc2c(-c3nc4c([nH]3)CCN(C3CN(C5CC5)C3)C4)n[nH]c2c1]

To a solution of 4-(3-(5-(azetidin-3-yl)-4,5,6,7-tetrahydro-1H-imidazo[4,5-c]pyridin-2-yl)-1H-indazol-6-yl)-5-ethyl-2-fluorophenol (349 mg, 0.807 mmol), [(1-ethoxycyclopropyl)oxy]-trimethylsilane (0.811 mL, 4.03 mmol), and acetic acid (0.185 ml, 3.23 mmol) in methanol (4.03 mL) was added sodium cyanoborohydride (507 mg, 8.07 mmol) in methanol (4.03 mL) was added. The reaction mixture was stirred at 65° C. for 2 h, concentrated by rotary evaporation, and purified by preparative HPLC. Fractions were combined to provide the TFA salt of the title compound (62 mg). (m/z): [M+H]+ calcd for $C_{27}H_{29}FN_6O$, 473.24 found 473.2.

Example 6: 5-Ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol

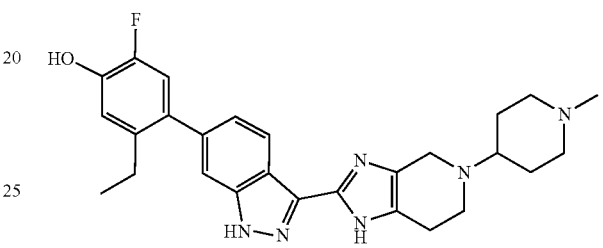

To a solution of 5-ethyl-2-fluoro-4-(3-(4,5,6,7-tetrahydro-H-imidazo[4,5-c]pyridin-2-yl)-1H-indazol-6-yl)phenol HCl (0.80 g, 1.93 mmol), acetic acid (0.33 mL, 5.80 mmol), and 1-methylpiperidin-4-one (0.29 mL, 2.32 mmol) in DMF (30 mL) was added sodium triacetoxyborohydride (1.229 g, 5.80 mmol). The reaction mixture was stirred at RT for 48 h, concentrated, and purified by preparative HPLC to provide the title compound (612 mg). (m/z): [M+H]+ calcd for $C_{27}H_{31}FN_6O$ 475.25 found 475.1. $^1$H NMR (400 MHz, Methanol-$d_4$) δ 8.19 (dd, J=8.5, 1.0 Hz, 1H), 7.51 (d, J=1.4 Hz, 1H), 7.26 (dd, J=8.5, 1.5 Hz, 1H), 6.94 (d, J=11.7 Hz, 1H), 6.89 (d, J=8.9 Hz, 1H), 4.22 (s, 2H), 3.75-3.61 (m, 2H), 3.53-3.37 (m, 4H), 3.22-3.08 (m, 1H), 3.07-3.00 (m, 2H), 2.91 (s, 3H), 2.52 (q, J=7.5 Hz, 2H), 2.43-2.30 (m, 3H), 2.19-2.01 (m, 3H), 1.05 (t, J=7.5 Hz, 3H).

Example 7: 4-(3-(5-(2-(dimethylamino)ethyl)-4,5,6,7-tetrahydro-1H-imidazo[4,5-c]pyridin-2-yl)-1H-indazol-6-yl)-5-ethyl-2-fluorophenol

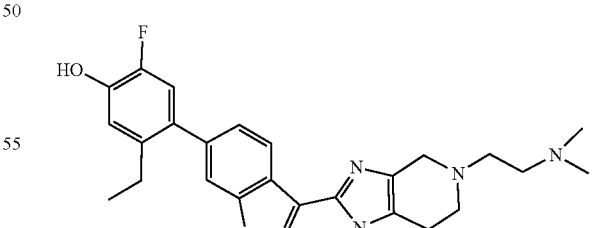

(a) tert-Butyl (2-(2-(6-(2-ethyl-5-fluoro-4-hydroxyphenyl)-1H-indazol-3-yl)-1,4,6,7-tetrahydro-5H-imidazo[4,5-c]pyridin-5-yl)ethyl)carbamate To a suspension of 5-ethyl-2-fluoro-4-(3-(4,5,6,7-tetrahydro-1H-imidazo[4,5-c]pyridin-2-yl)-1H-indazol-6-yl)

phenol HCl (600 mg, 1.45 mmol) in DMF (20 mL) were added tert-butyl (2-oxoethyl)carbamate (277 mg, 1.74 mmol) and acetic acid (0.25 mg, 4.35 mmol) followed by sodium triacetoxyborohydride (922 mg, 4.35 mmol) in portions over several min and the reaction mixture was stirred at RT for 96 h. The reaction mixture was concentrated by rotary evaporation and purified by preparative HPLC to provide the TFA salt of the title intermediate (364 mg).

(b) 4-(3-(5-(2-aminoethyl)-4,5,6,7-tetrahydro-1H-imidazo[4,5-c]pyridin-2-yl)-1H-indazol-6-yl)-5-ethyl-2-fluorophenol To the product of the previous step (364 mg, 0.57 mmol) were added 4 M HCl in dioxane (3 mL) and water (0.1 mL). The reaction mixture was stirred at RT for 30 min, concentrated by rotary evaporation, evaporated with EtOAc (3×5 mL) by rotary evaporation, and dried under high vacuum to provide the HCl salt of the title intermediate (283 mg) which was used directly in the next step.

(c) 4-(3-(5-(2-(dimethylamino)ethyl)-4,5,6,7-tetrahydro-1H-imidazo[4,5-c]pyridin-2-yl)-1H-indazol-6-yl)-5-ethyl-2-fluorophenol To a solution of the product of the previous step (283 mg) in MeOH (11 mL) at RT was added formaldehyde solution, 37% in water (0.171 mL, 2.30 mmol). The reaction mixture was stirred for 5 min and then sodium cyanoborohydride (252 mg, 4.02 mmol) was added. One hour 15 min later, sodium borohydride (152 mg, 4.02 mmol) was added. After 1 h, the reaction mixture was concentrated by rotary evaporation and purified by preparative HPLC to provide the TFA salt of the title compound (141 mg) as a yellow powder. (m/z): [M+H]$^+$ calcd for C$_{25}$H$_{29}$FN$_6$O 449.24 found 449. $^1$H NMR (400 MHz, Methanol-d$_4$) δ 8.16 (dd, J=8.5, 0.9 Hz, 1H), 7.55 (d, J=1.3 Hz, 1H), 7.32 (dd, J=8.4, 1.4 Hz, 1H), 6.94 (d, J=11.6 Hz, 1H), 6.90 (d, J=9.0 Hz, 1H), 3.89 (s, 2H), 3.40 (dd, J=6.5, 5.0 Hz, 2H), 3.12 (t, J=5.7 Hz, 2H), 3.06 (t, J=5.8 Hz, 2H), 2.98-2.86 (m, 8H), 2.52 (q, J=7.5 Hz, 2H), 1.05 (t, J=7.5 Hz, 3H).

Example 8: 5-Ethyl-2-fluoro-4-(3-(5-(2-((3-methoxycyclobutyl)amino)ethyl)-4,5,6,7-tetrahydro-1H-imidazo[4,5-c]pyridin-2-yl)-1H-indazol-6-yl)phenol

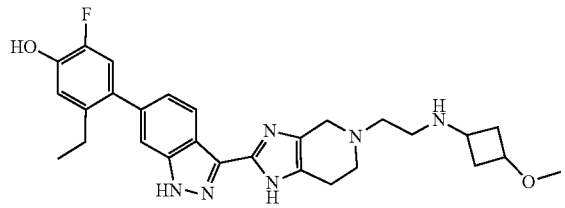 [SMILES: CCc1cc(O)c(F)cc1-c1ccc2c(-c3nc4c([nH]3)CCN(CCNC3CC(OC)C3)C4)n[nH]c2c1]

(a) tert-Butyl (2-(2-(6-(2-ethyl-5-fluoro-4-hydroxyphenyl)-1H-indazol-3-yl)-1,4,6,7-tetrahydro-5H-imidazo[4,5-c]pyridin-5-yl)ethyl)carbamate To a suspension of 5-ethyl-2-fluoro-4-(3-(4,5,6,7-tetrahydro-1H-imidazo[4,5-c]pyridin-2-yl)-1H-indazol-6-yl)phenol HCl (600 mg, 1.45 mmol) in DMF (20 mL) were added tert-butyl (2-oxoethyl)carbamate (277 mg, 1.74 mmol) and acetic acid (0.25 mg, 4.35 mmol) followed by sodium triacetoxyborohydride (922 mg, 4.35 mmol) in portions over several min and the reaction mixture was stirred at RT for 96 h. The reaction mixture was concentrated and purified by preparative HPLC (10-70% ACN/Water). to provide the TFA salt of the title intermediate (507 mg).

(b) 4-(3-(5-(2-aminoethyl)-4,5,6,7-tetrahydro-1H-imidazo[4,5-c]pyridin-2-yl)-1H-indazol-6-yl)-5-ethyl-2-fluorophenol The product of the previous step (505 mg, 0.80 mmol) was dissolved in dioxane (8 mL) and water (1.6 mL) and then 4 M HCl in dioxane (8 mL, 32 mmol) was added. The reaction mixture was stirred at RT for 20 min, frozen, and lyophilized to provide the HCl salt of the title intermediate which was used directly in the next step.

(c) 5-Ethyl-2-fluoro-4-(3-(5-(2-((3-methoxycyclobutyl)amino)ethyl)-4,5,6,7-tetrahydro-1H-imidazo[4,5-c]pyridin-2-yl)-1H-indazol-6-yl)phenol The product of the previous step (393 mg, 0.80 mmol) and acetic acid (0.14 mL, 2.39 mmol) were dissolved in DMF (10 mL), then 3-methoxycyclobutan-1-one (0.094 mL, 0.88 mmol) was added. The reaction mixture was stirred at RT for 30 min and sodium triacetoxyborohydride (507 mg, 2.39 mmol) was added. The reaction mixture was stirred at RT overnight, concentrated and purified by preparative HPLC to provide the TFA salt of the title intermediate (56 mg). (m/z): [M+H]$^+$ calcd for C$_2$H$_{33}$FN$_6$O$_2$ 505.26 found 505.3.

Example 9: 5-ethyl-4-(3-(5-(2-(ethyl(methyl)amino)ethyl)-4,5,6,7-tetrahydro-1H-imidazo[4,5-c]pyridin-2-yl)-1H-indazol-6-yl)-2-fluorophenol

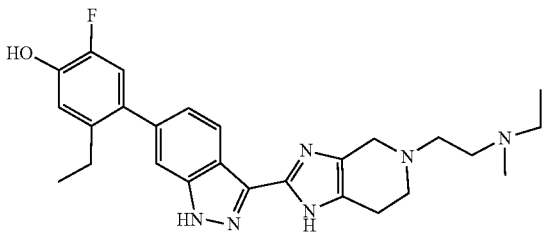 [SMILES: CCc1cc(O)c(F)cc1-c1ccc2c(-c3nc4c([nH]3)CCN(CCN(C)CC)C4)n[nH]c2c1]

(a) tert-butyl (2-(2-(6-(2-ethyl-5-fluoro-4-hydroxyphenyl)-1H-indazol-3-yl)-1,4,6,7-tetrahydro-5H-imidazo[4,5-c]pyridin-5-yl)ethyl)(methyl)carbamate Acetic acid (0.166 mL, 2.90 mmol), tert-butyl methyl(2-oxoethyl)carbamate (201 mg, 1.160 mmol), and 5-ethyl-2-fluoro-4-(3-(4,5,6,7-tetrahydro-1H-imidazo[4,5-c]pyridin-2-yl)-1H-indazol-6-yl)phenol, HCl (400 mg, 0.966 mmol) were combined in DMF (3.65 mL). Sodium triacetoxyborohydride (615 mg, 2.90 mmol) was added portion wise over five minutes. The reaction mixture was stirred overnight and diluted with EtOAc (50 mL). The organic solution was washed with sat. NaHCO$_3$ (2×20 mL). The organic phase was collected, dried (MgSO4), and concentrated under vacuum. The crude residue was purified by silica gel chromatography (0% to 15% MeOH in DCM). Pure fractions were combined and concentrated to provide the title intermediate (491 mg) as a colorless, amorphous solid. (m/z): [M+H]+ calcd for $C_{29}H_{35}FN_6O_3$ 535.28 found 536.

(b) 5-ethyl-2-fluoro-4-(3-(5-(2-(methylamino)ethyl)-4,5,6,7-tetrahydro-1H-imidazo[4,5-c]pyridin-2-yl)-1H-indazol-6-yl)phenol The product of the previous step (0.491 g, 0.918 mmol) was dissolved in dioxane (4.59 mL) and water (4.59 mL) and 4 N HCl in dioxane (4.59 mL, 18.36 mmol) was added slowly over 5 min. The reaction mixture was stirred for 1 h, diluted with water (20 mL), freeze dried at −78° C., and lyophilized to provide the di-HCL salt of the title intermediate (413 mg).

(c) 5-ethyl-4-(3-(5-(2-(ethyl(methyl)amino)ethyl)-4,5,6,7-tetrahydro-1H-imidazo[4,5-c]pyridin-2-yl)-1H-indazol-6-yl)-2-fluorophenol To the product of the previous step (0.2 g, 0.394 mmol) dissolved in MeOH (1.971 mL) was added acetaldehyde (0.11 mL, 1.971 mmol) followed by sodium cyanoborohydride (248 mg, 3.94 mmol). The reaction mixture was stirred overnight, dissolved in 2:1 acetic acid:water, syringe filtered, and purified by preparative HPLC. Pure fractions were combined and lyophilized to provide the TFA salt of the title compound (25 mg). (m/z): [M+H]+ calcd for $C_{26}H_{31}FN_6O_3$ 436.28 found 436.2.

Example 10: 4-(3-(5-(2-(sec-butyl(methyl)amino)ethyl)-4,5,6,7-tetrahydro-1H-imidazo[4,5-c]pyridin-2-yl)-1H-indazol-6-yl)-5-ethyl-2-fluorophenol

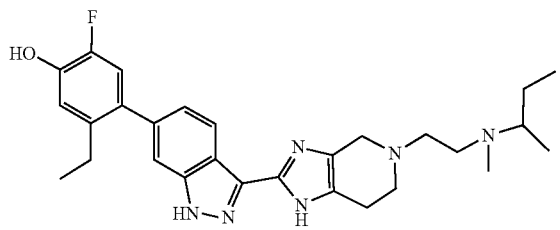 [SMILES: CCc1cc(O)c(F)cc1-c1ccc2c(-c3nc4c([nH]3)CCN(CCN(C)C(C)CC)C4)n[nH]c2c1]

Following the general procedure of Example 9 using butan-2-one (0.177 mL, 1.971 mmol) in place of acetaldehyde in step (c) the TFA salt of the title compound was prepared (66 mg). (m/z): [M+H]+ calcd for $C_2H_{35}FN_6O_3$ 491.29 found 492.

Example 11: (S)-5-ethyl-2-fluoro-4-(3-(5-((1-methylpyrrolidin-2-yl)methyl)-4,5,6,7-tetrahydro-1H-imidazo[4,5-c]pyridin-2-yl)-1H-indazol-6-yl)phenol

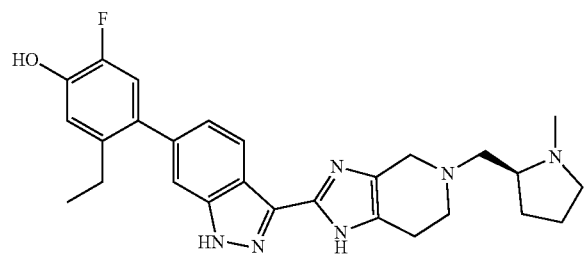 [SMILES: CCc1cc(O)c(F)cc1-c1ccc2c(-c3nc4c([nH]3)CCN(C[C@@H]3CCCN3C)C4)n[nH]c2c1]

(a) tert-butyl (S)-2-((2-(6-(2-ethyl-5-fluoro-4-hydroxyphenyl)-1H-indazol-3-yl)-1,4,6,7-tetrahydro-5H-imidazo[4,5-c]pyridin-5-yl)methyl)pyrrolidine-1-carboxylate To a suspension of 5-ethyl-2-fluoro-4-(3-(4,5,6,7-tetrahydro-1H-imidazo[4,5-c]pyridin-2-yl)-1H-indazol-6-yl)phenol (50 mg, 0.132 mmol) and (S)-tert-butyl 2-formylpyrrolidine-1-carboxylate (34.3 mg, 0.172 mmol) in methanol (1.34 mL) was added sodium cyanoborohydride (33.3 mg, 0.530 mmol) and the reaction mixture was stirred at 25° C. overnight. Additional sodium cyanoborohydride (33.3 mg, 0.530 mmol) was added and the reaction mixture was heated at 70° C. for 30 min. The following day, two additional portions of (S)-tert-butyl 2-formylpyrrolidine-1-carboxylate (34.3 mg, 0.172 mmol) were added, each followed by heating added at 70° C. for 1 h. The reaction mixture was dissolved in 8:2 DCM:methanol (8 mL) and purified by silica gel chromatography (100% DCM 15 min, 0-5% DCM:methanol, 20 min, 5% DCM:methanol, 20 min). Fractions were combined and concentrated to provide the title intermediate as a white waxy solid (167 mg). (m/z): [M+H]+ calcd for $C_{31}H_{37}FN_6O_3$ 561.29 found 561.3.

(b) (S)-5-ethyl-2-fluoro-4-(3-(5-(pyrrolidin-2-ylmethyl)-4,5,6,7-tetrahydro-1H-imidazo[4,5-c]pyridin-2-yl)-1H-indazol-6-yl)phenol To the product of the previous step (167 mg, 0.298 mmol) was added DCM (14.9 mL) followed by TFA (14.9 mL) and the reaction mixture was stirred for 1 h, concentrated, and dissolved in 4:1 water:acetic acid (8 mL) with 8 drops of methanol and purified by preparative HPLC. Fractions were combined and concentrated to provide the TFA salt of the title intermediate (70 mg) as a glassy white solid. (m/z): [M+H]+ calcd for $C_{26}H_{29}FN_6O$, 461.24 found 461.1.

(c) S)-5-ethyl-2-fluoro-4-(3-(5-((1-methylpyrrolidin-2-yl)methyl)-4,5,6,7-tetrahydro-1H-imidazo[4,5-c]pyridin-2-yl)-1H-indazol-6-yl)phenol To a solution of the product of the previous step (70 mg, 0.152 mmol) and formaldehyde solution 37% in water (0.023 mL, 0.304 mmol) in methanol (15.2 mL) was added sodium cyanoborohydride (38.2 mg, 0.608 mmol) and the reaction mixture was stirred at 25° C. overnight. An additional portion of formaldehyde (0.023 mL, 0.304 mmol) was added and the reaction mixture was stirred at 25° C. overnight and concentrated. Methanol (1.52 mL) and sodium cyanoborohydride (382 mg, 6.08 mmol) were added; the reaction mixture was stirred for 3 h; additional sodium cyanoborohydride (382 mg, 6.08 mmol) was added; the reaction mixture was stirred at 25° C. over the weekend; concentrated; dissolved 1:1 acetic acid:water (4 mL), filtered and purified by preparative HPLC to provide the TFA salt of the title compound (36.4 mg). (m/z): [M+H]+ calcd for $C_{27}H_{31}FN_6O$, 475.25 found 475.2.

Example 12: 4-(3-(5-(3-(dimethylamino)-2-fluoropropyl)-4,5,6,7-tetrahydro-1H-imidazo[4,5-c]pyridin-2-yl)-1H-indazol-6-yl)-5-ethyl-2-fluorophenol

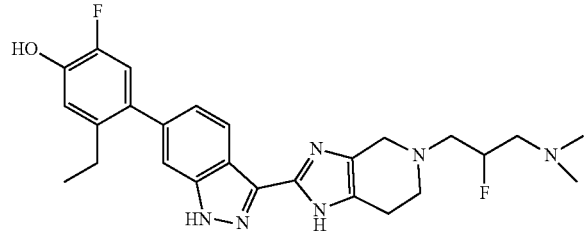 [SMILES: CCc1cc(O)c(F)cc1-c1ccc2c(-c3nc4c([nH]3)CCN(CC(F)CN(C)C)C4)n[nH]c2c1]

(a) tert-butyl (3-(2-(6-(2-ethyl-5-fluoro-4-hydroxyphenyl)-1H-indazol-3-yl)-1,4,6,7-tetrahydro-5H-imidazo[4,5-c]pyridin-5-yl)-2-fluoropropyl)carbamate To a solution of DIPEA (0.505 mL, 2.90 mmol) and 5-ethyl-2-fluoro-4-(3-(4,5,6,7-tetrahydro-1H-imidazo[4,5-c]pyridin-2-yl)-1H-indazol-6-yl)phenol, HCl (400 mg, 0.966 mmol) in DMF (2.416 mL) was added dropwise a solution of tert-butyl (3-bromo-2-fluoropropyl)carbamate (248 mg, 0.966 mmol) in DMF (2.416 mL). The reaction mixture was stirred at RT overnight. Additional tert-butyl (3-bromo-2-fluoropropyl)carbamate (248 mg, 0.966 mmol) was added and the reaction mixture was stirred overnight, concentrated under vacuum, and purified by silica gel chromatography (MeOH:DCM) to provide the title intermediate (286 mg, 0.518 mmol, 54% yield). (m/z): [M+H]$^+$ calcd for $C_{29}H_{34}F_2N_6O_3$ 553.27 found 553.

(b) 4-(3-(5-(3-amino-2-fluoropropyl)-4,5,6,7-tetrahydro-1H-imidazo[4,5-c]pyridin-2-yl)-1H-indazol-6-yl)-5-ethyl-2-fluorophenol The product of the previous step (0.286 g, 0.518 mmol) was dissolved in dioxane (2.15 mL) and water (0.48 mL) and 4 M HCl in dioxane (2.15 mL, 8.60 mmol) was added slowly over 5 min and the reaction mixture was stirred at RT for 30 min, frozen, and lyophilized to provide the HCl salt of the title intermediate (261 mg). (m/z): [M+H]$^+$ calcd for $C_{24}H_{26}F_2N_6O$, 453.21 found 453.

(c) 4-(3-(5-(3-(dimethylamino)-2-fluoropropyl)-4,5,6,7-tetrahydro-1H-imidazo[4,5-c]pyridin-2-yl)-1H-indazol-6-yl)-5-ethyl-2-fluorophenol The product of the previous step (0.261 g, 0.497 mmol) and formaldehyde solution 37% in water (0.083 mL, 1.043 mmol) were combined in MeOH (4.97 mL). Sodium cyanoborohydride (0.156 g, 2.484 mmol) was added and the reaction mixture was stirred at RT for several hours. Sodium borohydride was added. The reaction mixture was concentrated and purified by preparative HPLC. Pure fractions were combined and lyophilized to provide the TFA salt of the title compound (30 mg). (m/z): [M+H]$^+$ calcd for $C_{26}H_{30}F_2N_6O$, 481.24 found 481.

Example 13: (S)-5-Ethyl-2-fluoro-4-(3-(5-(morpholin-3-ylmethyl)-4,5,6,7-tetrahydro-1H-imidazo[4,5-c]pyridin-2-yl)-1H-indazol-6-yl)phenol

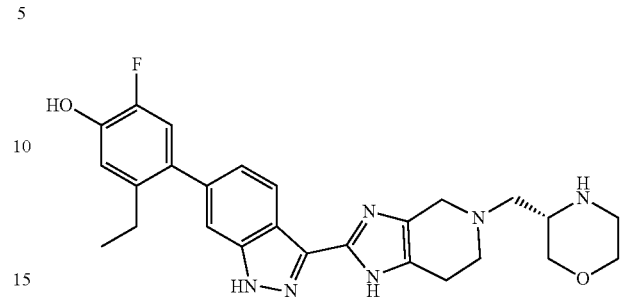

To a solution of 5-ethyl-2-fluoro-4-(3-(4,5,6,7-tetrahydro-1H-imidazo[4,5-c]pyridin-2-yl)-1H-indazol-6-yl)phenol TFA (100 mg, 0.203 mmol) and tert-butyl (R)-3-formylmorpholine-4-carboxylate (285 mg, 1.325 mmol) in MeOH (5 mL), was added sodium cyanoborohydride (167 mg, 2.65 mmol) and the reaction mixture was stirred at RT overnight.

The reaction mixture was concentrated and TFA (3 mL) was added at 0° C. After 30 min, the reaction mixture was concentrated and purified by preparative HPLC (2-70% ACN/Water) to provide the TFA salt of the title compound (55.2 mg). (m/z): [M+H]$^+$ calcd for $C_{26}H_{29}FN_6O_2$ 477.23 found 477.1. $^1$H NMR (400 MHz, Methanol-d$_4$) δ 8.16 (dd, J=8.5, 0.9 Hz, 1H), 7.55 (d, J=1.2 Hz, 1H), 7.31 (dd, J=8.5, 1.4 Hz, 1H), 6.94 (d, J=11.6 Hz, 1H), 6.90 (d, J=9.0 Hz, 1H), 4.04 (ddd, J=15.8, 12.7, 3.4 Hz, 2H), 3.97-3.72 (m, 4H), 3.66 (td, J=8.2, 7.3, 3.1 Hz, 1H), 3.57 (dd, J=12.5, 9.1 Hz, 1H), 3.35-3.32 (m, 1H), 3.28-3.12 (m, 2H), 3.07-2.96 (m, 1H), 2.96-2.90 (m, 2H), 2.88 (d, J=7.3 Hz, 2H), 2.52 (q, J=7.5 Hz, 2H), 1.05 (t, J=7.5 Hz, 3H).

Example 14: (R)-5-Ethyl-2-fluoro-4-(3-(5-(morpholin-3-ylmethyl)-4,5,6,7-tetrahydro-1H-imidazo[4,5-c]pyridin-2-yl)-1H-indazol-6-yl)phenol

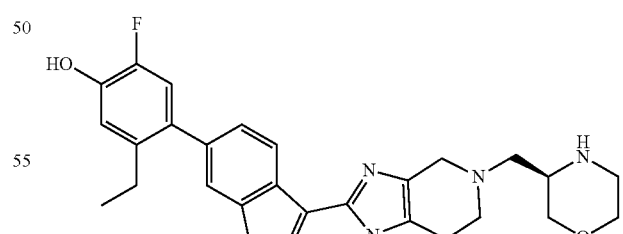

Using a process similar to that of Example 13 at the 0.159 mmol scale, the TFA salt of the title compound (29.1 mg) was prepared. (m/z): [M+H]$^+$ calcd for $C_{26}H_{29}FN_6O_2$ 477.23 found 477.1.

Example 15: (S)-5-ethyl-2-fluoro-4-(3-(5-(2-(2-methylpyrrolidin-1-yl)ethyl)-4,5,6,7-tetrahydro-1H-imidazo[4,5-c]pyridin-2-yl)-1H-indazol-6-yl)phenol

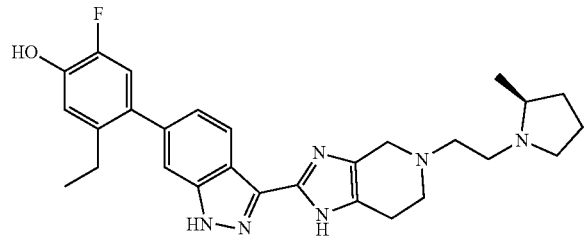 [SMILES: CCc1cc(O)c(F)cc1-c1ccc2c(-c3nc4c([nH]3)CCN(CCN3CCC[C@@H]3C)C4)n[nH]c2c1]

(a) 4-(3-(5-(2,2-dimethoxyethyl)-4,5,6,7-tetrahydro-1H-imidazo[4,5-c]pyridin-2-yl)-1H-indazol-6-yl)-5-ethyl-2-fluorophenol To a mixture of 5-ethyl-2-fluoro-4-(3-(4,5,6,7-tetrahydro-1H-imidazo[4,5-c]pyridin-2-yl)-1H-indazol-6-yl)phenol HCl (200 mg, 0.483 mmol) and 2,2-dimethoxyacetaldehyde (0.146 mL, 0.966 mmol) in MeOH (4.83 mL) was added sodium cyanoborohydride (121 mg, 1.933 mmol) and the reaction mixture was stirred overnight at RT, concentrated, and purified by silica gel chromatography (10% MeOH in DCM) to provide the title intermediate, (210 mg). (m/z): [M+H]$^+$ calcd for $C_{25}H_{28}FN_5O_3$ 466.22 found 466.

(b) 2-(2-(6-(2-ethyl-5-fluoro-4-hydroxyphenyl)-1H-indazol-3-yl)-1,4,6,7-tetrahydro-5H-imidazo[4,5-c]pyridin-5-yl)ethane-1,1-diol The product of the previous step (210 mg, 0.0.451 mmol) was dissolved in MeTHF (4 mL) and 3 N HCl in water (4 mL, 12 mmol) was added. The reaction mixture was stirred for 4 d, concentrated, dissolved in 1:1 acetic acid: water, and purified by preparative HPLC. Pure fractions were combined and lyophilized to provide the title intermediate (150 mg) (m/z): [M+H]$^+$ calcd for $C_{23}H_{24}FN_5O_3$ 438.19 found 438.

(c) (S)-5-ethyl-2-fluoro-4-(3-(5-(2-(2-methylpyrrolidin-1-yl)ethyl)-4,5,6,7-tetrahydro-1H-imidazo[4,5-c]pyridin-2-yl)-1H-indazol-6-yl)phenol To a mixture of the product of the previous step (20 mg, 0.046 mmol) and (S)-2-methylpyrrolidine (19 mg, 0.229 mmol) in MeOH (0.5 mL) was added sodium cyanoborohydride (28.7 mg, 0.457 mmol) in MeOH (0.5 mL). The reaction mixture was stirred overnight, dissolved in 2:1 acetic acid: water and purified by preparative HPLC to provide the TFA salt of the title compound (6 mg, 0.0084 mmol, 18% yield). (m/z): [M+H]$^+$ calcd for $C_{28}H_{33}FN_6O$, 489.27 found 489.2.

Example 16: 5-Ethyl-2-fluoro-4-(3-(5-(2-(pyrrolidin-1-yl)ethyl)-4,5,6,7-tetrahydro-1H-imidazo[4,5-c]pyridin-2-yl)-1H-indazol-6-yl)phenol

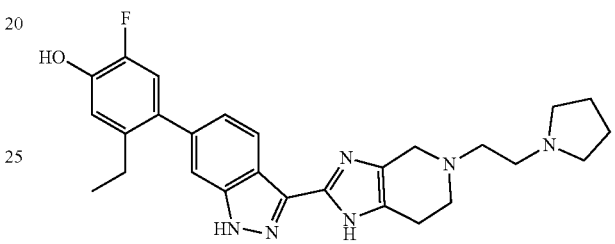

To a solution of 5-ethyl-2-fluoro-4-(3-(4,5,6,7-tetrahydro-1H-imidazo[4,5-c]pyridin-2-yl)-1H-indazol-6-yl)phenol (30 mg, 0.079 mmol) in DMF (500 µL) was added 1-(2-bromoethyl)pyrrolidine (21.23 mg, 0.119 mmol) and DIPEA (69.2 µL, 0.397 mmol). The reaction mixture was capped and stirred at RT for 1 h, concentrated, dissolved in 1:1 acetic acid:water, and purified by preparative HPLC to provide the TFA salt of the title compound (18 mg, 0.026 mm, 32% yield). (m/z): [M+H]$^+$ calcd for $C_{27}H_3FN_6O$, 475.25 found 475.2.

Using similar synthetic methods, the compounds of Tables 1-19 were prepared. In the following tables, a blank in any column indicates a hydrogen atom, a * in a structure heading a table indicates a chiral center, and the notation (R) or (S) in front of a substituent denotes the configuration of the carbon atom to which the substituent is attached.

TABLE 1

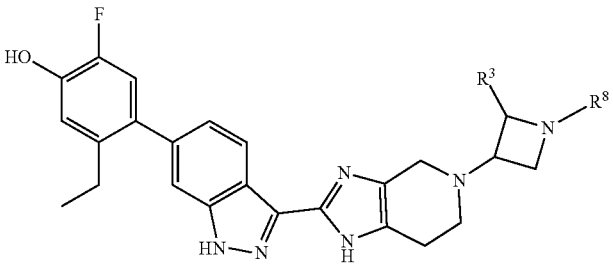

| Ex No. | R$^8$ | R$^3$ | Formula | Calc [M + H]$^+$ | Found [M + H]$^+$ |
|---|---|---|---|---|---|
| 1-1 | —(CH$_2$)$_2$OH | | C$_{26}$H$_{29}$FN$_6$O$_2$ | 477.23 | 477.2 |
| 1-2 | | —CH$_3$ | C$_{25}$H$_{27}$FN$_6$O | 447.22 | 447 |
| 1-3 | —C$_2$H$_5$ | | C$_{26}$H$_{29}$FN$_6$O | 461.24 | 461.2 |
| 1-4 | —(CH$_2$)$_3$SCH$_3$ | | C$_{28}$H$_{33}$FN$_6$OS | 521.24 | 521.2 |

TABLE 1-continued

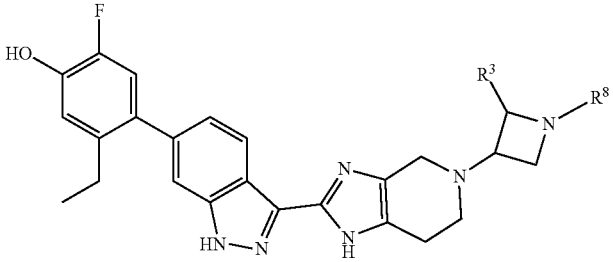

| Ex No. | R⁸ | R³ | Formula | Calc [M + H]⁺ | Found [M + H]⁺ |
|---|---|---|---|---|---|
| 1-5 |  | | $C_{29}H_{30}FN_7O$ | 512.25 | 512.3 |
| 1-6 | —(CH₂)₂OCH₃ | | $C_{27}H_{31}FN_6O_2$ | 491.25 | 491.1 |
| 1-7 | —(CH₂)₃OCH₃ | | $C_{28}H_{33}FN_6O_2$ | 505.27 | 505.2 |
| 1-8 | —(CH₂)₂CN | | $C_{27}H_{28}FN_7O$ | 486.23 | 486.1 |
| 1-9 | —(CH₂)₂SCH₃ | | $C_{27}H_{31}FN_6OS$ | 507.23 | 507.2 |
| 1-10 | cBu | | $C_{28}H_{31}FN_6O$ | 487.25 | 487.2 |
| 1-11 | —CH₂iPr | | $C_{28}H_{33}FN_6O$ | 489.27 | 489.2 |
| 1-12 | oxetan-3-yl | | $C_{27}H_{29}FN_6O_2$ | 489.23 | 489.1 |
| 1-13 | —(CH₂)₂CH(CH₃)SCH₃ | | $C_{29}H_{35}FN_6OS$ | 535.26 | 535.1 |
| 1-14 | —CH₃ | —CH₃ | $C_{26}H_{29}FN_6O$ | 461.24 | 461 |
| 1-15 | 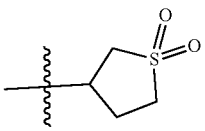 [SMILES: *C1CCS(=O)(=O)C1] | | $C_{28}H_{31}FN_6O_3S$ | 551.22 | 551.1 |
| 1-16 | tetrahydropyran-4-yl | | $C_{29}H_{33}FN_6O_2$ | 517.27 | 517.3 |
| 1-17 | 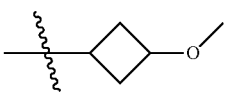 [SMILES: *C1CC(OC)C1] | | $C_{29}H_{33}FN_6O_2$ | 517.27 | 517.2 |
| 1-18 | —CH₂cPr | | $C_{28}H_{31}FN_6O$ | 487.25 | 487.2 |

TABLE 2

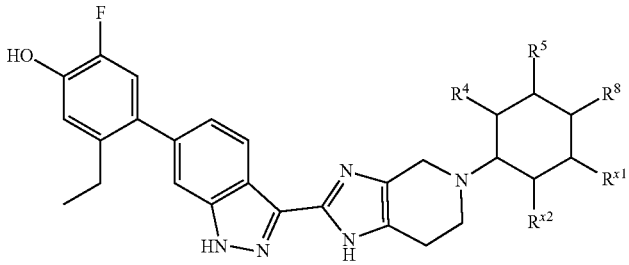

| Ex. No. | R⁸ | R⁴, R⁵, R^{x1}, R^{x2} | Formula | Calc [M + H]⁺ | Found [M + H]⁺ |
|---|---|---|---|---|---|
| 2-1 | —CH₃ | R⁵ = —C(O)OCH₃ | $C_{29}H_{33}FN_6O_3$ | 533.26 | 533 |
| 2-2 | | R⁴ = —C(O)OC₂H₅ | $C_{29}H_{33}FN_6O_3$ | 533.26 | 533.1 |
| 2-3 | | | $C_{26}H_{29}FN_6O$ | 461.24 | 461.2 |
| 2-4 | | R⁵ = (R)CH₃ | $C_{27}H_{31}FN_6O$ | 475.25 | 475.2 |
| 2-5 | | R⁵ = (R)CH₃<br>R^{x1} = (R)CH₃ | $C_{28}H_{33}FN_6O$ | 489.27 | 489 |
| 2-6 | cBu | | $C_{30}H_{35}FN_6O$ | 515.29 | 515.2 |
| 2-7 | —CH₂iPr | | $C_{30}H_{37}FN_6O$ | 517.30 | 517.2 |

TABLE 2-continued

| Ex. No. | $R^8$ | $R^4, R^5, R^{x1}, R^{x2}$ | Formula | Calc [M + H]$^+$ | Found [M + H]$^+$ |
|---|---|---|---|---|---|
| 2-8 | (3-oxo-1λ⁶-thiolan-1,1-dioxide-3-yl) |  | $C_{30}H_{35}FN_6O_3S$ | 579.25 | 579.2 |
| 2-9 | oxetan-3-yl |  | $C_{29}H_{33}FN_6O_2$ | 517.27 | 517.2 |
| 2-10 | —CH$_2$-phenyl |  | $C_{33}H_{35}FN_6O$ | 551.29 | 551.2 |
| 2-11 | —(CH$_2$)$_2$CN |  | $C_{29}H_{32}FN_7O$ | 514.27 | 514.2 |
| 2-12 | tetrahydropyran-4-yl |  | $C_{31}H_{37}FN_6O_2$ | 545.30 | 545.3 |
| 2-13 | cPr |  | $C_{29}H_{33}FN_6O$ | 501.27 | 501.2 |
| 2-14 | oxetan-3-yl | $R^4$ and $R^{x2}$ form —(CH$_2$)$_2$— | $C_{31}H_{34}F_2N_6O_2$ | 561.27 | 561.2 |
| 2-15 | tetrahydropyran-4-yl | $R^4$ and $R^{x2}$ form —(CH$_2$)$_2$— | $C_{33}H_{38}F_2N_6O_2$ | 589.30 | 589.2 |
| 2-16 | —CH$_2$iPr | $R^4$ and $R^{x2}$ form —(CH$_2$)$_2$— | $C_{32}H_{36}F_2N_6O$ | 559.29 | 559.2 |
| 2-17 | (3-methoxycyclobutyl) | $R^4$ and $R^{x2}$ form —(CH$_2$)$_2$ | $C_{33}H_{38}F_2N_6O_2$ | 589.30 | 589.2 |
| 2-18 | —C$_2$H$_5$ |  | $C_{28}H_{33}FN_6O$ | 489.27 | 489.2 |
| 2-19 | —CH$_2$CH$_2$F |  | $C_{28}H_{32}F_2N_6O$ | 507.26 | 507.3 |
| 2-20 | iPr |  | $C_{29}H_{35}FN_6O$ | 503.29 | 503.3 |

TABLE 3

| Ex No. | $R^8$ | $R^2, R^3, R^4, R^7$ | * | Formula | Calc [M + H]$^+$ | Found [M + H]$^+$ |
|---|---|---|---|---|---|---|
| 3-1 | (1-cyanocyclopropyl-1-methyl) |  |  | $C_{27}H_{28}FN_7O$ | 486.23 | 486.1 |
| 3-2 | cBu | $R^7 = $ —CH$_3$ |  | $C_{28}H_{33}FN_6O$ | 489.27 | 489.2 |
| 3-3 | iPr | $R^7 = $ —CH$_3$ |  | $C_{27}H_{33}FN_6O$ | 477.27 | 477.2 |
| 3-4 | —CH$_3$ | $R^3 = $ —CH$_3$ $R^4 = $ —CH$_3$ $R^7 = $ —CH$_3$ |  | $C_{27}H_{33}FN_6O$ | 477.27 | 477.1 |
| 3-5 | —CH$_3$ | $R^3 = $ —CH$_3$ $R^7 = $ —CH$_3$ | (S) | $C_{26}H_{31}FN_6O$ | 463.25 | 463.2 |

TABLE 3-continued

| # | R (structure/group) | Other | Formula | Calc. | Found |
|---|---|---|---|---|---|
| 3-6 | cyclopropyl-CH₂OH (1-methyl) | | $C_{27}H_{31}FN_6O_2$ | 491.25 | 491.2 |
| 3-7 | | | $C_{23}H_{25}FN_6O$ | 421.21 | 421.1 |
| 3-8 | —CH₃ | $R^2$ and $R^3$ form —(CH₂)₃— $R^7$ = —CH₃ | $C_{28}H_{33}FN_6O$ | 489.27 | 489.2 |
| 3-9 | | $R^3$ = —CH₃ (S) | $C_{24}H_{27}FN_6O$ | 435.22 | 435 |
| 3-10 | —(CH₂)₂SCH₃ | | $C_{26}H_{31}FN_6OS$ | 495.23 | 495.1 |
| 3-11 | cBu | | $C_{27}H_{31}FN_6O$ | 475.25 | 475.2 |
| 3-12 | —(CH₂)₃SCH₃ | | $C_{27}H_{33}FN_6OS$ | 509.24 | 509.1 |
| 3-13 | —(CH₂)₂CN | | $C_{26}H_{28}FN_7O$ | 474.23 | 474.1 |
| 3-14 | 1-methylcyclobutyl-CH₂ | | $C_{29}H_{35}FN_6O$ | 503.29 | 503.2 |
| 3-15 | —C₂H₅ | | $C_{25}H_{29}FN_6O$ | 449.24 | 449.2 |
| 3-16 | —CH₃ | | $C_{24}H_{27}FN_6O$ | 435.22 | 435.1 |
| 3-17 | | $R^3$ = —CH₃ $R^4$ = —CH₃ | $C_{25}H_{29}FN_6O$ | 449.24 | 449.1 |
| 3-18 | —(CH₂)₂CH(CH₃)SCH₃ | | $C_{28}H_{35}FN_6OS$ | 523.26 | 523.2 |
| 3-19 | | $R^3$ = —CH((R)CH₃)OH (R) | $C_{25}H_{29}FN_6O_2$ | 465.23 | 465 |
| 3-20 | cyclobutyl-OH | | $C_{27}H_{31}FN_6O_2$ | 491.25 | 491.2 |
| 3-21 | | $R^2$ = —CH₃ $R^4$ = —CH₃ | $C_{25}H_{29}FN_6O$ | 449.24 | 449.2 |
| 3-22 | cyclobutyl-OCH₃ | $R^7$ = —CH₃ | $C_{29}H_{35}FN_6O_2$ | 519.28 | 519 |
| 3-23 | cyclobutyl-CHF₂ | | $C_{28}H_{31}F_3N_6O$ | 525.25 | 525.2 |
| 3-24 | methylcyclobutyl | | $C_{28}H_{33}FN_6O$ | 489.27 | 489.2 |
| 3-25 | cyclobutyl-CN | | $C_{28}H_{30}FN_7O$ | 500.25 | 500.2 |
| 3-26 | cyclobutyl-CH₂OCH₃ | | $C_{29}H_{35}FN_6O_2$ | 519.28 | 519.2 |
| 3-27 | —CH₂C(CH₃)₂CH₂OC₂H₅ | | $C_{30}H_{39}FN_6O_2$ | 535.31 | 535.3 |
| 3-28 | —CH₃ | $R^3$ = (R)CH₂OH $R^7$ = —CH₃ | $C_{26}H_{31}FN_6O_2$ | 479.25 | 479 |
| 3-29 | —CH₃ | $R^3$ = (S)CH₂OH $R^7$ = —CH₃ | $C_{26}H_{31}FN_6O_2$ | 479.25 | 479 |
| 3-30 | cyclobutyl-OCH₃ | | $C_{28}H_{33}FN_6O_2$ | 505.27 | 505.2 |

TABLE 3-continued

| | | | | | |
|---|---|---|---|---|---|
| 3-31 | tetrahydropyran-4-yl | $R^7$ = —$CH_3$ | $C_{29}H_{35}FN_6O_2$ | 519.28 | 519 |
| 3-32 | oxetan-3-yl | $R^7$ = —$CH_3$ | $C_{27}H_{31}FN_6O_2$ | 491.25 | 491.2 |
| 3-33 | —$CH_2$iPr | $R^7$ = —$CH_3$ | $C_{28}H_{33}FN_6O$ | 489.27 | 489 |
| 3-34 | cPr | $R^7$ = —$CH_3$ | $C_{27}H_{31}FN_6O$ | 475.25 | 475.3 |
| 3-35 | pyridin-4-yl | $R^7$ = —$CH_3$ | $C_{29}H_{30}FN_7O$ | 512.25 | 512.2 |

TABLE 4

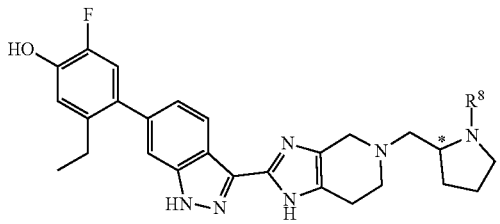

| Ex. No. | $R^8$ | * | Formula | Calc [M + H]$^+$ | Found [M + H]$^+$ |
|---|---|---|---|---|---|
| 4-1 | | (S) | $C_{26}H_{29}FN_6O$ | 461.24 | 461.2 |
| 4-2 | | (R) | $C_{26}H_{29}FN_6O$ | 461.24 | 461.2 |
| 4-3 | —$CH_3$ | (R) | $C_{27}H_{31}FN_6O$ | 475.25 | 475.2 |
| 4-4 | —$C_2H_5$ | (R) | $C_{28}H_{33}FN_6O$ | 489.27 | 489.2 |

TABLE 4-continued

| | | | | | |
|---|---|---|---|---|---|
| 4-5 | —$CH_2$iPr | (R) | $C_{30}H_{37}FN_6O$ | 517.30 | 517.2 |
| 4-6 | cBu | (R) | $C_{30}H_{35}FN_6O$ | 515.29 | 515.2 |
| 4-7 | iPr | (R) | $C_{29}H_{35}FN_6O$ | 503.29 | 503.2 |
| 4-8 | oxetan-3-yl | (R) | $C_{29}H_{33}FN_6O_2$ | 517.27 | 517.2 |
| 4-9 | —$CH_2$iPr | (S) | $C_{30}H_{37}FN_6O$ | 517.30 | 517.2 |
| 4-10 | —cBu | (S) | $C_{30}H_{35}FN_6O$ | 515.29 | 515.2 |
| 4-11 | tetrahydropyran-4-yl | (S) | $C_{31}H_{37}FN_6O_2$ | 545.30 | 545.2 |
| 4-12 | —$C_2H_5$ | (S) | $C_{28}H_{33}FN_6O$ | 489.27 | 489.2 |
| 4-13 | —$CH_2$cPr | (R) | $C_{30}H_{35}FN_6O$ | 515.29 | 515.2 |
| 4-14 | iPr | (S) | $C_{29}H_{35}FN_6O$ | 503.29 | 503.2 |
| 4-15 | —$CH_2$cPr | (S) | $C_{30}H_{35}FN_6O$ | 515.29 | 515.2 |
| 4-16 | oxetan-3-yl | (S) | $C_{29}H_{33}FN_6O_2$ | 517.27 | 517.2 |
| 4-17 | phenyl | (R) | $C_{33}H_{32}FN_7O$ | 538.27 | 538.2 |
| 4-18 | phenyl | (S) | $C_{31}H_{32}FN_7O$ | 538.27 | 538.2 |
| 4-19 | cPr | (S) | $C_{29}H_{33}FN_6O$ | 501.27 | 501.2 |
| 4-20 | cPr | (R) | $C_{29}H_{33}FN_6O$ | 501.27 | 501.2 |

TABLE 5

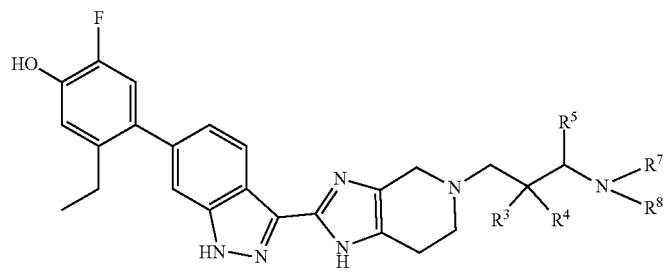

| Ex. No. | $R^8$ | $R^3, R^4, R^5, R^7$ | Formula | Calc [M + H]$^+$ | Found [M + H]$^+$ |
|---|---|---|---|---|---|
| 5-1 | —$CH_3$ | $R^3$ = —$CH_3$<br>$R^4$ = —$CH_3$<br>$R^7$ = —$CH_3$ | $C_{28}H_{35}FN_6O$ | 491.29 | 491.2 |
| 5-2 | iPr | $R^3$ = —OH<br>$R^7$ = —$CH_3$ | $C_{28}H_{33}FN_6O_2$ | 505.27 | 505 |
| 5-3 | —$CH_3$ | $R^3$ = —OH<br>$R^7$ = —$CH_3$ | $C_{26}H_{31}FN_6O_2$ | 479.25 | 479 |
| 5-4 | —$CH_3$ | $R^3$ = —OH<br>$R^4$ = —$CH_3$<br>$R^7$ = —$CH_3$ | $C_{27}H_{33}FN_6O_2$ | 493.27 | 493 |
| 5-5 | | $R^3$ = —OH<br>$R^4$ = —$CH_3$ | $C_{25}H_{29}FN_6O_2$ | 465.23 | 465 |
| 5-6 | | $R^5$ = (S)phenyl | $C_{30}H_{31}FN_6O$ | 511.25 | 511.1 |
| 5-7 | | $R^3$ = (S)OH | $C_{26}H_{31}FN_6O_2$ | 479.25 | 479 |
| 5-8 | | $R^3$ = (R)OH | $C_{26}H_{31}FN_6O_2$ | 479.25 | 479 |
| 5-9 | —$(CH_2)_2$CN | $R^3$ = —OH,<br>$R^7$ = —$CH_3$ | $C_{28}H_{32}FN_7O_2$ | 518.26 | 518.2 |
| 5-10 | —$(CH_2)_2$OCH$_3$ | $R^3$ = —OH,<br>$R^7$ = —$CH_3$ | $C_{28}H_{35}FN_6O_3$ | 523.28 | 523.2 |
| 5-11 | iPr | $R^3$ = —OH,<br>$R^7$ = —$CH_3$ | $C_{28}H_{35}FN_6O_2$ | 507.28 | 507.2 |
| 5-12 | —$C_2H_5$ | $R^3$ = —OH,<br>$R^7$ = —$CH_3$ | $C_{27}H_{33}FN_6O_2$ | 493.27 | 493.2 |
| 5-13 | —$CH_3$ | $R^3$ = —$CH_3$<br>$R^7$ = —$CH_3$ | $C_{27}H_{33}FN_6O$ | 477.27 | 477 |
| 5-14 | | $R^3$ = F | $C_{24}H_{26}F_2N_6O$ | 453.21 | 453 |
| 5-15 | —$CH_3$ | $R_7$ = —$CH_3$ | $C_{26}H_{31}FN_6O$ | 463.25 | 463.1 |
| 5-16 | cPr | $R_7$ = —$CH_3$ | $C_{28}H_{33}FN_6O$ | 489.27 | 489.2 |
| 5-17 | iPr | $R_7$ = —$CH_3$ | $C_{28}H_{35}FN_6O$ | 491.29 | 491.1 |
| 5-18 | cBu | $R^7$ = —$CH_3$ | $C_{29}H_{35}FN_6O$ | 503.29 | 503.6 |

TABLE 5-continued

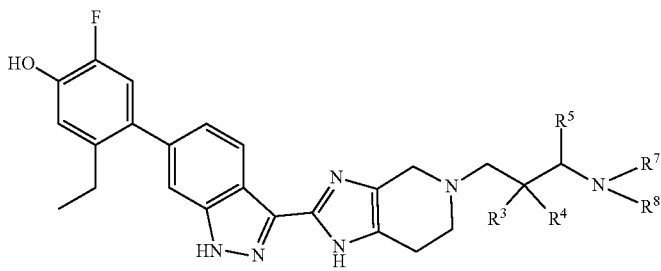

| Ex. No. | R8 | R3, R4, R5, R7 | Formula | Calc [M + H]+ | Found [M + H]+ |
|---|---|---|---|---|---|
| 5-19 | 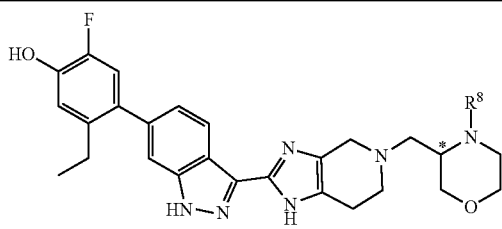 | R7 = —CH3 | C30H37FN6O2 | 533.30 | 533.6 |
| 5-20 | tetrahydropyran-4-yl | R7 = —CH3 | C30H37FN6O2 | 533.30 | 533.6 |
| 5-21 | —CH2CH2F | R7 = —CH3 | C27H32F2N6O | 495.26 | 495.1 |

TABLE 6

| Ex. No. | R8 | * | Formula | Calc [M + H]+ | Found [M + H]+ |
|---|---|---|---|---|---|
| 6-1 | —CH3 | (S) | C27H31FN6O2 | 491.25 | 491.1 |
| 6-2 | —CH3 | (R) | C27H31FN6O2 | 491.25 | 491.2 |
| 6-3 | —CH2phenyl | (R) | C33H35FN6O2 | 567.28 | 567.2 |
| 6-4 | 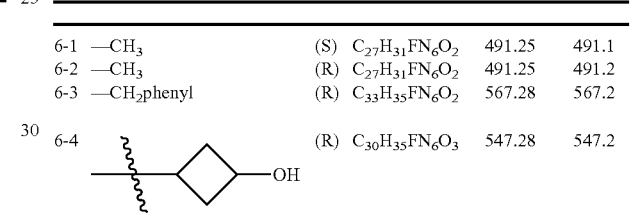 | (R) | C30H35FN6O3 | 547.28 | 547.2 |
| 6-5 | —CH2CH2OH | (R) | C28H33FN6O3 | 521.26 | 521.3 |

TABLE 7

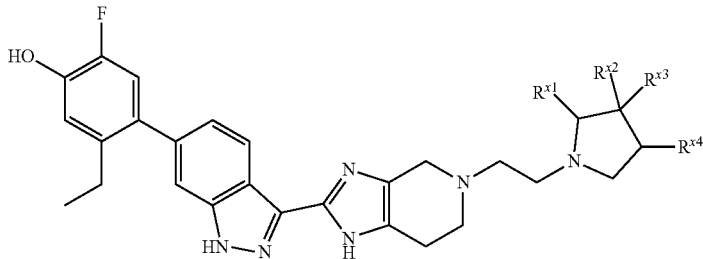

| Ex. No. | Rx1, Rx2, Rx3, Rx4 | Formula | Calc [M + H]+ | Found [M + H]+ |
|---|---|---|---|---|
| 7-1 | Rx2 = (R)F | C27H30F2N6O | 493.25 | 493.2 |
| 7-2 | Rx2 = (S)F | C27H30F2N6O | 493.25 | 493.2 |
| 7-3 | | C27H31FN6O | 475.25 | 475.2 |
| 7-4 | Rx3 and Rx4 form —CH2— | C28H31FN6O | 487.25 | 487.6 |
| 7-5 | Rx1 = -CH2OCH3 | C29H35FN6O2 | 519.28 | 519.2 |
| 7-6 | Rx2 = OH | C27H31FN6O2 | 491.25 | 491.2 |
| 7-7 | Rx2 = -C2H5 | C29H35FN6O | 503.29 | 503.2 |
| 7-8 | Rx2 = phenyl | C33H35FN6O | 551.29 | 551.2 |
| 7-10 | Rx2 = (S)CH2OH | C28H33FN6O2 | 505.27 | 505.2 |
| 7-11 | Rx2 = -OiPr | C30H37FN6O2 | 533.30 | 533.2 |
| 7-12 | Rx2 = -CH2OCH3 | C29H35FN6O2 | 519.28 | 519.2 |

TABLE 8

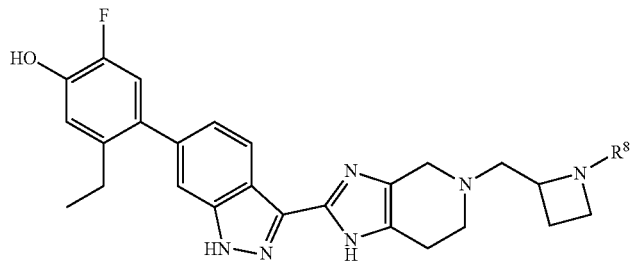

| Ex. No. | R⁸ | Formula | Calc [M + H]⁺ | Found [M + H]⁺ |
|---|---|---|---|---|
| 8-1 |  | $C_{25}H_{27}FN_6O$ | 447.22 | 447.2 |
| 8-2 | -CH₃ | $C_{26}H_{29}FN_6O$ | 461.24 | 461.2 |
| 8-3 | cBu | $C_{29}H_{33}FN_6O$ | 501.27 | 501.2 |
| 8-4 | -CH₂cPr | $C_{29}H_{33}FN_6O$ | 501.27 | 501.2 |
| 8-5 | iPr | $C_{28}H_{33}FN_6O$ | 489.27 | 489.1 |
| 8-6 | tetrahydropyran-4-yl | $C_{30}H_{35}FN_6O_2$ | 531.28 | 531.2 |
| 8-7 | -CH₂iPr | $C_{29}H_{35}FN_6O$ | 503.29 | 503.2 |
| 8-8 | -C₂H₅ | $C_{27}H_{31}FN_6O$ | 475.25 | 475.1 |
| 8-9 | phenyl | $C_{30}H_{30}FN_7O$ | 524.25 | 524.2 |
| 8-10 | cPr | $C_{28}H_{31}FN_6O$ | 487.25 | 487.2 |
| 8-11 | oxetan-3-yl | $C_{28}H_{31}FN_6O_2$ | 503.25 | 503.2 |

TABLE 9

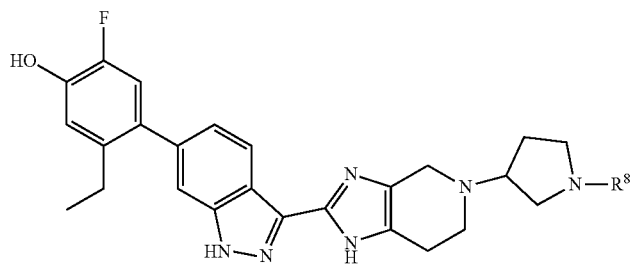

| Ex. No. | R⁸ | Formula | Calc [M + H]⁺ | Found [M + H]⁺ |
|---|---|---|---|---|
| 9-1 |  | $C_{25}H_{27}FN_6O$ | 447.22 | 447.1 |
| 9-2 | -CH₃ | $C_{25}H_{27}FN_6O$ | 461.24 | 461.2 |
| 9-3 | oxetan-3-yl | $C_{28}H_{31}FN_6O_2$ | 503.25 | 503.1 |
| 9-4 | -CH₂iPr | $C_{29}H_{35}FN_6O$ | 503.29 | 503.2 |
| 9-5 | ![sulfolanyl group] | $C_{29}H_{33}FN_6O_3S$ | 565.23 | 565.2 |
| 9-6 | cBu | $C_{29}H_{33}FN_6O$ | 501.27 | 501.3 |
| 9-7 | -C₂H₅ | $C_{27}H_{31}FN_6O$ | 475.25 | 475.2 |
| 9-8 | iPr | $C_{28}H_{33}FN_6O$ | 489.27 | 489.2 |
| 9-9 | -CH₂cPr | $C_{29}H_{33}FN_6O$ | 501.27 | 501.2 |
| 9-10 | tetrahydropyran-4-yl | $C_{30}H_{35}FN_6O_2$ | 531.28 | 531.2 |
| 9-11 | cPr | $C_{28}H_{31}FN_6O$ | 487.25 | 487.2 |
| 9-12 | phenyl | $C_{30}H_{30}FN_7O$ | 524.25 | 524.2 |

TABLE 10

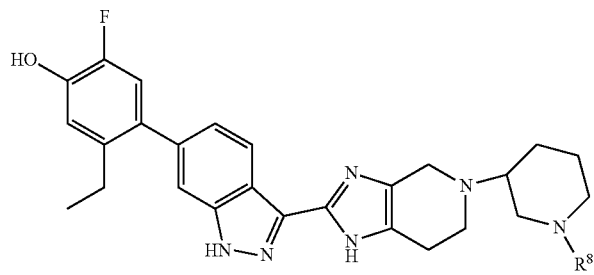

| Ex. No. | R⁸ | Formula | Calc [M + H]⁺ | Found [M + H]⁺ |
|---|---|---|---|---|
| 10-1 | iPr | $C_{29}H_{35}FN_6O$ | 503.29 | 503.2 |
| 10-2 | -CH$_2$iPr | $C_{30}H_{37}FN_6O$ | 517.30 | 517.2 |
| 10-3 | -CH$_2$cPr | $C_{30}H_{35}FN_6O$ | 515.29 | 515.2 |
| 10-4 | -C$_2$H$_5$ | $C_{28}H_{33}FN_6O$ | 489.27 | 489.2 |
| 10-5 | cBu | $C_{30}H_{35}FN_6O$ | 515.29 | 515.2 |
| 10-6 | oxetan-3-yl | $C_{29}H_{33}FN_6O_2$ | 517.27 | 517.2 |
| 10-7 | tetrahydropyran-4-yl | $C_{31}H_{37}FN_6O_2$ | 545.30 | 545.2 |
| 10-8 | -CH$_3$ | $C_{27}H_{31}FN_6O$ | 475.25 | 475.2 |
| 10-9 | cPr | $C_{29}H_{33}FN_6O$ | 501.27 | 501.2 |
| 10-10 | phenyl | $C_{31}H_{32}FN_7O$ | 538.27 | 538.2 |

TABLE 11

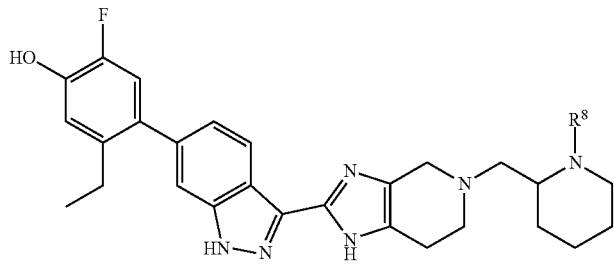

| Ex. No. | R⁸ | Formula | Calc [M + H]⁺ | Found [M + H]⁺ |
|---|---|---|---|---|
| 11-1 | -CH$_3$ | $C_{28}H_{33}FN_6O$ | 489.27 | 489.2 |
| 11-2 | -C$_2$H$_5$ | $C_{29}H_{35}FN_6O$ | 503.29 | 503.2 |
| 11-3 | oxetan-3-yl | $C_{30}H_{35}FN_6O_2$ | 531.28 | 531.2 |
| 11-4 | -CH$_2$iPr | $C_{31}H_{39}FN_6O$ | 531.32 | 531.2 |
| 11-5 | -CH$_2$cPr | $C_{31}H_{37}FN_6O$ | 529.30 | 529.2 |
| 11-6 | cBu | $C_{31}H_{37}FN_6O$ | 529.30 | 529.2 |
| 11-7 | tetrahydropyran-4-yl | $C_{32}H_{39}FN_6O_2$ | 559.31 | 559.2 |
| 11-8 | iPr | $C_{30}H_{37}FN_6O$ | 517.30 | 517.2 |
| 11-9 | cPr | $C_{30}H_{35}FN_6O$ | 515.29 | 515.2 |
| 11-10 | | $C_{27}H_{31}FN_6O$ | 475.25 | 475.2 |

TABLE 12

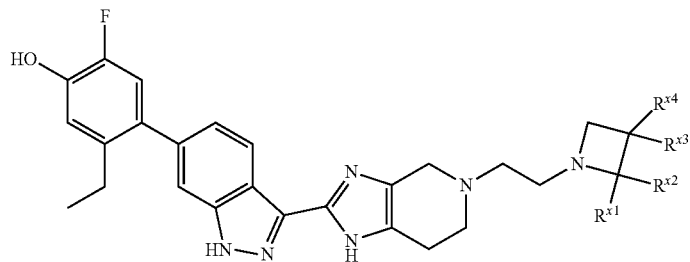

| Ex. No. | $R^{x1}, R^{x2}, R^{x3}, R^{x4}$ | Formula | Calc [M + H]$^+$ | Found [M + H]$^+$ |
|---|---|---|---|---|
| 12-1 | $R^{x3}$ = -CN | $C_{27}H_{28}FN_7O$ | 486.23 | 486.1 |
| 12-2 | $R^{x3}$ = -CN, $R^{x4}$ = -CH$_3$ | $C_{28}H_{30}FN_7O$ | 500.25 | 500.2 |
| 12-3 | $R^{x1}$ = -CH$_3$, $R^{x2}$ = -CH$_3$ | $C_{28}H_{33}FN_6O$ | 489.27 | 489.2 |
| 12-4 | $R^{x3}$ = -CH$_3$ | $C_{27}H_{31}FN_6O$ | 475.25 | 475.1 |
| 12-5 | $R^{x3}$ = -CH$_3$, $R^{x4}$ = -OCH$_3$ | $C_{28}H_{33}FN_6O_2$ | 505.27 | 505.2 |
| 12-6 | $R^{x3}$ = -CH$_2$CH$_2$OH | $C_{28}H_{33}FN_6O_2$ | 505.27 | 505.2 |
| 12-7 | $R^{x3}$ = -CH$_3$, $R^{x4}$ = -CH$_3$ | $C_{28}H_{33}FN_6O$ | 489.27 | 489.2 |
| 12-8 | $R^{x3}$ = -CH$_2$OC$_2$H$_5$ | $C_{29}H_{35}FN_6O_2$ | 519.28 | 519.2 |
| 12-9 | $R^{x3}$ = phenyl | $C_{32}H_{33}FN_6O$ | 537.27 | 537.2 |
| 12-10 | $R^{x3}$ = -CH$_3$, $R^{x4}$ = -OH | $C_{27}H_{31}FN_6O_2$ | 491.25 | 491.2 |
| 12-11 | | $C_{26}H_{29}FN_6O$ | 461.24 | 461.2 |
| 12-12 | $R^{x3}$ = -CH$_2$OH | $C_{27}H_{31}FN_6O_2$ | 491.25 | 491.1 |
| 12-13 | $R^{x3}$ and $R^{x4}$ form —(CH$_2$)$_5$- | $C_{31}H_{37}FN_6O$ | 529.30 | 529.2 |
| 12-14 | $R^{x3}$ and $R^{x4}$ form —CH$_2$OCH$_2$- | $C_{28}H_{31}FN_6O_2$ | 503.25 | 503.2 |
| 12-15 | $R^{x1}$ = phenyl | $C_{32}H_{33}FN_6O$ | 537.27 | 536.6 |

TABLE 13

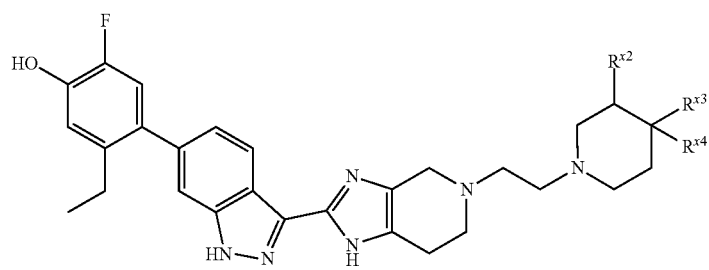

| Ex. No. | $R^{x2}, R^{x3}, R^{x4}$ | Formula | Calc [M + H]$^+$ | Found [M + H]$^+$ |
|---|---|---|---|---|
| 13-1 | | $C_{28}H_{33}FN_6O$ | 489.27 | 489.2 |
| 13-2 | $R^{x3}$ = -OH | $C_{28}H_{33}FN_6O_2$ | 505.27 | 505.2 |
| 13-3 | $R^{x3}$ = -OCH$_3$ | $C_{29}H_{35}FN_6O_2$ | 519.28 | 519.2 |
| 13-4 | $R^{x3}$ = F | $C_{28}H_{32}F_2N_6O$ | 507.26 | 507.2 |
| 13-5 | $R^{x3}$ = -CN | $C_{29}H_{32}FN_7O$ | 514.27 | 514.2 |
| 13-6 | $R^{x3}$ = -CH$_2$OH | $C_{29}H_{35}FN_6O_2$ | 519.28 | 519.2 |
| 13-7 | $R^{x3}$ and $R^{x4}$ form —(CH$_2$)$_3$- | $C_{31}H_{37}FN_6O_2$ | 529.30 | 529.3 |
| 13-8 | $R^{x3}$ = -CH$_2$OH | $C_{29}H_{35}FN_6O_2$ | 519.28 | 519.2 |
| 13-9 | $R^{x2}$ = -OH | $C_{28}H_{33}FN_6O_2$ | 505.27 | 505.2 |

TABLE 14

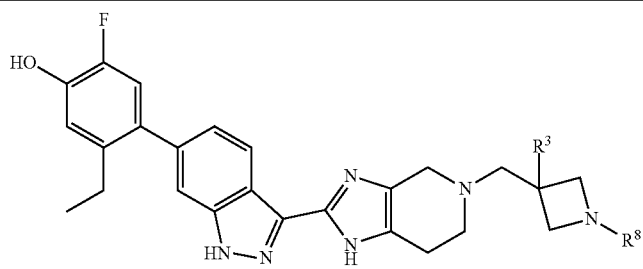

| Ex. No. | R8 | R3 | Formula | Calc [M + H]+ | Found [M + H]+ |
|---|---|---|---|---|---|
| 14-1 | | -OCH3 | $C_{26}H_{29}FN_6O_2$ | 477.23 | 477 |
| 14-2 | -CH3 | -OH | $C_{26}H_{29}FN_6O_2$ | 477.23 | 477 |
| 14-3 | | -OH | $C_{25}H_{27}FN_6O_2$ | 463.22 | 463 |
| 14-4 | -CH3 | -OCH3 | $C_{27}H_{33}FN_6O_2$ | 491.25 | 490 |
| 14-5 | -CH3 | | $C_{26}H_{29}FN_6O$ | 461.24 | 461.1 |
| 14-6 | -CH3 | F | $C_{26}H_{28}F_2N_6O$ | 479.23 | 479 |
| 14-7 | | | $C_{25}H_{27}FN_6O$ | 447.22 | 447.1 |
| 14-8 | | F | $C_{25}H_{26}F_2N_6O$ | 465.21 | 465 |
| 14-9 | cPr | | $C_{28}H_{33}FN_6O$ | 487.25 | 487.2 |
| 14-10 | -(CH2)2CN | | $C_{28}H_{30}FN_7O$ | 500.25 | 500.2 |
| 14-11 | ![methoxycyclobutyl] | | $C_{30}H_{35}FN_6O_2$ | 531.28 | 531.3 |
| 14-12 | cBu | | $C_{29}H_{33}FN_6O$ | 501.27 | 501.3 |
| 14-13 | -(CH2)3OCH3 | | $C_{29}H_{35}FN_6O_2$ | 519.28 | 519.3 |
| 14-14 | -(CH2)2OCH3 | | $C_{28}H_{33}FN_6O_2$ | 505.27 | 505.2 |
| 14-15 | oxetan-3-yl | | $C_{28}H_{31}FN_6O_2$ | 503.25 | 503.2 |

TABLE 15

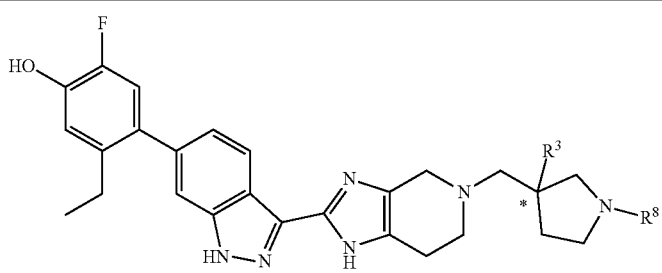

| Ex. No. | R8 | R3 | * | Formula | Calc [M + H]+ | Found [M + H]+ |
|---|---|---|---|---|---|---|
| 15-1 | -CH3 | -OH | | $C_{27}H_{33}FN_6O_2$ | 491.25 | 491 |
| 15-2 | | -OH | | $C_{26}H_{29}FN_6O_2$ | 477.23 | 477 |
| 15-3 | | | (R) | $C_{26}H_{29}FN_6O$ | 461.24 | 461.1 |
| 15-4 | -iPr | | | $C_{29}H_{33}FN_6O$ | 503.29 | 503.6 |
| 15-4 | cBu | | | $C_{30}H_{33}FN_6O$ | 515.29 | 515.6 |
| 15-6 | ![methoxycyclobutyl] | | | $C_{33}H_{37}FN_6O_2$ | 545.30 | 545.6 |
| 15-7 | cPr | | | $C_{29}H_{33}FN_6O$ | 501.27 | 501.2 |
| 15-8 | -CH2CH2F | | | $C_{28}H_{32}F_2N_6O$ | 507.26 | 507.1 |
| 15-9 | -CH3 | | | $C_{27}H_{33}FN_6O$ | 475.25 | 475.2 |
| 15-10 | tetrahydropyran-4-yl | | | $C_{33}H_{37}FN_6O_2$ | 545.30 | 545.2 |

TABLE 16

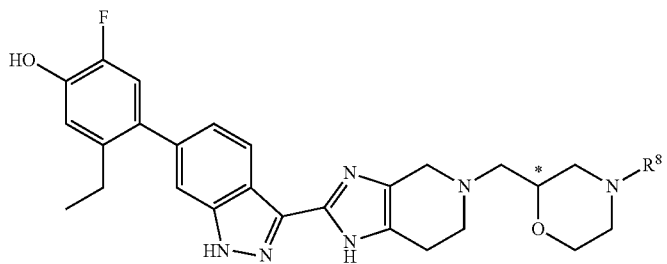

| Ex. No. | R[8] | * | Formula | Calc [M + H]+ | Found [M + H]+ |
|---|---|---|---|---|---|
| 16-1 | -CH$_3$ | (R) | C$_{27}$H$_{31}$FN$_6$O$_2$ | 491.25 | 491.2 |
| 16-2 | | (R) | C$_{26}$H$_{29}$FN$_6$O$_2$ | 477.23 | 477.2 |
| 16-3 | | (S) | C$_{26}$H$_{29}$FN$_6$O$_2$ | 477.23 | 477.2 |
| 16-4 | cBu | (S) | C$_{30}$H$_{33}$FN$_6$O$_2$ | 531.28 | 531.2 |
| 16-5 | cPr | (S) | C$_{29}$H$_{33}$FN$_6$O$_2$ | 517.27 | 517.3 |
| 16-6 | iPr | (S) | C$_{29}$H$_{33}$FN$_6$O$_2$ | 519.28 | 519.6 |

TABLE 17

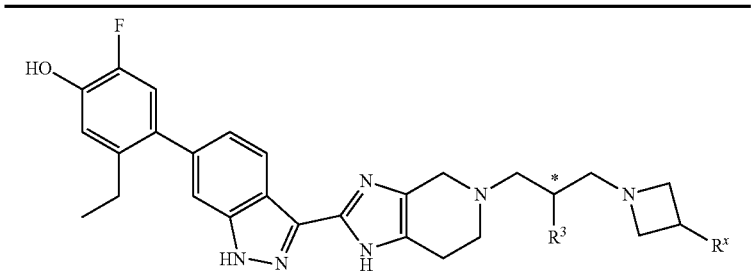

| Ex. No. | R[3] | R[x] | * | Formula | Calc [M + H]+ | Found [M + H]+ |
|---|---|---|---|---|---|---|
| 17-1 | -OH | | (S) | C$_{27}$H$_{31}$FN$_6$O$_2$ | 491.25 | 491 |
| 17-2 | -OH | | (R) | C$_{27}$H$_{31}$FN$_6$O$_2$ | 491.25 | 491 |
| 17-3 | | -CHF$_2$ | | C$_{28}$H$_{31}$F$_3$N$_6$O | 525.25 | 525.2 |

TABLE 18

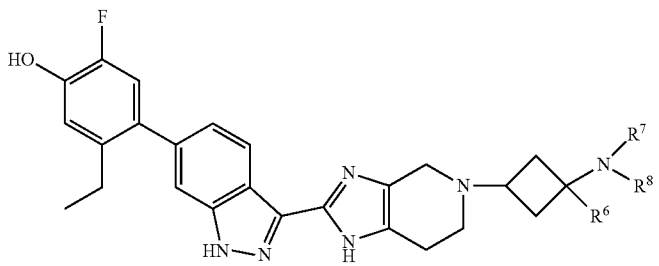

| Ex. No. | R[8] | R[6], R[7] | Formula | Calc [M + H]+ | Found [M + H]+ |
|---|---|---|---|---|---|
| 18-1 | -CH$_3$ | R[7] = -CH$_3$ | C$_{27}$H$_{31}$FN$_6$O | 475.25 | 475.2 |
| 18-2 | -CH$_3$ | R[6] = -CH$_3$, R[7] = -CH$_3$ | C$_{28}$H$_{33}$FN$_6$O | 489.27 | 489 |
| 18-3 | | | C$_{25}$H$_{27}$FN$_6$O | 447.22 | 447.2 |

TABLE 19

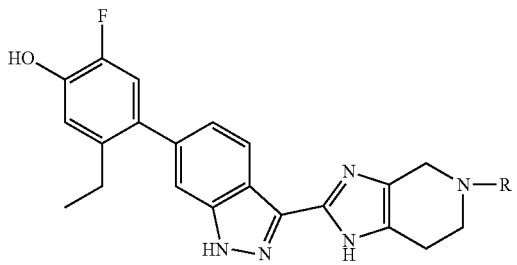

| Ex. No. | R | Formula | Calc [M + H]⁺ | Found [M + H]⁺ |
|---|---|---|---|---|
| 19-1 | 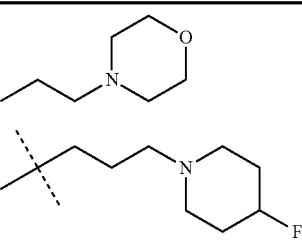 | $C_{27}H_{31}FN_6O_2$ | 491.25 | 491.1 |
| 19-2 | 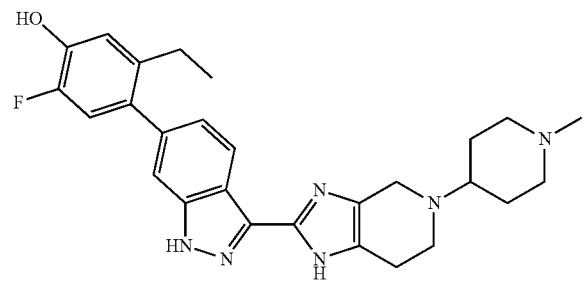 | $C_{29}H_{34}F_2N_6O$ | 521.28 | 521.1 |

Example 17: Crystalline hydrate of 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol To a 3 L flask was added NMP (239 mL) and 5-ethyl-2-fluoro-4-(3-(4,5,6,7-tetrahydro-1H-imidazo[4,5-c]pyridin-2-yl)-1H-indazol-6-yl)phenol, 2 HCl (74.5 g, 165 mmol) with stirring followed by NMP (74 mL). Acetic acid (31.3 mL) was added and the reaction mixture was warmed to 55° C. for 10 min and then cooled to 25° C. 1-methylpiperidin-4-one (61.0 mL, 496 mmol) was added in a single portion and the reaction mixture was stirred at 25° C. for 30 min and cooled to 15° C. Sodium triacetoxyborohydride (98 g, 463 mmol) was added and the external jacket was set to 20° C. after 5 min. After 3 h, ammonium hydroxide (365 mL, 5790 mmol) was added dropwise over 45 min maintaining the temperature below 25° C. The reaction mixture was stirred for 1.5 h at 20° C., forming an off-white slurry. Methanol (709 mL) was added and the reaction mixture was stirred slowly overnight at 55° C. Water (1.19 L) was added over 30 min at 55° C. and the mixture was cooled to 10° C., stirred for 2 h, and filtered. The cake was washed with 1:1 MeOH:water (334 mL), dried on the filter for 20 min and at 45° C. under vacuum with nitrogen bleed to provide yellow solids (87 g).

To the solids was added 5% water/acetone (1.5 L) at 55° C. with slow stirring and the reaction mixture was heated at 55° C. for 6 h, cooled to 10° C., filtered, and washed with 5% water/acetone (450 mL). The solids were dried overnight at 50° C. under vacuum with nitrogen bleed, equilibrated in air for 20 h, dried in the vacuum oven for 48 h and equilibrated with air to provide the title compound (71.3 g, 91% yield) as a free flowing pale yellow solid. HPLC Method C Retention time 12.29 min.

Example 18: Crystalline hydrate of 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol To a flask was added 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol (45.4 g, 95 mmol) and water (450 mL) and 37% NH₄OH (11.25 mL) and the slurry was stirred for 10 min and filtered. The wet cake was transferred to a 2 L flask and 2.5% water/acetone (900 mL) was added and the slurry was stirred overnight. Additional water (23 mL) was added and the mixture was stirred for 48 h, warmed to 55° C. and stirred at 55° C. overnight. Additional water (69 mL) was added and the slurry was stirred at 25° C. overnight and warmed to 55° C. After 3 h, an additional portion of water (23 mL) was added, the mixture was cooled to RT, filtered, and washed with 15% water/acetone (250 mL). The solids were dried overnight in a vacuum oven at 50° C. to provide the title compound (32.4 g, 68.3 mmol, 72% yield, 99/2% purity). HPLC Method C Retention time 12.27 min. ¹H NMR (400 MHz, Methanol-d₄) δ 8.24 (dd, J=8.4, 0.8 Hz, 1H), 7.39 (t, J=1.1 Hz, 1H), 7.13 (dd, J=8.4, 1.4 Hz, 1H), 6.93 (d, J=11.7 Hz, 1H), 6.88 (d, J=9.0 Hz, 1H), 3.78 (s, 2H), 3.00 (dd, J=10.0, 4.0 Hz, 4H), 2.81 (t, J=5.8 Hz, 2H), 2.68-2.57 (m, 1H), 2.53 (q, J=7.5 Hz, 2H), 2.30 (s, 3H), 2.18-2.06 (m, 2H), 1.99 (d, J=11.9 Hz, 2H), 1.75 (td, J=12.4, 3.7 Hz, 2H), 1.05 (t, J=7.5 Hz, 3H).

Comparison Example C-1: 5-Ethyl-2-fluoro-4-(3-(5-(3-methylcyclobutyl)-4,5,6,7-tetrahydro-1H-imidazo[4,5-c]pyridin-2-yl)-1H-indazol-6-yl)phenol

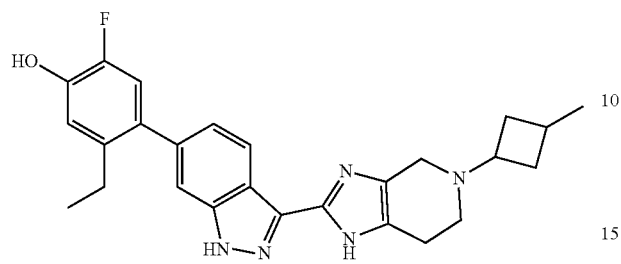

To a solution of 5-ethyl-2-fluoro-4-(3-(4,5,6,7-tetrahydro-1H-imidazo[4,5-c]pyridin-2-yl)-1H-indazol-6-yl)phenol TFA (60 mg, 0.122 mmol) and 3-methylcyclobutan-1-one (51 mg, 0.610 mmol) in MeOH (1.221 mL) was added sodium cyanoborohydride (77 mg, 1.221 mmol) and the reaction mixture was stirred for 4 h. The reaction mixture was concentrated by rotary evaporation, dissolved in 2:1 acetic acid:water (1.5 mL) and purified by preparative HPLC to provide the TFA salt of the title compound (40 mg). (m/z): [M+H]$^+$ calcd for $C_{26}H_{28}FN_5O$, 446.23 found 446.1.

Using a similar process, substituting the appropriate reagent for 3-methylcyclobutan-1-one, the following comparison compounds were prepared:

Comparison Compounds C-2 to C-4

| Ex No. | R | Formula | Calc [M + H]$^+$ | Found [M + H]$^+$ |
|---|---|---|---|---|
| C-2 | (isobutyl) | $C_{26}H_{30}FN_5O$ | 448.24 | 448.2 |
| C-3 | (tetrahydropyran-3-ylmethyl) | $C_{27}H_{30}FN_5O_2$ | 476.24 | 476.2 |
| C-4 | (4-methylcyclohexyl) | $C_{28}H_{32}FN_5O$ | 474.26 | 474.2 |

Examples 19-21: Properties of the Solid Form of the Invention

Samples of the crystalline hydrate 5-ethyl-2-fluoro-4-(3-(5-(1-methylpiperidin-4-yl)-4,5,6,7-tetrahydro-1H-imidazo[4,5-c]pyridin-2-yl)-1H-indazol-6-yl)phenol of Example 18 was analyzed by powder X-ray diffraction (PXRD), differential scanning calorimetry (DSC), thermogravimetric analysis (TGA), and dynamic moisture sorption (DMS).

Example 19 Powder X-Ray Diffraction

The powder X-ray diffraction patterns of FIG. 1 was obtained with a Bruker D8-Advance X-ray diffractometer using Cu-Kα radiation (λ=1.54051 Å) with output voltage of 45 kV and current of 40 mA. The instrument was operated in Bragg-Brentano geometry with incident, divergence, and scattering slits set to maximize the intensity at the sample. For measurement, a small amount of powder (5-25 mg) was gently pressed onto a sample holder to form a smooth surface and subjected to X-ray exposure. The samples were scanned in 2θ-2θ mode from 2° to 40° in 2θ with a step size of 0.02° and a scan speed of 0.30° seconds per step. The data acquisition was controlled by Bruker DiffracSuite measurement software and analyzed by Jade software (version 7.5.1). The instrument was calibrated with a corundum standard, within ±0.02° two-theta angle. Observed PXRD two-theta peak positions and d-spacings are shown in Table 20.

TABLE 20

PXRD Data for the Crystalline Hydrate

| 2-Theta | d (Å) | Area | A % |
|---|---|---|---|
| 6.20 | 14.24 | 81639 | 45.70 |
| 9.58 | 9.22 | 178629 | 100.00 |
| 10.34 | 8.55 | 30022 | 16.80 |
| 10.65 | 8.30 | 12801 | 7.20 |
| 11.54 | 7.66 | 27220 | 15.20 |
| 12.77 | 6.93 | 27705 | 15.50 |
| 13.01 | 6.80 | 48785 | 27.30 |
| 13.39 | 6.61 | 9261 | 5.20 |
| 16.94 | 5.23 | 40031 | 22.40 |
| 17.53 | 5.05 | 83718 | 46.90 |
| 18.67 | 4.75 | 9542 | 5.30 |
| 19.28 | 4.60 | 152922 | 85.60 |
| 20.02 | 4.43 | 22391 | 12.50 |
| 20.61 | 4.31 | 30308 | 17.00 |
| 21.51 | 4.13 | 92875 | 52.00 |
| 22.10 | 4.02 | 37495 | 21.00 |
| 22.79 | 3.90 | 13802 | 7.70 |
| 23.22 | 3.83 | 12117 | 6.80 |
| 25.16 | 3.54 | 13792 | 7.70 |
| 28.80 | 3.10 | 14487 | 8.10 |
| 29.62 | 3.01 | 14810 | 8.30 |
| 30.20 | 2.96 | 9709 | 5.40 |

Example 20: Thermal Analysis

Differential scanning calorimetry (DSC) was performed using a TA Instruments Model Q-100 module with a Thermal Analyst controller. Data were collected and analyzed using TA Instruments Thermal Analysis software. A sample of each crystalline form was accurately weighed into a covered aluminum pan. After a 5 minute isothermal equilibration period at 5° C., the sample was heated using a linear heating ramp of 10° C./min from 0° C. to 250° C. A representative DSC thermogram of the Form I crystalline freebase of the invention is shown in FIG. 2.

Thermogravimetric analysis (TGA) measurements were performed using a TA Instruments Model Q-50 module equipped with high resolution capability. Data were collected using TA Instruments Thermal Analyst controller and analyzed using TA Instruments Universal Analysis software. A weighed sample was placed onto a platinum pan and scanned with a heating rate of 10° C. from ambient temperature to 300° C. The balance and furnace chambers were purged with nitrogen flow during use. A representative TGA trace of the Form I crystalline freebase of the invention is shown in FIG. 3.

Example 21: Dynamic Moisture Sorption Assessment

Dynamic moisture sorption (DMS) measurement was performed using a VTI atmospheric microbalance, SGA-100 system (VTI Corp., Hialeah, Fla. 33016). A weighed sample was used and the humidity was lowest possible value (close to 0% RH) at the start of the analysis. The DMS analysis consisted of an initial drying step (~0% RH) for 120 minutes, followed by two cycles of sorption and desorption with a scan rate of 5% RH/step over the humidity range of 5% RH to 90% RH. The DMS run was performed isothermally at 25° C. A representative DMS trace for the Form I crystalline freebase of the invention is shown in FIG. 4.

BIOLOGICAL ASSAYS

The compounds of the invention have been characterized in one or more of the following biological assays.

Assay 1: Biochemical JAK and Off-Target Kinase Assays

A panel of four LanthaScreen JAK biochemical assays (JAK1, 2, 3 and Tyk2) were carried in a common kinase reaction buffer (50 mM HEPES, pH 7.5, 0.01% Brij-35, 10 mM $MgCl_2$, and 1 mM EGTA). Recombinant GST-tagged JAK enzymes and a GFP-tagged STAT1 peptide substrate were obtained from Life Technologies.

Serially diluted compounds were pre-incubated with each of the four JAK enzymes and the substrate in white 384-well microplates (Corning) at ambient temperature for 1 h. ATP was subsequently added to initiate the kinase reactions in 10 µL total volume, with 1% DMSO. The final enzyme concentrations for JAK1, 2, 3 and Tyk2 are 4.2 nM, 0.1 nM, 1 nM, and 0.25 nM respectively; the corresponding Km ATP concentrations used are 2 µM, 3 µM, 1.6 µM, and 1 µM; while the substrate concentration is 200 nM for all four assays. Kinase reactions were allowed to proceed for 1 hour at ambient temperature before a 10 µL preparation of EDTA (10 mM final concentration) and Tb-anti-pSTAT1 (pTyr701) antibody (Life Technologies, 2 nM final concentration) in TR-FRET dilution buffer (Life Technologies) was added. The plates were allowed to incubate at ambient temperature for 1 h before being read on the EnVision reader (Perkin Elmer). Emission ratio signals (520 nm/495 nm) were recorded and utilized to calculate the percent inhibition values based on DMSO and background controls.

For dose-response analysis, percent inhibition data were plotted vs. compound concentrations, and $IC_{50}$ values were determined from a 4-parameter robust fit model with the Prism software (GraphPad Software). Results were expressed as $pIC_{50}$ (negative logarithm of $IC_{50}$) and subsequently converted to $pK_i$ (negative logarithm of dissociation constant, Ki) using the Cheng-Prusoff equation.

Test compounds having a higher $pK_i$ value in each of the four JAK assays show greater inhibition of JAK activity. Compounds of the invention tested in this assay typically exhibited $pK_i$ values between about 9 and about 10.5

A panel of off-target tyrosine kinase assays (Flt3, RET, FGFR2, TrkA, and pDGFRβ) were developed using a similar methodology, with recombinant enzymes obtained from Life Technologies and biotinylated peptide substrates synthesized at AnaSpec. All assays were carried out at ambient temperature with a final ATP concentration of 100 µM. Detection reagents, including Eu-anti-phosphotyrosine (pY20) antibody and SureLight APC-SA, were purchased from Perkin Elmer. Emission ratio signals (665 nm/615 nm) were recorded and utilized for data analysis, and the final results were expressed as $pIC_{50}$.

Assay 2: Cellular JAK1 Potency Assay

The AlphaScreen JAK1 cellular potency assay was carried out by measuring interleukin-13 (IL-13, R&D Systems) induced STAT6 phosphorylation in BEAS-2B human lung epithelial cells (ATCC). The anti-STAT6 antibody (Cell Signaling Technologies) was conjugated to AlphaScreen acceptor beads (Perkin Elmer), while the anti-pSTAT6 (pTyr641) antibody (Cell Signaling Technologies) was biotinylated using EZ-Link Sulfo-NHS-Biotin (Thermo Scientific).

BEAS-2B cells were grown at 37° C. in a 5% $CO_2$ humidified incubator in 50% DMEM/50% F-12 medium (Life Technologies) supplemented with 10% FBS (Hyclone), 100 U/mL penicillin, 100 µg/mL streptomycin (Life Technologies), and 2 mM GlutaMAX (Life Technologies). On day 1 of the assay, cells were seeded at a 7,500 cells/well density in white poly-D-lysine-coated 384-well plates (Corning) with 25 µL medium, and were allowed to adhere overnight in the incubator. On day 2 of the assay, the medium was removed and replaced with 12 L of assay buffer (Hank's Balanced Salt Solution/HBSS, 25 mM HEPES, and 1 mg/ml bovine serum albumin/BSA) containing dose-responses of test compounds. Compounds were serially diluted in DMSO and then diluted another 1000-fold in media to bring the final DMSO concentration to 0.1%. Cells were incubated with test compounds at 37° C. for 1 h, and followed by the addition of 12 µl of pre-warmed IL-13 (80 ng/ml in assay buffer) for stimulation. After incubating at 37° C. for 30 min, the assay buffer (containing compound and IL-13) was removed, and 10 µl of cell lysis buffer (25 mM HEPES, 0.1% SDS, 1% NP-40, 5 mM $MgCl_2$, 1.3 mM EDTA, 1 mM EGTA, and supplement with Complete Ultra mini protease inhibitors and PhosSTOP from Roche Diagnostics). The plates were shaken at ambient temperature for 30 min before the addition of detection reagents. A mixture of biotin-anti-pSTAT6 and anti-STAT6 conjugated acceptor beads was added first and incubated at ambient temperature for 2 h, followed by the addition of streptavidin conjugated donor beads (Perkin Elmer). After a minimum of 2 h incubation, the assay plates were read on the EnVision plate reader. AlphaScreen luminescence signals were recorded and utilized to calculate the percent inhibition values based on DMSO and background controls.

For dose-response analysis, percent inhibition data were plotted vs. compound concentrations, and $IC_{50}$ values were determined from a 4-parameter robust fit model with the Prism software. Results were expressed as the negative logarithm of the $IC_{50}$ value, $pIC_{50}$.

Test compounds having a higher $pIC_{50}$ value in this assay show greater inhibition of IL-13 induced STAT6 phosphorylation. Compounds of the invention tested in this assay typically exhibited $pIC_{50}$ values between about 7.5 and about 8.5.

Assay 3: Cytotoxicity Assay

A CellTiter-Glo luminescent cell viability/cytotoxicity assay was carried out in BEAS-2B human lung epithelial cells (ATCC) under the normal growth condition.

Cells were grown at 37° C. in a 5% $CO_2$ humidified incubator in 50% DMEM/50% F-12 medium (Life Technologies) supplemented with 10% FBS (Hyclone), 100 U/mL penicillin, 100 µg/mL streptomycin (Life Technologies), and 2 mM GlutaMAX (Life Technologies). On day 1 of the assay, cells were seeded at a 500 cells/well density in white 384-well tissue culture plates (Corning) with 25 µL medium, and were allowed to adhere overnight in the incubator. On day 2 of the assay, 5 µL of medium containing dose-responses of test compounds was added, and incubated at 37° C. for 48 h. 30 µl of CellTiter-Glo detection solution (Promega) was subsequently added, mixed on an orbital shaker for 5 min, and incubated for additional 10 min before being read on the EnVision reader. Luminescence signals were recorded and percent DMSO control values were calculated.

For dose-response analysis, percent DMSO control data were plotted vs. compound concentrations to derive dose-response curves by line connecting each data point. The concentration at which each curve crosses the 15% inhibition threshold is defined as $CC_{15}$. Results were expressed as the negative logarithm of the $CC_{15}$ value, $pCC_{15}$.

It is expected that test compounds exhibiting a lower $pCC_{15}$ value in this assay have less likelihood to cause cytotoxicity. Compounds of the invention tested in this assay typically exhibited $pCC_{15}$ values between less than 5 and about 6.6.

In Vitro Assay Results

All of the compounds of Examples 1 to 16 and Tables 1 to 19 were tested in one or more of the assays described above. In the following tables, for the JAK1, JAK 2, JAK3, and TYK2 enzyme assays, A represents a $pK_i$ value≥10 ($K_i$≤0.1 nM), B represents a $pK_i$ value between 9 and 10 ($K_i$ between 1 nM and 0.1 nM), C represents a $pK_i$ value between 9 and 9.5 ($K_i$ between 1 nM and 0.32 nM), and D represents a $pK_i$ value between 8.5 and 9 ($K_i$ between 32 nM and 1 nM). For the BEAS-2B cell potency assay, A represents a $pIC_{50}$ value≥8 ($IC_{50}$≤10 nM) and B represents a $pIC_{50}$ value between 7.4 and 8 ($IC_{50}$ between 40 nM and 10 nM). The following compounds were tested in all of the in vitro assays described above.

| Example Number | JAK 1 (pK$_i$) | JAK 2 (pK$_i$) | JAK 3 (pK$_i$) | Tyk 2 (pK$_i$) | BEAS-2B pIC$_{50}$ |
|---|---|---|---|---|---|
| 1 | A | A | A | B | A |
| 2 | A | A | A | B | B |
| 3 | A | A | B | B | A |
| 4 | A | A | B | B | A |
| 5 | A | A | B | C | A |
| 6 | A | A | B | B | A |
| 7 | A | A | B | C | A |
| 8 | A | A | B | B | A |
| 9 | A | A | B | C | A |
| 10 | A | A | B | B | A |
| 11 | B | A | B | C | A |
| 12 | A | A | B | C | A |
| 13 | A | A | B | C | A |
| 14 | A | A | B | B | A |
| 15 | A | A | B | C | A |
| 16 | A | A | A | B | A |
| 1-1 | A | A | B | C | B |
| 1-3 | A | A | A | C | B |
| 1-6 | A | A | A | C | A |
| 1-8 | A | A | A | C | A |

-continued

| Example Number | JAK 1 (pK$_i$) | JAK 2 (pK$_i$) | JAK 3 (pK$_i$) | Tyk 2 (pK$_i$) | BEAS-2B pIC$_{50}$ |
|---|---|---|---|---|---|
| 2-3 | A | A | B | B | B |
| 3-30 | A | A | B | B | A |
| 4-1 | B | B | C | D | B |
| 4-2 | A | A | A | C | B |
| 7-3 | A | A | A | B | A |
| 9-1 | A | A | B | C | B |
| 9-2 | A | A | A | C | A |
| 14-7 | A | A | A | C | B |

It was observed that JAK 1 enzyme potency was predictive of cellular potency in the BEAS-2B assay. Therefore all of the remaining compounds were tested in the JAK1 enzyme assay and the cellular assay and exhibited a pKi enzyme value between 9 and 10.5 and a BEAS-2B $pIC_{50}$ value between 7.4 and 8.5 with the exception of compounds 3-32, 4-8. 4-16. and 8-11, which exhibited JAK inhibition at a $pK_i$ enzyme value between 8.5 and 9 and cellular potency between 6 and 7.4.

Assay 4: Pharmacokinetics in Plasma and Lung in Mouse

Plasma and lung levels of test compounds and ratios thereof were determined in the following manner. BALB/c mice from Charles River Laboratories were used in the assay. Test compounds were individually formulated in 20% propylene glycol in pH 4 citrate buffer at a concentration of 0.2 mg/mL and 50 uL of the dosing solution was introduced into the trachea of a mouse by oral aspiration. At various time points (typically 0.167, 2, 6, 24 hr) post dosing, blood samples were removed via cardiac puncture and intact lungs were excised from the mice. Blood samples were centrifuged (Eppendorf centrifuge, 5804R) for 4 minutes at approximately 12,000 rpm at 4° C. to collect plasma. Lungs were padded dry, weighed, and homogenized at a dilution of 1:3 in sterile water. Plasma and lung levels of test compound were determined by LC-MS analysis against analytical standards constructed into a standard curve in the test matrix. A lung to plasma ratio was determined as the ratio of the lung AUC in µg hr/g to the plasma AUC in µg hr/mL, where AUC is conventionally defined as the area under the curve of test compound concentration vs. time. Compounds of the invention exhibited exposure in lung from one to two orders of magnitude greater than exposure in plasma in mouse. All of the compounds profiled in this assay exhibited a half-life between about 5 and about 12 hours.

Assay 5: Murine (Mouse) Model of IL-13 Induced pSTAT6 Induction in Lung Tissue

I1-13 is an important cytokine underlying the pathophysiology of asthma (Kudlacz et al. Eur. *J Pharmacol*, 2008, 582, 154-161). IL-13 binds to cell surface receptors activating members of the Janus family of kinases (JAK) which then phosphorylate STAT6 and subsequently activates further transcription pathways. In the described model, a dose of IL-13 was delivered locally into the lungs of mice to induce the phosphorylation of STAT6 (pSTAT6) which is then measured as the endpoint.

Adult balb/c mice from Harlan were used in the assay. On the day of study, animals were lightly anesthetized with isoflurane and administered either vehicle or test compound (0.5 mg/mL, 50 µL total volume over several breaths) via oral aspiration. Animals were placed in lateral recumbency post dose and monitored for full recovery from anesthesia before being returned to their home cage. Four hours later, animals were once again briefly anesthetized and challenged with either vehicle or IL-13 (0.03 g total dose delivered, 50

µL total volume) via oral aspiration before being monitored for recovery from anesthesia and returned to their home cage. One hour after vehicle or IL-13 administration, lungs were collected for both pSTAT6 detection using an anti-pSTAT6 ELISA (rabbit mAb capture/coating antibody; mouse mAb detection/report antibody: anti-pSTAT6-pY641; secondary antibody: anti-mouse IgG-HRP) and analyzed for total drug concentration as described above in Assay 4.

Selected compounds of the invention were tested in the assay. Activity in the model is evidenced by a decrease in the level of pSTAT6 present in the lungs of treated animals at 5 hours compared to the vehicle treated, IL-13 challenged control animals. The difference between the control animals which were vehicle-treated, IL-13 challenged and and the control animals which were vehicle-treated, vehicle challenged dictated the 0% and 100% inhibitory effect, respectively, in any given experiment. Exemplary compounds of the invention were tested in the assay, and exhibited inhibition of STAT6 phosphorylation at 4 hours after IL-13 challenge as documented below. The compounds 1-15 and 3-1 were noted as exceptions under the conditions of the assay.

Confirming the relevance of the JAK-STAT pathway in airway inflammation, compounds which have demonstrated in vivo target engagement in the IL13-induced pSTAT6 mouse model are subsequently tested and proven to be efficacious in a mouse model of allergen-induced eosinophilic inflammation.

In Vivo Assay Results

Selected compounds of the invention were characterized in both the pharmacokinetic assay (Assay 4) and pharmacodynamic assay (Assay 5). A good correlation was observed between test compound concentration in lung determined in the pharmacokinetic assay and in the pharmacodynamic assay at a similar time points post dosing. Observation of significant compound concentration in the mouse lung in the pharmacodynamic assay confirmed that the observed inhibition of IL-13 induced pSTAT6 induction was a result of the activity of the test compound.

In the following table, for the ratio of lung exposure to plasma exposure (Assay 4), A denotes a ratio>100, B denotes a ratio between 50 and 100, and C denotes a ratio between 10 and 50. For the percent inhibition of IL-13 induced pSTAT6 induction (Assay 5), A represents>65% inhibition, B represents between 50% and 65% inhibition and C represents between 33% and 50% inhibition.

| Example Number | Lung to Plasma ratio Assay 4 | pSTAT6 inhibition Assay 5 |
| --- | --- | --- |
| 1 | B | A |
| 2 | C | C |
| 3 | C | A |
| 4 | B | A |
| 5 | C | A |
| 6 | B | B |
| 7 | B | A |
| 8 | A | B |
| 9 | B | B |
| 10 | B | C |
| 11 | A | C |
| 12 | C | C |
| 13 | A | C |
| 14 | A | A |
| 15 | A | B |
| 1-7 | B | C |
| 1-11 | C | C |
| 1-18 | B | C |
| 3-33 | A | C |
| 14-7 | A | B |

Assay 6: Murine Model of *Alternaria alternata*-Induced Eosinophilic Inflammation of the Lung Airway eosinophilia is a hallmark of human asthma. *Alternaria alternata* is a fungal aeroallergen that can exacerbate asthma in humans and induces eosinophilic inflammation in the lungs of mice (Havaux et al. *Clin Exp Immunol.* 2005, 139(2):179-88). In mice, it has been demonstrated that alternaria indirectly activates tissue resident type 2 innate lymphoid cells in the lung, which respond to (e.g. IL-2 and IL-7) and release JAK-dependent cytokines (e.g. IL-5 and IL-13) and coordinate eosinophilic inflammation (Bartemes et al. *J Immunol.* 2012, 188(3):1503-13).

Seven- to nine-week old male C57 mice from Taconic were used in the study. On the day of study, animals were lightly anesthetized with isoflurane and administered either vehicle or test compound (0.1-1.0 mg/mL, 50 L total volume over several breaths) via oropharyngeal aspiration. Animals were placed in lateral recumbency post dose and monitored for full recovery from anesthesia before being returned to their home cage. One hour later, animals were once again briefly anesthetized and challenged with either vehicle or alternaria extract (200 ug total extract delivered, 50 µL total volume) via oropharyngeal aspiration before being monitored for recovery from anesthesia and returned to their home cage. Forty-eight hours after alternaria administration, bronchoalveolar lavage fluid (BALF) was collected and eosinophils were counted in the BALF using the Advia 120 Hematology System (Siemens).

Selected compounds of the invention were tested in this alternaria assay. Activity in the model is evidenced by a decrease in the level of eosinophils present in the BALF of treated animals at forty-eight hours compared to the vehicle treated, alternaria challenged control animals. Data are expressed as percent inhibition of the vehicle treated, alternaria challenged BALF eosinophils response. To calculate percent inhibition, the number of BALF eosinophils for each condition is converted to percent of the average vehicle treated, alternaria challenged BALF eosinophils and subtracted from one-hundred percent. Exemplary compounds of the invention were tested in the assay and exhibited inhibition of BALF eosinophil counts at forty-eight hours after alternaria challenge as documented below.

In Vivo Assay Results

All of the compounds tested demonstrated a range of inhibition (60%-98%) of alternaria-induced BALF eosinophils. The following table reflects the maximum statistically significant percent inhibition of the vehicle treated, alternaria challenged level of eosinophil induction.

| Example Number | Percent Inhibition of Alternaria-induced BALF Eosinophils |
| --- | --- |
| 1 | 98 |
| 2 | 93 |

| Example Number | Percent Inhibition of Alternaria-induced BALF Eosinophils |
|---|---|
| 3 | 61 |
| 6 | 88 |
| 7 | 96 |
| 8 | 60 |
| 11 | 71 |
| 13 | 82 |

Characterization of Comparison Compounds

The correspondence between the comparison compounds and a compound of the invention is illustrated below.

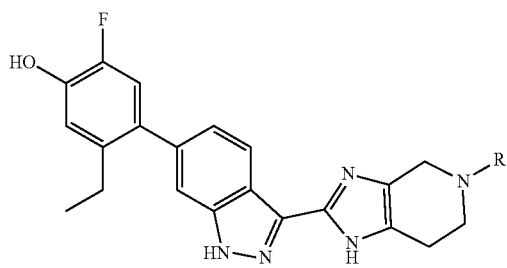

The comparison compounds were characterized in the JAK1 enzyme assay, the BEAS-2B cellular assay and the pSTAT6 inhibition pharmacodynamic assay. Comparison compounds C-1, C-2, C-3, and C-4 were 2-fold, 3-fold, 6-fold, and 2.5-fold less potent, respectively, than the corresponding compound of the invention in the enzyme assay and 6-fold, 6-fold, 3-fold, and 6-fold less potent, respectively, than the corresponding compound of the invention in the BEAS-2B cellular assay. The comparison compounds did not exhibit pSTAT6 inhibition in the pharmacodynamic assay. Also, in that assay, the compounds did not show significant lung concentration. The lung concentration observed for comparison compounds C-1, C-2, C-3, and C-4 was smaller than that observed for the corresponding compound of the invention by a factor of 36, 52, 13, and 23, respectively.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statutes and regulations, all publications, patents and patent applications cited herein are hereby incorporated by reference in their entirety to the same extent as if each document had been individually incorporated by reference herein.

What is claimed is:

1. A process of preparing a compound of formula (IV):

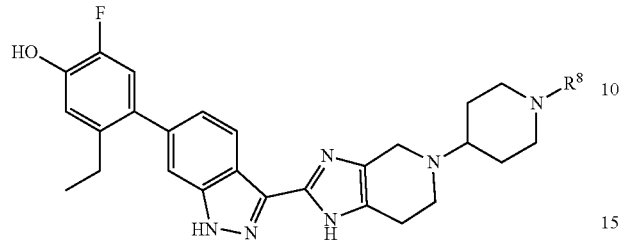

(IV)

or a pharmaceutically-acceptable salt thereof,
wherein $R^8$ is selected from hydrogen, methyl, $C_{2-4}$alkyl, and $C_{3-4}$cycloalkyl, the process comprising reacting a compound of formula 1:

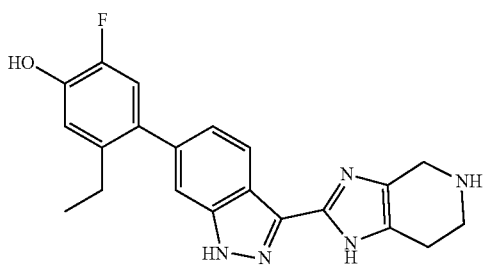

1 with a compound of formula 2":

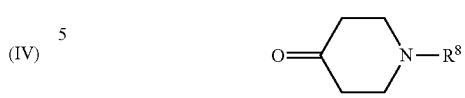

2"

to provide a compound of formula (IV) or a pharmaceutically-acceptable salt thereof.

2. The process of claim 1, wherein the reaction between the compound of formula 1 and the compound of formula 2" occurs in the presence of a reducing agent.

3. The process of claim 2, wherein the reducing agent is sodium cyanoborohydride.

4. The process of claim 2, wherein the reducing agent is sodium triacetoxyborohydride.

5. The process of claim 2, wherein the reaction between the compound of formula 1 and the compound of formula 2" occurs in the presence of acetic acid.

6. The process of claim 2, wherein the reaction between the compound of formula 1 and the compound of formula 2" is conducted at a temperature in the range of about 20° C. to about 40° C.

7. The process of claim 2, wherein the reaction between the compound of formula 1 and the compound of formula 2" is conducted in an inert diluent.

8. The process of claim 7, wherein the inert diluent is dichloromethane, methanol, tetrahydrofuran, or dimethylformamide.

9. The process of claim 7, wherein the inert diluent is dimethylformamide.

10. The process of claim 2, wherein $R^8$ is hydrogen.

11. The process of claim 2, wherein $R^8$ is methyl.

12. The process of claim 2, wherein $R^8$ is $C_{2-4}$alkyl.

13. The process of claim 2, wherein $R^8$ is $C_{3-4}$cycloalkyl.

* * * * *